(12) United States Patent
Markland, Jr. et al.

(10) Patent No.: US 6,710,030 B1
(45) Date of Patent: Mar. 23, 2004

(54) CONTORTROSTAIN (CN) AND METHODS FOR ITS USE IN PREVENTING METASTASIS AND OTHER CONDITIONS

(75) Inventors: Francis S. Markland, Jr., Manhattan Beach, CA (US); Qing Zhou, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/460,295

(22) Filed: Dec. 10, 1999

Related U.S. Application Data

(63) Continuation-in-part of application No. 09/163,047, filed on Sep. 29, 1998, now abandoned, which is a continuation-in-part of application No. 08/745,603, filed on Nov. 8, 1996, now Pat. No. 5,814,609, which is a continuation-in-part of application No. 08/632,691, filed on Apr. 15, 1996, now Pat. No. 5,731,288, which is a division of application No. 08/540,423, filed on Oct. 10, 1995, now abandoned, which is a continuation of application No. 08/141,321, filed on Oct. 22, 1993, now abandoned.

(51) Int. Cl.$^7$ ............................................. A61K 38/00
(52) U.S. Cl. ...................... 514/12; 530/324; 536/23.1; 935/60
(58) Field of Search ........................ 530/324; 514/12; 935/60; 536/23.1

(56) References Cited

FOREIGN PATENT DOCUMENTS

| EP | 323722 | * 12/1989 |
| FR | 2736266 | * 10/1997 |

OTHER PUBLICATIONS

Database CaPlus DN:121:172648. Fujisawa, Y. et al. Takeda Kenkyushoho (1994), 53, 39–56.*

Clark, E.A. ,et al., "Structurally Distinct Disintegrins Contortrostatin and Multisquamatin Differentially Regulate Platelet Tyrosine Phosphorylation," The Journal of Biological Chemistry 269 (35):21940–21943 (1994).

Miyamoto, S., et al., "Integrin Function: Molecular Hierarchies of Cytoskeletal and Signaling Molecules," The Journal of Cell Biology 131(3):791–805 (1995).

Huang, M., et al., "Adhesive Ligand Binding to Integrin Alpha IIb Beta 3 Stimulates Tyrosine Phosphorylation of Novel Protein Substrates before Phosphorylation of pp1125FAK," The Journal of Cell Biology 122(2):473–483 (1993).

Lipfert, L., et al., "Integrin–Dependent Phosphorylation and activation of the Protein Tyrosine Kinase pp125FAK in Platelets," The Journal of Cell Biology 119(4):905–912 (1992).

Kornberg, L., et al., "Cell Adhesion or Integrin Clustering Increases Phosphorylation of a Focal Adhesion–associated Tyrosine Kinase," The Journal of Biological Chemistry 267(33): 23439–23442 (1992).

Kornberg, L., et al., "Signal transduction by integrins: Increased protein tyrosine phosphorylation caused by clustering of Beta1 integrins," Proc. Natl. Acad. Sci. USA 88:8392–8396 (1991).

Bhattacharya, S., et al., "Soluble Ligands of the alphavbeta3 Integrin Mediate Enhanced Tyrosine Phosphorylation of Multiple Proteins in Adherent Bovine Pulmonary Artery Endothelial Cells," The Journal of Biological Chemistry 270(28):16781–16787.

* cited by examiner

*Primary Examiner*—Michael Borin
(74) *Attorney, Agent, or Firm*—Fulbright & Jaworski L.L.P.

(57) ABSTRACT

The amino acid sequence of native contortrostatin was used in a cloning strategy to obtain full-length cDNA and deduced amino acid sequences for a contortrostatin precursor. The precursor includes pro-protein, metalloproteinase, and disintegrin (contortrostatin) regions of the multidomain protein. The sequences can be used produce recombinant DNA molecules which code on expression for contortrostatin proteins, including biologically active variants and fragments. When formulated as a pharmaceutically acceptable composition, the proteins can be used to treat patients by inhibiting disease processes associated with an integrin binding to an integrin receptor.

15 Claims, 24 Drawing Sheets

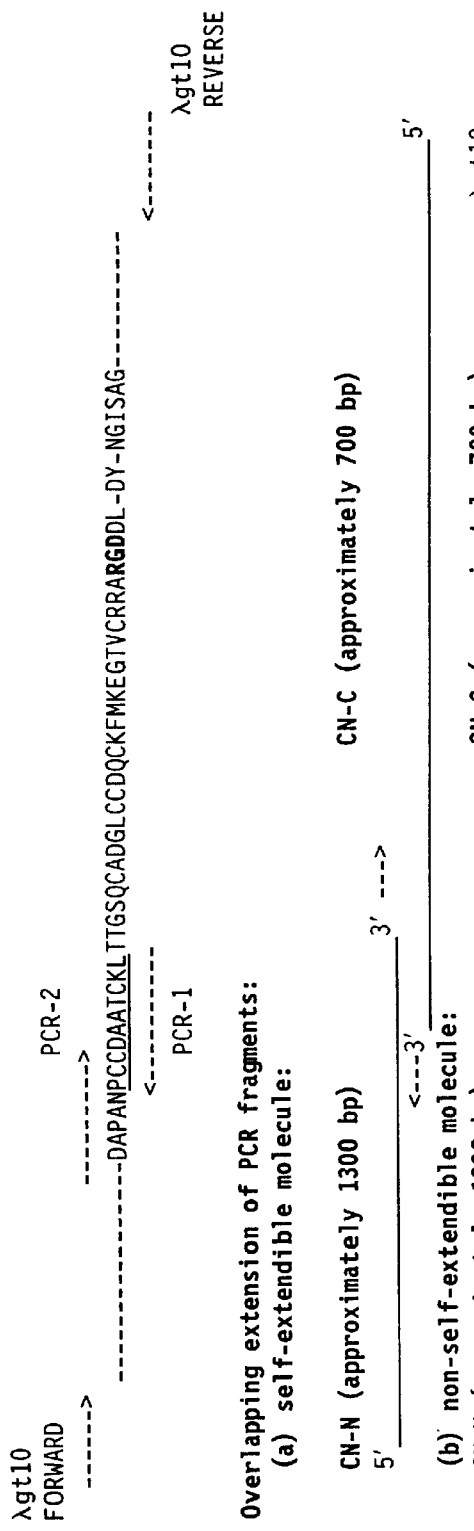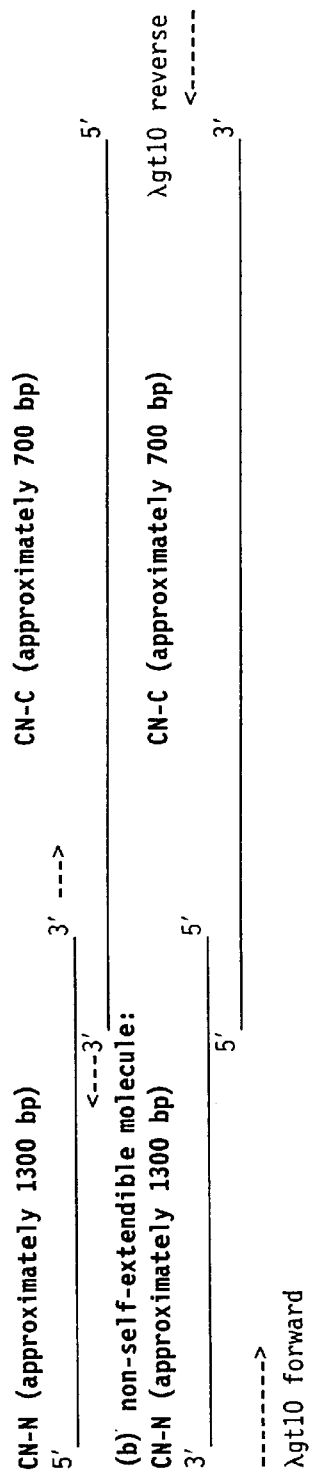
FIG. 1

FIG. 3A

```
                  11           20           29           38           47           56
5' GA ATT CGG GGT CAA TAG AGG AAG AGC TCA AGT TGG CTT GAA AGC AGG AAG AGA TTG 65           74           83           92          101          110
    CCT GTC TTC CAG CCA AAT CCA GCC GCC AAA ATG ATC CAG GTT CTC TTG GT6 ACT
                                            --- --- --- --- --- --- ---
[1]                                          M   I   Q   V   L   L   V  [8]

119          128          137          146          155          164
    CTA TGC TTA GCA GCT TTT CCT TAT CAA GGG AGC TCT ATA ATC CTG GAA TCT GGG
    --- --- --- --- --- --- --- --- --- --- --- --- --- --- --- --- --- ---
[9]  L   C   L   A   A   F   P   Y   Q   G   S   S   I   I   L   E   S   G  [26]

173          182          191          200          209          218
    AAT GTT AAT GAT TAT GAA GTA CTG TAT CCA CAA AAA GTC ACT GCA TTG CCC AAA
    --- --- --- --- --- --- --- --- --- --- --- --- --- --- --- --- --- ---
[27] N   V   N   D   Y   E   V   L   Y   P   Q   K   V   T   A   L   P   K  [44]

227          236          245          254          263          272
    GGA GCA GTT CAG CCA AAG TAT GAA GAC ACC ATG CAA TAT GAA TTT AAA GTG AAT
    --- --- --- --- --- --- --- --- --- --- --- --- --- --- --- --- --- ---
[45] G   A   V   Q   P   K   Y   E   D   T   M   Q   Y   E   F   K   V   N  [62]

281          290          299          308          317          326
    GGA GAG CCA GTG GTC CTT CAC CTG GAA AAA AAT AAA GGA CTT TTT TCA AAA GAT
    --- --- --- --- --- --- --- --- --- --- --- --- --- --- --- --- --- ---
[63] G   E   P   V   V   L   H   L   E   K   N   K   G   L   F   S   K   D  [80]

335          344          353          362          371          380
    TAC AGC GAG ACT CAT TAT TCC TCT GAT GGC AGA AAA ATT ACA ACA AAC CCT CCG
    --- --- --- --- --- --- --- --- --- --- --- --- --- --- --- --- --- ---
[81] Y   S   E   T   H   Y   S   S   D   G   R   K   I   T   T   N   P   P  [98]

389          398          407          416          425          434
    GTT GAG GAT CAC TGC TAT TAT CAT GGA CGC ATC CAG AAT GAT GCT GAC TCA ACT
    --- --- --- --- --- --- --- --- --- --- --- --- --- --- --- --- --- ---
[99] V   E   D   H   C   Y   Y   H   G   R   I   Q   N   D   A   D   S   T  [116]

443          452          461          470          479          488
    GCA AGC ATC AGT GCA TGC AAC GGT TTG AAA GGA CAT TTC AAG CTT CAA GGG GAG
    --- --- --- --- --- --- --- --- --- --- --- --- --- --- --- --- --- ---
[117]A   S   I   S   A   C   N   G   L   K   G   H   F   K   L   Q   G   E  [134]

497          506          515          524          533          542
    ACG TAC CTT ATT GAA CCC TTG AAG CTT TCC GAC AGT GAA GCC CAT GCA GTC TAC
    --- --- --- --- --- --- --- --- --- --- --- --- --- --- --- --- --- ---
[135]T   Y   L   I   E   P   L   K   L   S   D   S   E   A   H   A   V   Y  [152]

551          560          569          578          587          596
    AAA TAT GAA AAC GTA GAA AAA GAA GAT GAG GCC CCC AAA ATG TGT GGG GTA ACC
    --- --- --- --- --- --- --- --- --- --- --- --- --- --- --- --- --- ---
[153]K   Y   E   N   V   E   K   E   D   E   A   P   K   M   C   G   V   T  [170]
```

FIG. 3B

```
             605             614             623             632             641             650
        CAG ACT AAT TGG GAA TCA GAT GAG CCC ATC AAA AAG GCC TCT CAG TTA AAT CTT
        --- --- --- --- --- --- --- --- --- --- --- --- --- --- --- --- --- ---
   [171]Q   T   N   W   E   S   D   E   P   I   K   K   A   S   Q   L   N   L [188]

659             668             677             686             695             704
        ACT CCT GAA CAA CAA GGA TTC CCC CAA AGA TAC ATT GAG CTT GTT GTA GTT GCA
        --- --- --- --- --- --- --- --- --- --- --- --- --- --- --- --- --- ---
   [189]T   P   E   Q   Q   G   F   P   Q   R   Y   I   E   L   V   V   V   A [206]

713             722             731             740             749             758
        GAT CAC AGA ATG TTC ACG AAA TAC AAC GGC AAT TTA AAT ACT ATT AGA ATA TGG
        --- --- --- --- --- --- --- --- --- --- --- --- --- --- --- --- --- ---
   [207]D   H   R   M   F   T   K   Y   N   G   N   L   N   T   I   R   I   W [224]

767             776             785             794             803             812
        GTA CAT GAA CTT GTC AAC ACT ATG AAT GTG TTT TAC AGA CCT TTG AAT ATT CGT
        --- --- --- --- --- --- --- --- --- --- --- --- --- --- --- --- --- ---
   [225]V   H   E   L   V   N   T   M   N   V   F   Y   R   P   L   N   I   R [242]

821             830             839             848             857             866
        GTC TCA CTG ACT GAC CTA GAA GTT TGG TCA GAC CAA GAT TTG ATC AAC GTG CAG
        --- --- --- --- --- --- --- --- --- --- --- --- --- --- --- --- --- ---
   [243]V   S   L   T   D   L   E   V   W   S   D   Q   D   L   I   N   V   Q [260]

875             884             893             902             911             920
        CCA GCA GCG GCT GAT ACT TTG GAA GCA TTT GGA GAC TGG AGA GAG ACA GTC TTG
        --- --- --- --- --- --- --- --- --- --- --- --- --- --- --- --- --- ---
   [261]P   A   A   A   D   T   L   E   A   F   G   D   W   R   E   T   V   L [278]

929             938             947             956             965             974
        CTG AAT CGC ATA AGT CAT GAT AAT GCT CAG TTA CTC ACG GCC ATT GAG CTT GAT
        --- --- --- --- --- --- --- --- --- --- --- --- --- --- --- --- --- ---
   [279]L   N   R   I   S   H   D   N   A   Q   L   L   T   A   I   E   L   D [296]

983             992            1001            1010            1019            1028
        GGA GAA ACT ATA GGA TTG GCT AAC AGG GGC ACC ATG TGC GAC CCG AAG CTT TCT
        --- --- --- --- --- --- --- --- --- --- --- --- --- --- --- --- --- ---
   [297]G   E   T   I   G   L   A   N   R   G   T   M   C   D   P   K   L   S [314]

1037            1046            1055            1064            1073            1082
        ACA GGA ATT GTT CAG GAT CAT AGT GCA ATA AAT CTT TGG GTT GCA GTT ACA ATG
        --- --- --- --- --- --- --- --- --- --- --- --- --- --- --- --- --- ---
   [315]T   G   I   V   Q   D   H   S   A   I   N   L   W   V   A   V   T   M [332]

1091            1100            1109            1118            1127            1136
        GCC CAT GAG ATG GGT CAT AAT CTG GGT ATT AGT CAC GAT GGA AAT CAG TGT CAT
        --- --- --- --- --- --- --- --- --- --- --- --- --- --- --- --- --- ---
   [333]A   H   E   M   G   H   N   L   G   I   S   H   D   G   N   Q   C   H [350]

1145            1154            1163            1172            1181            1190
        TGC GAT GCT AAC TCA TGC ATT ATG AGT GAA GAA CTA AGA GAA CAA CTT TCC TTT
        --- --- --- --- --- --- --- --- --- --- --- --- --- --- --- --- --- ---
   [351]C   D   A   N   S   C   I   M   S   E   E   L   R   E   Q   L   S   F [368]
```

FIG. 3C

```
             1199        1208        1217        1226        1235        1244
       GAG TTC AGC GAT TGT AGT CAG AAT CAA TAT CAG ACA TAT CTT ACT GAT CAT AAC
       --- --- --- --- --- --- --- --- --- --- --- --- --- --- --- --- --- ---
[369]E  F   S   D   C   S   Q   N   Q   Y   Q   T   Y   L   T   D   H   N [386]

1253        1262        1271        1280        1289        1298
       CCA CAA TGC ATG CTC AAT GAA CCC TTG AGA ACA GAT ATT GTT TCA ACT CCA GTT
       --- --- --- --- --- --- --- --- --- --- --- --- --- --- --- --- --- ---
[387]P  Q   C   M   L   N   E   P   L   R   T   D   I   V   S   T   P   V [404]

1307        1316        1325        1334        1343        1352
       TCT GGA AAT GAA CTT TTG GAG ACG GGA GAA GAA AGT GAC TTT GAC GCT CCT GCA
       --- --- --- --- --- --- --- --- --- --- --- --- --- --- --- --- --- ---
[405]S  G   N   E   L   L   E   T   G   E   E   S   D   F   D   A   P   A [422]

1361        1370        1379        1388        1397        1406
       AAT CCG TGC TGC GAT GCT GCA ACA TGT AAA CTG ACA ACA GGG TCA CAG TGT GCA
       --- --- --- --- --- --- --- --- --- --- --- --- --- --- --- --- --- ---
[423]N  P   C   C   D   A   A   T   C   K   L   T   T   G   S   Q   C   A [440]

1415        1424        1433        1442        1451        1460
       GAT GGA CTG TGT TGT GAC CAG TGC AAA TTT ATG AAA GAA GGA ACA GTA TGC CGG
       --- --- --- --- --- --- --- --- --- --- --- --- --- --- --- --- --- ---
[441]D  G   L   C   C   D   Q   C   K   F   M   K   E   G   T   V   C   R [458]

1469        1478        1487        1496        1505        1514
       AGA GCA AGG GGT GAT GAC CTG GAT GAT TAC TGC AAT GGC ATA TCT GCT GGC TGT
       --- --- --- --- --- --- --- --- --- --- --- --- --- --- --- --- --- ---
[459]R  A   R   G   D   D   L   D   D   Y   C   N   G   I   S   A   G   C [476]

1523        1532        1541        1550        1559        1568
       CCC AGA AAT CCC TTC CAT GCC TAA CCA ACA ATG GAG ATG GAA TGG TCT GCA GCA
       --- --- --- --- --- --- --- ---
[477]P  R   N   P   F   H   A   * [483]

1577        1586        1595        1604        1613        1622
       ACA GGC AGT GTG TTG ATC TGA ATA CAG CCT AAT AAT CAA CCT CTG GCT TCT CTC 1631        1640        1649        1658        1667        1676
       AGA TTT GAT CAT GGA GAT CCT TCT TCC AGA AGG TTT CAC TTC CCT CAA ATC CAA 1685        1694        1703        1712        1721        1730
       AGA GAC CCA TCT GCC TGC ATC CTA CTA GTA AAT CAC CCT TAG CTT CCA GAT GGT 1739        1748        1757        1766        1775        1784
       ATC CAA ATT CTG TAA TAT TTC TTC TCC ATA TTT AAT CTA TTT ACC TTT TGC TGT 1793        1802        1811        1820        1829        1838
       AAC AAA ACC TTT TTC CTG TCA CAA AGC TCC ATG GGC ATG TAC AGC TTA TCT GCT 1847        1856        1865        1874        1883        1892
       GTC AAG AAA AAA AAT GGC CAT TTT ACC GTT TGC CAG TTA CAA AGC ACA TTT AAT 1901        1910        1919        1928        1937        1946
       GCA ACA AGT TCT TCC TTT TGA GCT GAT GTA TTC AAA GTC AAT GCT TCC TCT CCC
```

FIG. 3D

```
        1955            1964            1973            1982            1991            2000
    AAA ATT TCA TGC TGG CTT CCC AAG ATG TAG CTG CTT CCG TCA ATA AAC AAA CTA 2009            2018            2027
    TTC TCA TTC AAA AAA AAA AAC CCG AAT TC 3'
```

FIG. 4-1

Proprotein domain:

```
             1         10        20        30        40        50
             *         *         *         *         *         *
CN           MIQVLLVTLCLAAFPYQGSSIILESGNVNDYEVLYPQKVTALPKGAVQPKY
Trigramin    MIQVLLITICLAVFPYQGSSIILESGNLNDYEVVYPEKVTALPKGAVQQKY
Cat          MIQVLLVTICLAAFPYQGSSIILESGNVNDYEVIYPRKVTALPKGAVQPKY
Jararhagin                                         ATRPKGAVQPKY
Ht-e         MIQVLLVTICLAAFPYQGSSIILESGNVNDYEVIYPRKVTALPKGAVQPKY
                       110       120       130       140       150
                       *         *         *         *         *
CN           DHCYYHGRIQNDADSTASISACNGLKGHFKLQGETYLIEPLKLSDSEAHAV
Trigramin    DHCYYHGRIENDADSTASISACDGLKGHFKLQGEMYLIEPLELSDSEAHAV
Cat          DHCYYHGRIENDADSTASISACNGLKGHFKLQGEMYLIEPLKLPDSEAHAV
Jararhagin   DHCYYHGRIENDADSTASISACNGLKGYFKLQRETYFIEPLKLPDSEAHAV
Ht-e         DHCYYHGRIENDADSTASISACNGLKGHFKLQGEMYLIEPLKLSDSEAHAV
```

Metalloproteinase domain:

```
                       200       210       220       230       240
                       *         *         *         *         *
CN           EQQGF.PQRYIELVVVADHRMFTKYNGNLNTIRIWVHELVNTMNVFYRPLN
Trigramin    EQQRF.PQRYIKLGIFVDHGMYTKYSGNSERITKRVHQMINNINMMCRALN
Cat          EHQKYNPFRFVELFLVVDKAMVTKNNGDLDKIKTRMYEIVNTVNEIYRYMY
Jararhagin   EQQRYDPYKYIEFFVVVDQGTVTKNNGDLDKIKARMYELANIVNEIFRYLY
Ht-e         EHQ.....RYVELFIVVDHGMYTKYNGDSDKIRQRVHQMVNIMKESYTYMY
             290       300       310       320       330       340
             *         *         *         *         *         *
CN           LTAIELDGETIGLANRGTMCDPKLSTGIVQDHSAINLWVAVTMAHEMGHNL
Trigramin    LTATIFNGNVIGRAPVGGMCDPKRSVAIVRDHNAIVFVVAVTMTHEMGHNL
Cat          LTAIDL.DRVIGLAYVGSMCHPKRSTGIIQDYSEINLVVAVIMAHEMGHNL
Jarahagin    LTAIDFNGPTIGYAYIGSMCHPKRSVGIVQDYSPINLVVAVIMAHEMGHNL
Ht-e         LTSIAFDEQIIGRAYIGGICDPKRSTGVVQDHSEINLRVAVTMTHELGHNL
```

Disintegrin domain:

```
                       420       430       440       450
                       *         *         *         *
CN           ETGEESDF---DAĎABŎCCDAATCJKTTGSQCADGKCCDQCJFNJEGTVCR
Trigramin    EAGEDCDCGSPA...NPCCDAATCKLIPGAQCGEGLCCDQCSFIEEGTVCR
Cat          EVGEECDCGTPENCQNECCDAATCKLKSGSQCGHGDCCEQCKFSKSGTECR
Jararhagin   EVGEECDCGTPENCQNECCDAATCKLKSGSQCGHGDCCEQCKFSKSGTECR
Ht-e         EAGIECDGGSLE...NPCCYATTCKMRPGSQCAEGLCCDQCRFMKKGTVCR
```

C-terminal domain:

```
                       490       500       510       520       530
                       *         *         *         *         *
Cat          NGQPCLDNYGYCYNGNCPIMYHQCYDLFGADVYEAEDSCFERNQKGNYYGY
Jararhagin   NGQPCLDNYGYCYNGNCPIMYHQCYALFGADVYEAEDSCFKDNQKGNYYGY
                       590       600
                       *         *
Cat          PGTKCADGKVCSNGHCVDVATAY*
Jararhagin   PGTKCADGKVCSNGHCVDVATAY
```

FIG. 4-2

```
              60         70         80         90        100
               *          *          *          *          *
     EDTMQYEFKVNGEPVVLHLEKNKGLFSKDYSETHYSSDGRKITTNPPVE
     EDAMQYEFKVNGEPVVLHLEKNKGLFSEDYSEIHYSPDGREITAYPSVE
     EDAMQYELKVNGEPVVLHLGKNKGLFSKDYSETHYSPDGREITTYPLVE
     EDAMQYEFKVNGEPVVLHLEKNKGLFSKDYSEIHYSPDGREITTYPPVE
     EDTMQYELKVNGEPVVLHLEKNKGLFSKDYSETHYSFDGRKITTNPSVE
              160        170        180        190
               *          *          *          *
     YKYENVEKEDEAPKMCGVTQTNWESDEPIKKASQLNLTP
     FKYENVEKEDEPPKMCGVTQ.NWESYESTKKASQLNVTP
     YKYENVEKEDEALKMCGVTQ.NWESYEPIKKASQLVVTA
     FKYENVEKEDEAPKMCGVTQ.NWKSYEPIKKASQLAFTA
     FKLKNVEKEDEAPKMCGVTQ.NWESYEPIKKASDLNLNP 250        260        270        280
               *          *          *          *
     IRVSLTDLEVWSDQDLINVQPAAADTLEAFGD.WRETVLLNRISHDNAQL
     IVTTLSVLEIWSEKDLITVQ.ASAPTTLTLFGAWRETVLLNRTSHDHAQL
     IHVALVGLEIWSNEDKITVKPEAGYTLNA.FGEWRKTDLLTRKKHDNAQL
     MHVALVGLEIWSNGDKITVKPDVDYTLNS.FAEWRKTDLLTRKKHDNAQL
     IDILLAGIEIWSNGDLINVQPASPNTLNS.FGEWRETDLLKRKSHDNAQL
              350        360        370        380        390       400       410
               *          *          *          *          *         *         *
     GISHDGNQCHCDANSCIMSEELREQLSFEFSDCSQNQYQTYLTDHNPQCMLNEPLRTDIVSTPVSGNELL
     GMHHDEDKCNCN..TCIMSKVLSRQPSKYFSECSKDYYQTFLTNHNPQCILNAPLRTDTVSTPVSGNELL
     GINHDSGYCSCGDYACIMRPEISPEPSTFFSNCSYFECWDFIMNHNPECILNEPLGTDIISPPVCGNELL
     GIHHDTGSCSCGDYPCIMGPTISNEPSKFFSNCSYIQCWDFIMNHNPECIINEPLGTDIISPPVCGNELL
     GIHHDTDSCSCGGYSCIMSPVISDEPSKYFSDCSYIQCWEFIMNQKPQCILKKPLRTDTVSTPVSGNELL 460        470        480
      *          *          *
     RARGD.DLDDYCNGISAGCPRNPFHA*
     IARGD.DLDDYCNGRSAGCPRNPFHA
     ASMSECDPAEHCTGQSSECPADVFHK
     ASMSECDPAEHCTGQSSECPADVFHK
     VSMVDRN.DDTCTGQSADCPRNGLYG*

540        550        560        570        580
               *          *          *          *          *
     CRKENGNKIPCAPEDVKCGRLYCKDNSPGQNNPCKMFYSNEDEHKGMVL
     CRKENGKKIPCAPEDVKCGRLYCKDNSPGQNNPCKMFYSNDDEHKGMVL
```

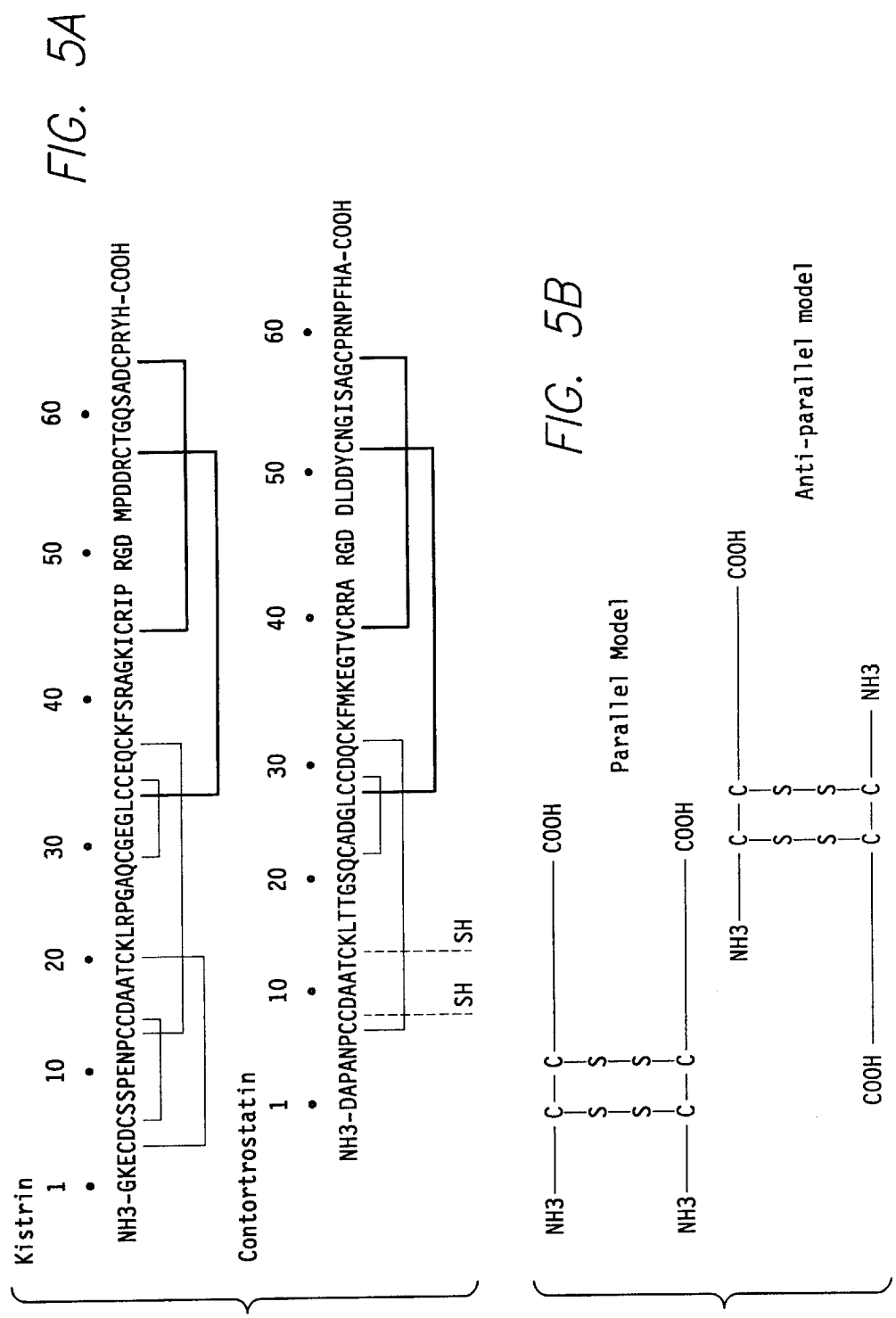

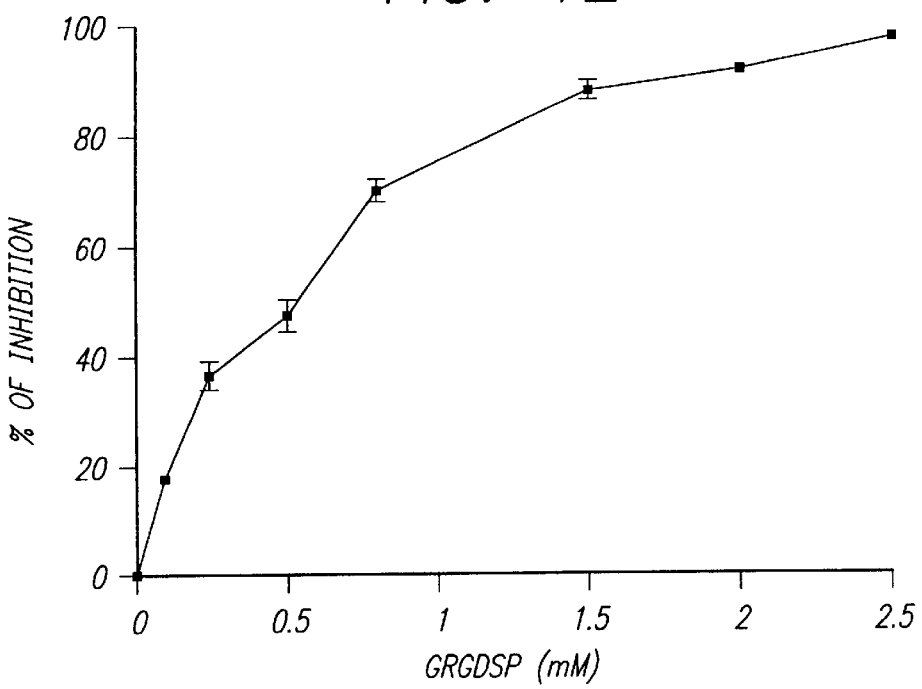
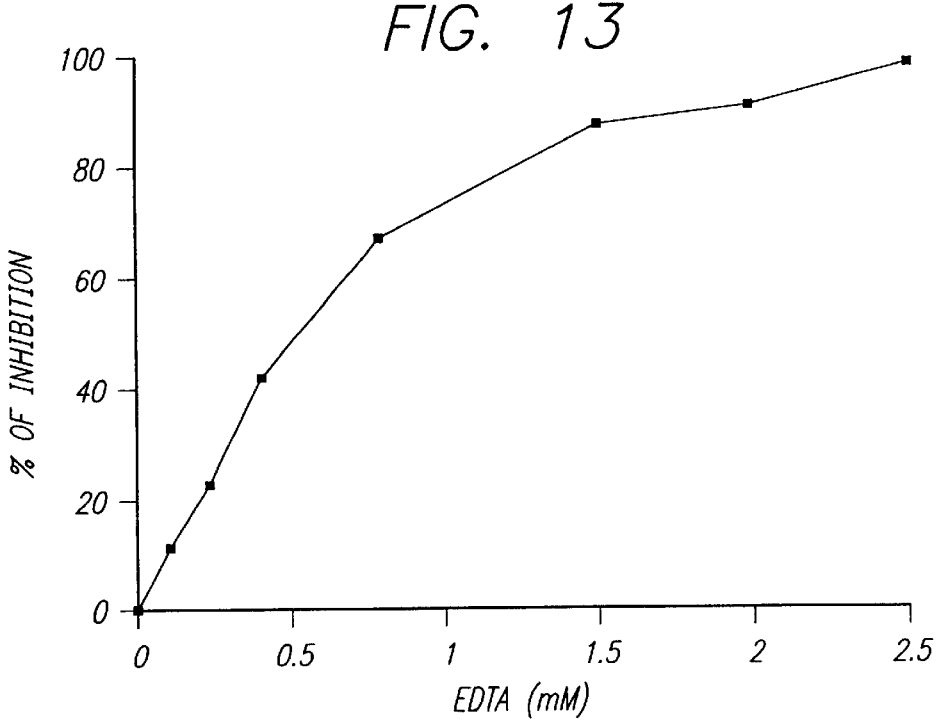

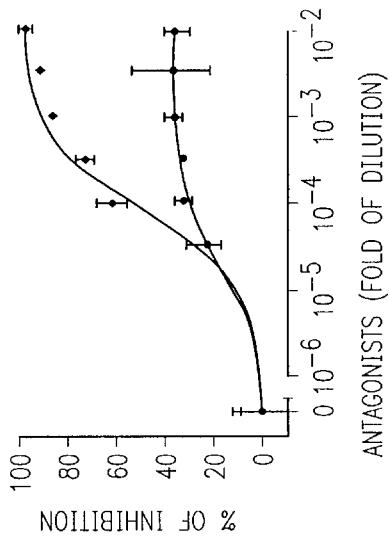

FIG. 24
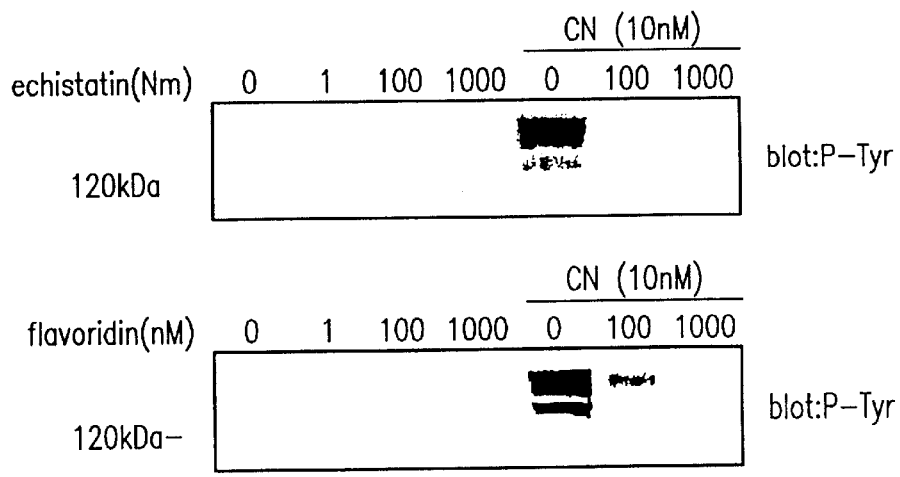
FIG. 25
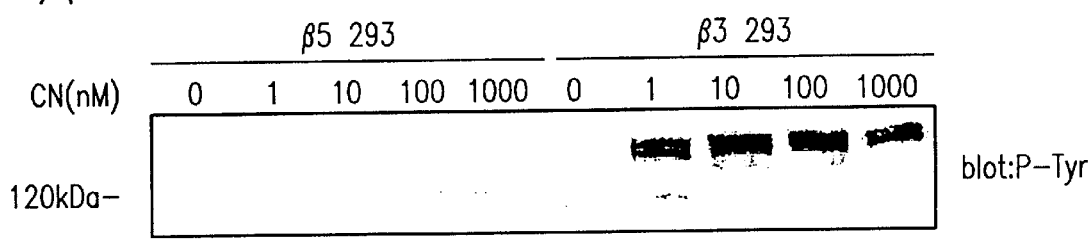
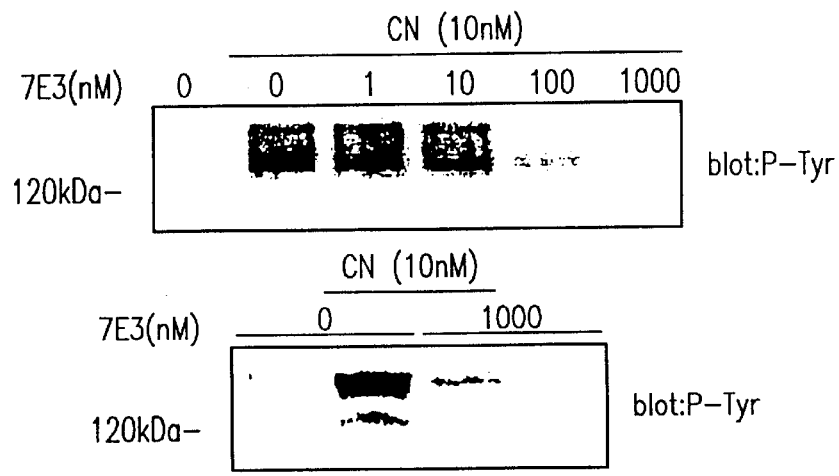

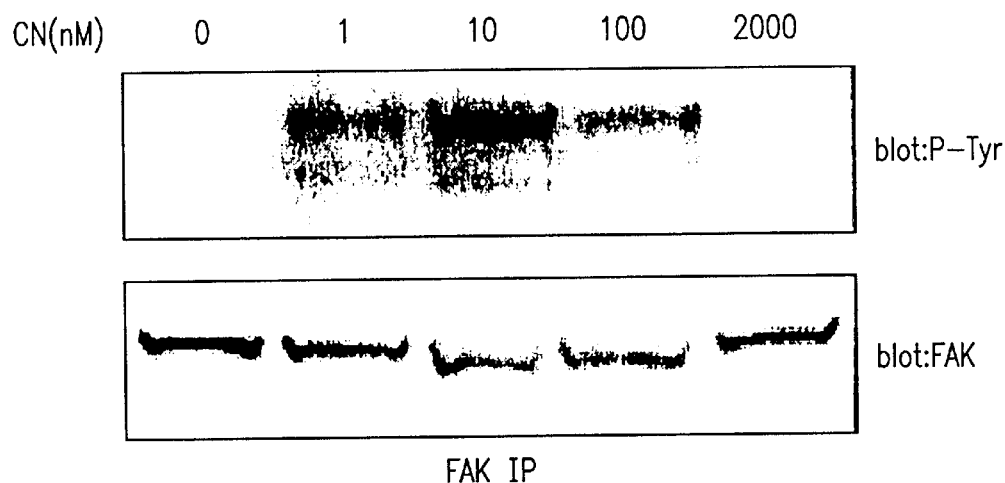
FAK IP
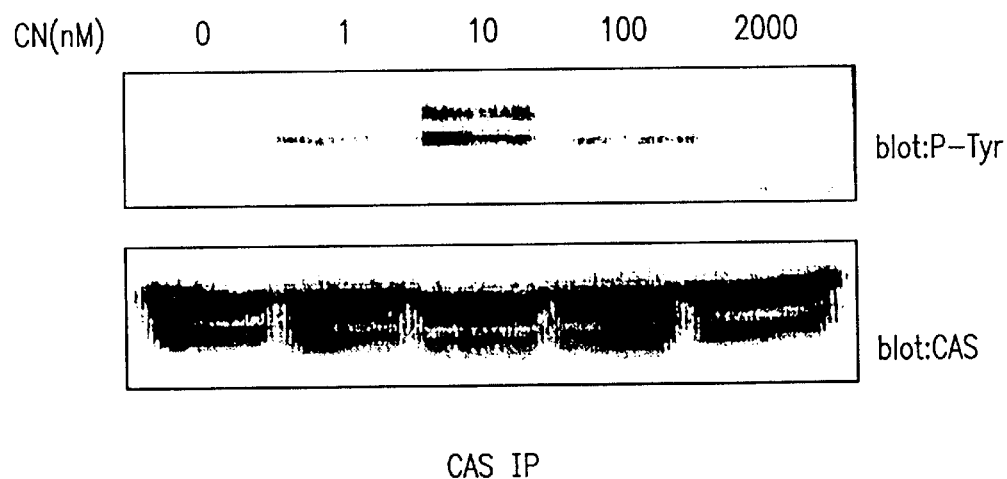
CAS IP
FIG. 26

CONTORTROSTAIN (CN) AND METHODS FOR ITS USE IN PREVENTING METASTASIS AND OTHER CONDITIONS

RELATED APPLICATIONS

This application is a continuation-in-part of U.S. Ser. No. 09/163,047, filed Sep. 29, 1998 now abandoned, which is a continuation-in-part of U.S. Ser. No. 08/745,603, filed Nov. 8, 1996, which issued as U.S. Pat. No. 5,814,609 on Sep. 29, 1998, which is a continuation-in-part of U.S. Ser. No. 08/632,691, filed Apr. 15, 1996, which issued as U.S. Pat. No. 5,731,288 on Mar. 24, 1998, which is a division of application Ser. No. 08/540,423, filed Oct. 10, 1995, now abandoned, which is a continuation of application Ser. No. 08/141,321 filed Oct. 22, 1993, now abandoned.

FIELD OF THE INVENTION

The present invention relates generally to the field of biochemistry and medicine and in particular to the cloning, sequencing, and production of contortrostatin and its precursor.

BACKGROUND OF THE INVENTION

Breast cancer is one of the leading causes of death among non-smoking women and the spread of the disease from the breast to distant sites is a major cause of death in breast cancer patients. At the time of diagnosis over 60% of breast cancer patients will have disease that has spread from the primary site in the breast to some distant site. Spread of cancer to remove sites, e.g. bone, lungs, liver, brain, a process called metastasis, is a characteristic of malignancy and often leads to inoperable disease. Metastasis is the most common factor leading to death from breast cancer. Control of metastasis offers an important avenue for breast cancer treatment. Cancer cells metastasize through the blood or lymph vessels. The first step of metastasis involves the attachment of cancer cells to tissues around the primary site, i.e., to the extracellular matrix (ECM) via cell surface integrins and other adhesion receptors. Integrins mediate cell—cell and cell-substratum interactions and are involved in bi-directional signaling that links the ECM with cytoskeletal proteins. Integrins play an important role in the interaction of mammary carcinoma cells with the ECM. In the second step, cancer cells secrete digestive enzymes that degrade the surrounding tissues allowing the tumor cells to invade these tissues. Eventually, the tumor cells enter the blood or lymphatic system where they repeat the adhesion and invasion steps at a distant (metastatic) site. At this remote site, tumor cells induce the formation of new blood vessels (a process called neovascularization), in and around the growing tumor. These new blood vessels supply nutrients to the metastatic tumor and allow it to grow. Treatments that block any of these steps should act to inhibit metastasis.

Integrins on cancer cells play important roles in tumor invasion and spread. They are a family of proteins found on the cell surface of many cell types that mediate interactions between cells, and between cells and their surroundings. Integrins are heterodimers, composed of α and β subunits involved in cell—cell and cell-substratum interactions. Integrins serve as receptors for extracellular matrix proteins such as fibronectin, fibrinogen, vitronectin, collagen and laminen. Some of these interactions have been shown to be mediated via an Arg-Gly-Asp (RGD) sequence present in the matrix proteins. Both the α and β subunits are required for fibrinogen binding. For example, one of the members of the superfamily of integrin cell surface receptors is the platelet membrane glycoprotein (GP)IIb/IIIa which interacts with plasma fibrinogen in platelet aggregation.

CN binds to a specific integrin on the surface of blood platelets, and blocks the ability of platelets to adhere to one another (a process called platelet aggregation). Platelets are small fragments of bone marrow cells that are found in the blood stream. They have both beneficial and harmful activities. Their useful action is to stop bleeding following injury by facilitating the formation of a blood clot. But, under certain conditions they are involved in blocking arteries that supply nourishment to the heart—an action that can lead to a heart attack.

Integrin cell surface receptors have been investigated in the role of platelets in mediating coronary artery thrombosis and rethrombosis in the genesis of acute myocardial infarction [Zucker, M. B., *Sci. American* 242:86 (1990)]. For platelet aggregation an RGD sequence present in fibrinogen is essential for the interaction with (GP)IIb/IIIa [Ginsberg, M. H. et al., *Thrombos. Haemostas.* 59:1 (1988)]. Because of its inhibition of platelet aggregation, snake venom has been the subject of various investigations.

A number of proteins purified from venom of snakes of the Crotalidae and Viperidae families have been found to inhibit glycoprotein (GP)IIb/IIIa mediated platelet aggregation [see, e.g., Huang, T. F. et al., *J. Biol. Chem.* 262:16157 (1987); Gan, Z. R. et al., *J. Biol. Chem.* 263:19827 (1988); Yasuda, T. et al., *J. Am. Coll. Cardiol.* 16:714 (1990); Trikha, M. et al., *Fibrinolysis* 4 (Suppl. 1):105 (1990); Trikha, M. et al., *Blood* 76 (Suppl. 1):479a (1990); Holahan, M. A. et al., *Pharmacology* 42:340 (1991); Shebuski, R. J. et al., *Circulation* 82:169 (1990); Yasuda, T. et al., *Circulation* 83:1038 (1991)]. These proteins, classified as disintegrins, are typically disulfide rich. Moreover, all disintegrins isolated thus far, with the exception of barbourin [Scarborough, R. M. et al., *J. Biol. Chem.* 266:9359 (1991)] contain an RGD (Arg-Gly-Asp) sequence that has been implicated as being involved in the inhibition of integrin-mediated interactions. In particular, the RGD sequence of the disintegrins may compete for fibrinogen binding sites on the platelet membrane, thereby inhibiting platelet aggregation induced by ADP or other agents.

Nonetheless, there appears to be increasing evidence that disintegrins may have unique surface geometry which facilitates interactions with integrins by mechanisms other than those based solely upon the RGD site. For example, the finding that a mutated, chemically synthesized derivative of echistatin (in which alanine was substituted for arginine in the RGD sequence) still possessed some biological activity, suggests that other regions in the protein may be involved in binding and that there may be some flexibility in the RGD binding site [Connolly, T. M. et al., *Circulation* 82 (Suppl. III):660 (1990)]. Synthetic RGD peptides, due to their small size, generally do not possess the molecular topography of the disintegrins and therefore cannot interact via the multiplicity of mechanisms likely to be involved in disintegrin binding.

In other investigations, prevention of reocclusion following thrombolysis using tissue-type plasminogen activator in a canine model system has been reported using 30 μg/kg plus 3 μg/kg/min bitistatin, an 83 amino acid disintegrin derived from the venom of *Bitis arietans* [Shebuski et al., supra], or 15 μg/kg/min i.v. echistatin, a 49 amino acid disintegrin derived from the venom of *Echis carinatus* [Holahan et al., supra]. In the reported methods, an initial bolus of heparin (100 U/kg i.v.) and subsequent hourly boluses of 50 U/kg were used to increase activated partial thromboplastin times at least 1.5-fold over the control. Whereas it had previously been observed that heparin in combination with tissue-type plasminogen activator (tPA) did not affect the incidence of acute reocclusion in this model system, the addition of echistatin or bitistatin lead to dramatic reductions in the incidence of acute thrombotic reocclusion. The administration of heparin was, however, apparently necessary for prevention of acute thrombotic reocclusion.

Similarly, kistrin (a 68 amino acid disintegrin derived from the venom of *Agkistrodon rhodostoma*) was evaluated in conjunction with recombinant tissue-type plasminogen activator in a canine model of coronary artery thrombosis with superimposed high grade stenosis [Yasuda et al. (1991), supra]. An effective dose of 4 µg/kg/min was determined to be sufficient to prevent reocclusion. Simultaneous systemic therapeutic heparin anticoagulation was used; the dose of heparin was selected to maintain the activated partial thromboplastin time more than two-fold throughout the experimental observation period.

U.S. Pat. No. 5,066,592 to Huang et al. describes the use of trigramin, a 72 amino acid disintegrin isolated from the venom of *Trimeresurus gramineus*, to inhibit fibrinogen binding to human platelets and thereby to inhibit fibrinogen-induced aggregation of human platelets. Trigramin is also reported to inhibit binding of von Willebrand factor to platelets. Trigramin is reported to inhibit $^{125}$I-fibrinogen binding to ADP (10 µmolar)-stimulated platelets in a concentration-dependent manner with an $IC_{50}$ of 2.8–5.6× $10^{-8}$M.

Isolation of an anti-platelet factor applaggin from the venom of *Agkistrodon piscivorus piscivorus* has also been reported [Chao, B. H. et al., *Proc. Natl. Acad. Sci. USA* 86:8050 (1989); Savage, B. et al., *J. Biol. Chem.* 265:11766 (1990)]. Applaggin, unlike trigramin, is reported to inhibit dense-granule secretion in concert with inhibition of platelet aggregation in a dose-dependent manner. While initially described as a homodimer with at least two interchain disulfide bridges [Chao et al. (1989), supra], a subsequent report indicated that analysis of purified applaggin by mass spectroscopy showed the presence of applaggin monomers with a mass of 7,666 Daltons and no evidence of dimerization [Wencel-Drake, J. D. et al., *Blood* 81:62 (1993)].

One disintegrin of particular interest is CN, which has been isolated from the venom of *Agkistrodon contortrix contortrix* (the southern copperhead snake). The originally-reported purification procedure included molecular sieve chromatography on Sephadex G-100 SF, desalting on Sephadex G-25F and reverse phase HPLC. ADP-enhanced aggregation of stirred human platelet rich plasma and the inhibition thereof by CN were monitored at 37° C. It was found that preincubation for 1 minute of the platelet rich plasma (3×10$^5$/mm$^3$) with 5 µl of the low molecular weight peak after Sephadex G-100 SF resulted in 76% inhibition of platelet aggregation induced by 10 µM ADP [Trikha et al. (1990), supra].

In a subsequent report it was noted that in crude venom, the inhibitor was not readily detectable due to the presence of platelet aggregating activity; however, following the first step of purification (hydrophobic interaction HPLC) inhibitory activity was separated from both aggregating activity and an α-chain degrading fibrinolytic enzyme present in the venom. Inhibitory activity was pooled following HPLC and applied to a hydroxylapatite HPLC column. In the final step of purification, C$_4$ reverse phase HPLC chromatography was employed. The yield of the homogeneous protein was 3–5 mg per gram of venom. CN was reported to have a molecular weight of 18–21 kDa under non-reducing conditions and 9 kDa under reducing conditions; thus, the molecule was believed to be a homodimer with the two subunits being held together by disulfide bond(s). Isoelectric focusing showed that the protein had an acidic pI. CN was reported not to exhibit fibrinolytic activity and was not a 5'-nucleotidase or a phospholipase based on molecular size and kinetics of inhibition of platelet aggregation. Following preincubation for 1 minute, CN at approximately 100 nM was reported to completely inhibit ADP-induced platelet aggregation [Trikha et al. (1990), supra].

It has further been reported that CN has 70 amino acids with five to six disulfide bridges, and that the sequence of CN appears to begin 10 amino acids downstream of applaggin (a platelet aggregation inhibitor from the venom of *Agkistrodon piscivorus piscivorus*). It was speculated that CN may have an insertion and/or a C-terminal extension of nine amino acids. It was further reported that a 50% inhibition ($IC_{50}$) of human platelet aggregation in platelet rich plasma was observed at 0.8 µg/ml of CN, and at 2.2 µg/ml with canine platelets [Trikha, M. et al., *Journal of Cellular Biochem.* 16F:180 (1992)].

CN was reported to inhibit binding of human fibrosarcoma (HT-1080) and c-Ha-ras transfected rat embryo (4R) cells to fibronectin coated plates but not to matrigel coated plates. Inhibition of 4R cell binding to fibronectin in the presence of CN at 1 µg/ml and 5 µg/ml was 46% and 88%, respectively, and for HT1080 cells inhibition was 89% and 85%, respectively [Trikha, M. et al., *Proceedings of the American Association for Cancer Research* 33:34 (1992)].

Since it appears that CN can inhibit interactions between integrins and their receptors, and may prove useful in the management of diseases associated with these interactions, there exists a need for improved methods to produce greater amounts of purified contortrostatin, substantially free other snake venom components.

SUMMARY OF THE INVENTION

The present invention fulfills the need for greater amounts of contortrostatin, which can be used to inhibit biological processes such as platelet aggregation, cell growth, adhesion, metastasis, and neovascularization. Native contortrostatin has been purified and a partial amino acid was determined by Edman degradation. This information enabled a cDNA cloning strategy, which resulted in a full-length cDNA sequence and a deduced amino acid sequence for a contortrostatin pre-cursor protein. The contortrostatin precursor includes a pro-protein region, a metalloproteinase region, and a disintegrin region. The metalloproteinase region includes a metal-binding motif and the disintegrin region includes an RGD loop, which can act as an integrin antagonist. Sequences for native contortrostatin are contained in the distintegrin region.

The present invention includes purified contortrostatin proteins, including the contortrostatin precursor, biologically active variants, and fragments thereof. The contortrostatin protein preferably includes an amino acid sequence that matches native contortrostatin monomer (amino acid numbers 419 to 483 of SEQ ID NO: 2), the metalloproteinase region (amino acid numbers 191 to 410 of SEQ ID NO: 2), the pro-protein region (amino acid numbers 1 to 190 of SEQ ID NO: 2) or the contortrostatin precursor as a whole (SEQ ID NO: 2). A most preferred purified protein is comprised of contortrostatin monomers, each having a molecular mass of about 5 to about 7 kDa, which form a homodimer.

A purified contortrostatin, which can act as an integrin antagonist generally will include in each monomer a constrained Arg-Gly-Asp (RGD) sequence at the tip of a flexible peptide loop of about 13 amino acid residues flanked by two Cys residues, such as the amino acid sequence comprising amino acid numbers 457 to 469 of SEQ ID NO: 2.

Biologically active variants, can include amino acid substitutions, deletions, and insertions, but will generally have an amino acid sequence that is at least 90% homologous to the pro-protein, metalloproteinase, disintegrin and/ or contortrostatin regions of the precursor protein. Variants can also include a peptide recognized by an antibody to contortrostatin.

The proteins of the present invention can be made using synthetic methods. The synthetic process can include transcribing and translating a contortrostatin cDNA molecule as disclosed herein, preferably within a transformed host cell. Alternatively, the process involves synthesizing a polypeptide having the amino acid sequence of contortrostatin, as disclosed herein.

Proteins prepared by recombinant DNA methodology will generally include the use of a recombinant DNA molecule comprising a DNA sequence coding on expression for contortrostatin, such as SEQ ID NO:1. Preferably the recombinant DNA molecule encodes sequences having at least one biological activity such as metalloproteinase (e.g. nucleotide numbers 657 to 1316 of SEQ ID NO: 1), or disintegrin (e.g., nucleotide numbers 1341 to 1535 of SEQ ID NO: 1). Moreover, the recombinant DNA molecule can also include pro-protein encoding sequences (e.g., nucleotide numbers 87 to 656 of SEQ ID NO: 1), the entire precursor protein (nucleotide numbers 87 to 1535 of SEQ ID NO: 1), or simply the sequences encoding native contortrostatin monomer (nucleotide numbers 1341 to 1535 of SEQ ID NO: 1).

The present invention further provides a vector, which includes the recombinant DNA molecule, that can be used to transform prokaryotic or eukaryotic host cells. Host cells can be mammalian cells, plant cells, insect cells, yeast and other fungi or bacteria. Processes for producing recombinant contortrostatin will generally include steps, such as culturing the host cell and recovering the contortrostatin expressed by the host cell.

The contortrostatin proteins of the present invention can be formulated as a pharmaceutically acceptable composition, comprising a pharmaceutically acceptable carrier and the purified protein. The pharmaceutical composition can then be used in a method of treating a patient having a disease associated with a ligand binding to an integrin receptor. The treatment generally involves administering the composition to the patient such that integrin binding to integrin receptors is substantially inhibited and the patient is treated. The method of treatment can be used to inhibit platelet aggregation, tumor metastasis, angiogenesis, neovascularization, cell adhesion, invasiveness, or growth.

BRIEF DESCRIPTION OF THE DRAWINGS

The invention may be better understood with reference to the accompanying drawings, which include:

FIG. 1 illustrates the strategy for cloning contortrostatin cDNA, wherein FIG. 1A shows partial amino acid sequence of CN (CN) (amino acids 419 to 475 of SEQ ID NO:2) based on Edman Degradation Assay compared with other disintegrins,namely applaggin (SEQ ID NO:7), Trigramin (amino acids 480 to 551 of SEQ ID NO:8), albolabrin (SEQ ID NO:9), elegantin (SEQ ID NO:10), and kistrin (SEQ ID NO:10), illustrating common RGD sequences and highly conserved sequences, FIG. 1B shows the PCR primers, and FIG. 1C shows the principle of overlapping extension reaction used to generate the full-length cDNA of contortrostatin;

FIG. 3 shows the full-length nucleotide sequence of CN cDNA (SEQ ID NO:1) and the deduced amino acids (SEQ ID NO:2), including an 86 nucleotide 5'-end non-translatable region (NTR), an open reading frame between nucleotides 87 and 1535, a termination codon at nucleotides 1536 to 1538, and a 3'-NTR, which includes an AATAAA site and ends with a poly-A tail;

FIG. 4 shows the multi-domain structure of contortrostatin precursor (SEQ ID NO:2), compared with trigramin precursor (SEQ ID NO:8) and other snake venom hemorrhagic proteins Cat (SEQ ID NO:12), Jararhagin (SEQ ID NO:13) and Ht-E (SEQ ID NO:14);

FIG. 5 illustrates the formation of a contortrostatin homodimer, wherein FIG. 5A shows the amino acid sequence and disulfide bond pattern of the disintegrin kistrin (SEQ ID NO:10) compared to contortrostatin (amino acids 419 to 483 of SEQ ID NO:2), which has a 6-amino-acid truncation at the N-terminus, including two half cystine residues resulting in two cysteine residues being unpaired, and FIG. 5B shows the unpaired cysteines may participate in the formation of two intermolecular disulfide bonds to form a unique homodimeric structure, wherein the two monomers may be linked in a parallel or anti-parallel pattern;

FIG. 12 shows the inhibition of binding of human mammary carcinoma cells to immobilized CN with GRG-DSP (SEQ ID NO:15);

FIG. 13 shows the inhibition of binding of human mammary carcinoma cells to immobilized CN with EDTA;

FIG. 19. Inhibition of adhesion of T24 and T24-β3 neg. cells to vitronectin by different antagonists of vitronectin receptors. (A): contortrostatin inhibits adhesion of T24 completely (squares), whereas 7E3 only partially inhibits adhesion (triangles). (B): P1F6 alone (solid circles) only partially inhibits adhesion of T24, but in combination with 7E3 (10 μg/ml), P1F6 (diamonds) is able to inhibit adhesion completely. (C): contortrostatin inhibits adhesion of T24-β3 neg. completely (squares), whereas 7E3 has no effect on adhesion (triangles). (D): P1F6 alone (solid circles) significantly inhibits adhesion of T24-β3 neg. The presence of 7E3 (10 g/ml) does not enhance the inhibitory ability of P1F6 (diamonds). Each data point represents mean ± standard deviation of three individuals replicates which were linked by non-linear regression curves. The experiments were repeated three times with identical results.

FIG. 24. Effects of monomeric disintegrins on tyrosine phosphorylation in tumor cells. MDA-MB-435 cells were treated with the indicated concentrations of echistatin (upper panel) or flavoridin (lower panel) or were treated simultaneously with monomeric disintegrins and 10 nM contortrostatin (CN) as indicated for 10 min. Lysates were analyzed for phosphotyrosine content by immunoblot as described in Experimental Procedures.

FIG. 25. Contortrostatin-induced tyrosine phosphorylation is mediated by the αvβ3 integrin. A, Suspended 293 cells expressing either αvβ5 (αvβ5 293) or αvβ3 (αvβ3 293) were treated for 10 min with the indicated concentrations of contortrostatin (CN). β3 293 cells responded to contortrostatin treatment with increased tyrosine phosphorylation while β3 293 cells showed no response. Lysates were analyzed for phosphotyrosine content by immunoblot as described in Experimental Procedures. B, T24 cells (upper panel) or MDA-MB-435 cells (lower panel) were treated simultaneously for 10 min with contortrostatin (CN) and the indicated concentrations of the anti-αvβ3 mAb 7E3. Whole cell lysates were analyzed by phosphotyrosine immunoblot.

FIG. 26. Contortrostatin treatment causes tyrosine phosphorylation of CAS and FAK. Lysates from MDA-MB-435 cells were immunoprecipitated with antibodies specific for CAS or FAK followed by anti-phosphotyrosine immunoblotting, or were immunoblotted with the same antibody used for immunoprecipitation to demonstrate equal loading. FAK (upper panel) and CAS (lower panel) are maximally tyrosine phosphorylated at 10 nM contortrostatin (CN), which corresponds to the peak in tyrosine phosphorylation, with varying contortrostatin concentrations (FIG. 1).

DETAILED DESCRIPTION OF THE INVENTION

Characterization, Cloning and Expression of CN

Figure 2:
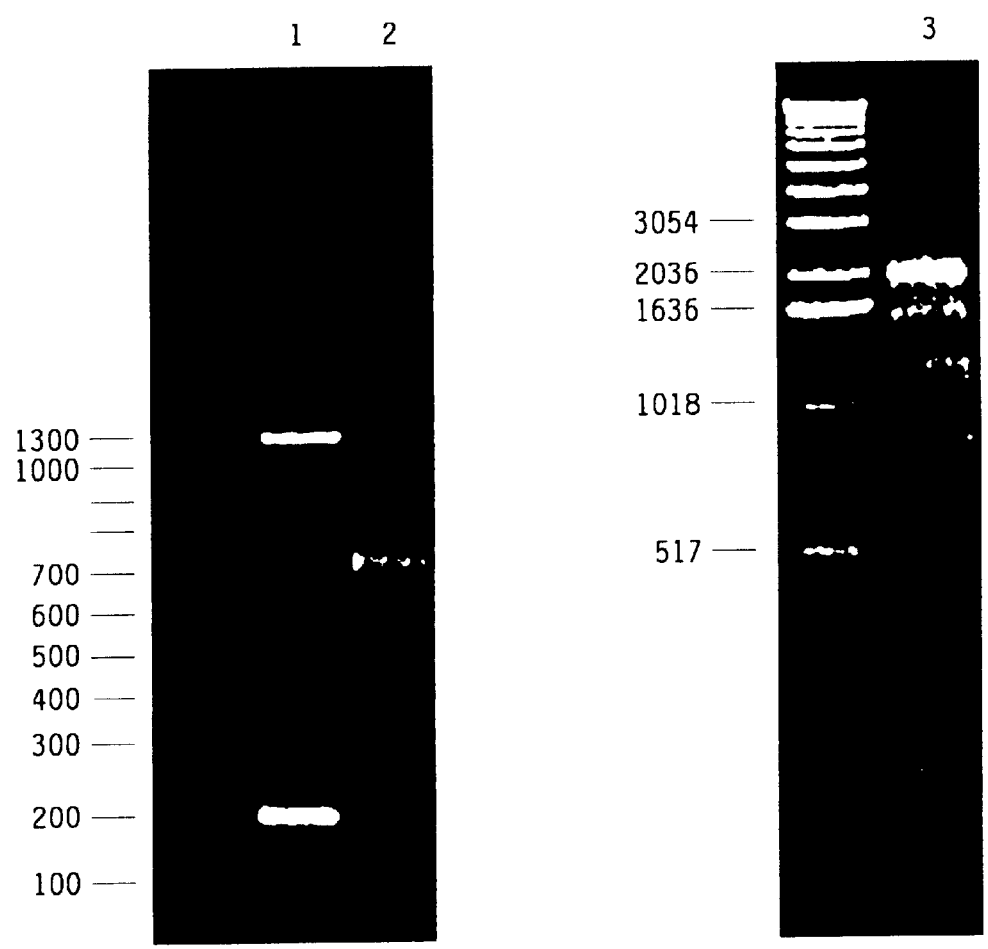
FIG. 2 shows electrophoresis of the PCR products, wherein a major band of about 1,300 bp was amplified with PCR primed by λgt10 forward and PCR-2 (lane 1), a band of approximately 700 bp resulted from PCR primed by PCR-2 and λgt10 reverse (lane 2), and the overlapping product of the two fragments is shown in lane 3, with a molecular size of about 2,000 bp.

We have purified and characterized a disintegrin: contortrostatin (CN) from *A. c. contortrix* venom. CN is a homodimer with a mass of 13,505 for the intact protein and 6,956 for the reduced and pyridylethylated protein. To test binding affinity to platelet (GP)IIb/IIIa (fibrinogen receptor), competition of CN with [$^{125}$I]7E3, an antibody directed to (GP)IIb/IIIA, was analyzed using human platelet rich plasma (PRP). CN displayed an $IC_{50}$ of 25 nM. Thus, CN is a potent β3 integrin antagonist.

The cDNA of CN has been amplified from a library of *A. c. contortrix* venom gland cells, constructed in λgt10. Amino acid composition and partial amino acid sequences of CN have been determined by Edman degradation; see FIG. 1. Using this information a full-length cDNA of 2,027 nucleotides (SEQ ID NO:1), which encodes a contortrostatin precursor protein, has been cloned and sequenced.

As a member of disintegrin super family, CN shares high similarity with other disintegrins including, trigramin whose nucleotide sequences were known. FIG. 1A shows a partial amino acid sequence of CN based on Edman degradation assay. The partial sequence is also compared with other disintegrins as indicated. The RGD sequence is bold-faced. The highly conserved PCCDAATCKL sequences on which PCR primers are designed are underlined. FIGS. 1A and 1B show how the cDNA of CN has been cloned by means of PCR using primers based on the highly homologous sequences among the disintegrin family as well as known λgt10 sequences flanking the cDNA inserts. The PCR primer pairs are: SEQ ID NO:5 (λgt10 forward primer) and SEQ ID NO:3 (PCR-1) 5'-GATTTACAGGTTGCAGCATCGC-3', which is antisense of trigramin cDNA encoding part of the underlined conserved sequence (FIGS. 1A and 1B). SEQ ID NO:4 (PCR-2), which is complementary to PCR-1, and SEQ ID NO:6 (λgt 10 reverse primer). SEQ ID Nos. 5 and 3 amplify DNA coding for amino acids upstream to the underlined part. SEQ ID Nos. 4 and 6 amplify those coding for the downstream part of CN. Full length cDNA has been obtained by overlapping extension of the two pieces of PCR products (see FIGS. 1C and 2).

The cDNA sequence and deduced amino acid sequence of contortrostatin precursor are shown in FIG. 3. The full length sequence is composed of 2,029 nucleotides (SEQ ID NO:1). It is composed of an 86 nucleotide non-translatable region at the 5' end, an open reading frame coding for 483 amino acids (SEQ ID NO:2), and a 3' non-coding region.

FIG. 4 shows the multidomain structure of contortrostatin (SEQ ID NO:2) compared to that of four other snake venom hemorrhagic proteins: trigramin (SEQ ID NO:8); Cat (catrocollastatin from *Crotalus atrox* venom) (SEQ ID NO:12); jararhagin (from *Bothrops jararaca* venom) (SEQ ID NO:13); and Ht-e (from *C. Atrox* venom) (SEQ ID NO:14). According to the structural division of snake venom metalloproteinases, the precursor of contortrostatin can be divided into a pro-protein (amino acid residues 1 to 190 of SEQ ID NO: 1 or 2), metalloproteinase (residues 191 to 410 of SEQ ID NO: 1 or 2) and disintegrin (residues 419 to 483 of SEQ ID NO: 1 or 2) domains. The mature monomer of native disintegrin starts at D419, i.e., the aspartic acid residue at position 419. Underlined portions of FIG. 4 show the RGD sequences of both contortrostatin and trigramin, as well as the conserved HEMGHNLGIHH sequences (e.g., amino acids 334 to 344 of SEQ ID NO:8) of the zinc-binding motifs in the metalloproteinase domains of each molecule.

According to the present invention, therefore, there is also provided a protein consisting essentially of purified contortrostatin or purified contortrostatin variants retaining the properties of a disintegrin, or a precursor of contortrostatin having pro-protein, metalloproteinase, and disintegrin domains. This protein can be purified from natural sources such as snake venom or can be made by recombinant techniques as will be understood by those skilled in the art with reference to the disclosure herein.

Still further, the present application claims both the native and synthetic amino acid and nucleotide sequences. Unless otherwise modified, the term "protein" as used herein encompasses both native and synthetic polypeptides and peptides. Synthetic protein includes recombinant and chemically synthesized protein. Unless otherwise indicated, the term "contortrostatin" include both the native and synthetic versions of the proteins.

The term "nucleotide sequence" includes both the DNA and RNA sequences. For example, the nucleotide sequence for a contortrostatin protein ("contortrostatin nucleotide sequence") includes the gene ("contortrostatin gene") encoding the native and precursor protein, its complementary DNA, and the RNA corresponding to the foregoing; also included are messenger RNA encoding for the contortrostatin protein, its complementary RNA, and the DNA corresponding to the foregoing. Further, as used in this application the nucleotide sequences include: (1) the DNA sequences encoding the contortrostatin proteins, (2) the nucleotide sequences (which may be RNA or DNA) complementary to the foregoing sequences, (3) the corresponding RNA sequences to the DNA sequences wherein the Thymidine ("T") in the disclosed DNA sequences is replaced with Uracil ("U"), (4) nucleotide sequences wherein other nucleotides known in the art such as nucleotide analogs, replace those in the foregoing sequences, for example, 5-methylcytosine replacing cytosine, and (5) nucleotide sequences that are for example, at least 90% identical, or more preferably at least 95% identical, as determined by FASTA or BLAST using default opening and gap penalties and a default scoring matrix.

Since nucleotide codons are redundant, also within the scope of this invention are equivalent nucleotide sequences which include: nucleotide sequences which code for or can be translated into the contortrostatin proteins, their protein variants, functional equivalents, or derivatives. These nucleotide sequences may also be used in the practice of the invention.

In addition to the above, contortrostatin nucleotide sequences also include: (1) nucleotide sequences that are capable of hybridizing to the coding sequences of the respective nucleotide sequences, under stringent hybridization conditions, and (2) fragments of or mutagenized nucleotide sequences of those disclosed herein which can encode or can be translated into proteins having substantially the same biological characteristics/activities of the respective contortrostatin proteins, e.g. integrin antagonist, zinc-binding, proteinase, anti-angiogenic factor, and further activities as disclosed herein in further embodiments and examples.

The terms "contortrostatin proteins", as used in relation to proteins include the respective proteins described in the Example section, below, and precursor proteins obtainable by the methods of the present invention, most preferably proteins exhibiting the properties of a disintegrin obtainable from the isolation methods of the Example section below. As will be appreciated by those of skill in the art, the contortrostatin proteins may be subject to allelic variations. Accordingly contortrostatin proteins include: (1) protein variants of these proteins, e.g. these protein variants may contain amino acid sequences that are, for example, at least 90% identical, or more preferably at least 95% identical to the pro-protein, metalloproteinase, disintegrin and/or native contortrostatin regions of the protein; (2) the functional equivalents of these proteins and their variants, respectively; and (3) the derivatives, including fragments, of the contortrostatin proteins and their variants, respectively. The percent identity of the amino acid sequences of contortrostatin proteins are as determined by FASTA or BLAST using default opening and gap penalties and a default scoring matrix (available at the National Center for Biotechnology Information website; www.ncbi.nlm.nih.gov).

The variants can result from, e.g. substitution, insertion, or deletion of the amino acid sequences of the contortrostatin proteins. The derivatives of the proteins and their variants, include fragments of these proteins and immunorective peptides that specifically bind with antibody to contortrostatin.

Two amino acid sequences are functionally equivalent if they have substantially the same biological activities such as the ability to bind to integrin receptors. The proteins may be fused to other proteins, for example, signal sequence fusions may be employed in order to more expeditiously direct the secretion of recombinant contortrostatin proteins.

Substitutional variants of the proteins disclosed herein are those in which at least one residue in the disclosed sequences has been removed and a different residue inserted in its place. Preferably, the amino acid change is conservative. Thus, modifications of the contortrostatin proteins' primary amino acid sequences also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that the polypeptide retains its biological activity, e.g., antibodies raised to the substituted polypeptide also immunoreact with the unsubstituted polypeptide.

Further, as is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Additionally, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein is not destroyed. It is expected that such modifications may quantitatively or qualitatively affect the activity, either by enhancing or diminishing the activity of the protein in various assays.

Individual amino acid residues in the chain may also be modified by oxidation, reduction, or other derivatization, and the protein may be cleaved to obtain fragments which retain activity. Such alterations which do not destroy activity do not remove the protein sequence from the definition. The following discusses some of the modifications in further detail by way of example.

Thus, glycosylation variants are included within the scope of contortrostatin proteins. They include variants completely lacking in glycosylation (unglycosylated) and variants having at least one less glycosylated site than the native form (deglycosylated) as well as variants in which the glycosylation has been changed.

As illustrated in the examples, native CN may be isolated from the venom of *Agkistrodon contortrix contortrix* in a relatively straightforward manner. Alternatively, CN may also be prepared by exploiting a variety of biochemical methods in current use, such as recombinant DNA technology or the like. Moreover, the sequence information reported herein can be used for making probes to identify variants, fragments, conserved domains or pro-proteins having substantial homology to CN and its precursor(s). Once identified, the genes may be isolated, further manipulated, and cloned into expression vectors.

There is also provided a vector containing a DNA molecule encoding a contortrostatin protein made according to techniques understood by those with skill in the art with reference to the disclosure herein. In the present invention, the contortrostatin nucleotide sequence may be inserted into a recombinant expression vector. The term "recombinant expression vector" refers to a plasmid, virus or other vehicle known in the art that has been manipulated by insertion or incorporation of a contortrostatin genetic sequence. Such expression vectors contain a promotor sequence which facilitates the efficient transcription of the inserted genetic sequence in the host. The expression vector typically contains an origin of replication, a promoter, as well as specific genes which allow phenotypic selection of the transformed cells. These vectors may be used to transform competent hosts to produce transformants that are capable of producing the snake venom protein.

Further, there is provided, a prokaryotic or eukaryotic host cell stably transformed or transfected by the vector, as well as a method of making the contortrostatin protein or its biological variants. The method includes the steps of, first culturing a prokaryotic or eukaryotic host cell transformed with DNA encoding for contortrostatin protein; and then, recovering the contortrostatin protein. The host cell can be mammalian cells, plant cells, insect cells, yeast and other fungi, or bacteria.

Sources of DNA sequences encoding for the proteins include isolated DNA from suitable cells or cell lines, cloned DNA from a snake venom genomic library or cloned DNA from a complementary DNA library, where the total complementary DNA is reverse transcribed to DNA and cloned. Once a DNA sequence is identified which encodes for a protein of interest, the sequence of bases may be determined by known means [e.g., Maxam and Gilbert, *Proc. Natl. Acad. Sci. USA* 74:560 (1977)]. In addition, hybrid DNA technology may be employed for obtaining expression. The DNA sequence may be restriction mapped and appropriate sites for cleavage defined. In this way, the sequence may be excised and introduced into a vector having the appropriate regulatory signals. A more detailed discussion of suitable techniques for identification and expression of disintegrin genes is provided in, e.g., U.S. Pat. Nos. 5,182,260 and 5,196,403 to Maraganore et al., the entire disclosures of which are hereby incorporated by reference.

Further, the sequence encoding the native protein may then be manipulated (for example, by single or multiple mutations or deletions) in a manner well known in the art to provide modified proteins, in which changes of one or more amino acids have been introduced. Following the procedures described herein, the determination of whether a particular polypeptide exhibits an activity profile characteristic of CN would then be a matter of routine experimentation. Accordingly, the present invention contemplates both the native CN and mutations thereof which exhibit the characteristic activity profile defined herein. Moreover, CN may also be employed in the form of a fusion protein with a suitable thrombolytic agent. Fusion proteins of this type may be prepared in a manner analogous to that described for formation of platelet aggregation inhibitor/anti-thrombin polypeptide fusion proteins in the aforementioned U.S. Pat. Nos. 5,182,260 and 5,196,403 to Maraganore et al.

Despite the high sequence homology with other disintegrins (shown in FIG. 1A) [Niewiarowski, S., McLane, M. A., Kloczewiak, M., and Stewart, G. J. Disintegrins and Other Naturally Occurring Antagonists of Platelet Fibrinogen Receptors, *Seminars in Hematology*. 31:289–300 (1994)], contortrostatin displays a unique amino-terminal sequence with a truncation of about 8 amino acids. In comparison with other disintegrins, two cysteine residues are missing at the amino-terminus of contortrostatin. It is well established that monomeric disintegrins possess an even number of cysteines, all of which are involved in disulfide bond formation. The missing two cysteines in the contortrostatin precursor may lead to disruption of disulfide bond pairing. This in turn may lead to the formation of two intermolecular disulfide bonds between two identical chains to form the homodimeric structure of contortrostatin. FIG. 5 presents a hypothetical model of the structure of the dimeric disintegrin as compared to a disintegrin, kistrin, whose disulfide bond positioning is known [Adler, M., Carter, P., Lazarus, R. A., and Wagner, G. Cysteine pairing in the glycoprotein IIb/IIIa antagonist kistrin using NMR, chemical analysis, and structure calculations, *Biochemistry* 32:282–9 (1993)]. In FIG. 5A, the sequences of the two disintegrins are compared. It can be readily seen that kistrin, with 12 half-cystines, forms 6 disulfide bonds. By comparison, contortrostatin, which has two unpartnered cysteine residues, can form the homodimeric structures presented in FIG. 5B. We are not sure at present which alignment is preferred, but we are confident, based on mass spectral analysis and SDS-PAGE of native and reduced contortrostatin, that a homodimeric structure most probably identical to one of the two shown, is formed.

CN is clearly quite different from applaggin, as the latter has been demonstrated unmistakably to be a monomer [Wencel-Drake et al. (1993), supra]. Moreover, CN does not inhibit platelet release reactions, as has been demonstrated to be the case with applaggin in the aforementioned U.S. Pat. Nos. 5,182,260 and 5,196,403 to Maraganore et al. Finally, despite the similarities in sequence there are also significant differences between the sequences with respect to both the start site and the ensuing sequences.

Methods of Use

CN has been found to be a potent inhibitor of human, rabbit and canine platelet aggregation in vitro. Unlike applaggin, however, CN does not inhibit platelet release reactions. Platelets comprise a plurality of different granules, including alpha granules and dense granules, whose contents are released when the platelets aggregate. The finding that CN does not inhibit platelet release of granule contents (including ATP from the dense granules) signifies that the platelets may still release their contents (and thus maintain some semblance of normal physiological activity) notwithstanding the inhibition of aggregation. By contrast, when applaggin inhibits platelet aggregation it also inhibits platelet release (as measured by, e.g., inhibition of serotonin release from the dense granules). Thus, normal platelet physiological processes are necessarily further perturbed with administration of applaggin.

Several lines of evidence indicate that CN inhibits platelet aggregation by binding specifically to the (GP)IIb/IIIa integrin receptor. For example, in a fibrinogen-(GP)IIb/IIIa ELISA [Dennis, M. S. et al., *Proc. Natl. Acad. Sci.* (*USA*) 87:2471 (1990)], in which the extent of purified (GP)IIb/IIIa bound to immobilized fibrinogen can be quantitated, CN effectively blocks (GP)IIb/IIIa binding. Additionally, the partial amino acid sequence of CN indicates considerable similarity with other disintegrins known to bind to (GP)IIb/IIIa. Finally, CN blocks 7E3 binding to (GP)IIb/IIIa. 7E3 is a murine monoclonal antibody that specifically binds to (GP)IIb/IIIa, thereby inhibiting human and canine platelet aggregation [Coller, B. S. et al., *J. Clin. Invest.* 72:325 (1983)]. In the presence of a low concentration of CN, 7E3 binding to platelets is significantly inhibited.

Three snake venom disintegrins, kistrin [Yasuda et al. (1990), supra], echistatin [Holahan et al. (1991), supra] and bitistatin [Shebuski, R. J. et al. (1990), supra], have demonstrated a potential role as antithrombotic agents for use in thrombolytic therapy by enhancing and sustaining arterial thrombolysis in conjunction with recombinant tissue plasminogen activator. Based on the low $IC_{50}$ values of CN, its in vivo efficacy as an antithrombotic agent has been examined. Using a canine reoccluding carotid arterial thrombosis model, CN has been found to efficiently sustain opening of the carotid artery in conjunction with anisoylated plasminogen streptokinase activator complex (APSAC). APSAC alone was found insufficient to prevent the rapid reocclusion of the carotid artery. Heparin was not needed to sustain opening when CN was administered with APSAC. This is a significant distinction over other disintegrins (e.g., echistatin, bitistatin and kistrin) which have been evaluated in models of coronary artery thrombosis.

The compositions of the present invention are particularly useful for treatment of thrombotic diseases in mammals, alone or in conjunction with one or more thrombolytic agents. In particular, the compositions of the present invention have utility in treating or preventing arterial, venous and microvascular thrombosis and thromboembolism. Thus, the compositions have utility in treating stroke, transient ischemic attacks, arteriosclerosis, atherosclerosis, pulmonary embolism, aneurisms and angina. In particular, the compositions have utility in preventing or treating myocardial infarctions.

The compositions of the present invention also have utility in inhibiting metastasis in melanoma, carcinoma and sarcoma patients. CN has been observed to bind to at least two sites on human melanoma M24 met cells: a high affinity site with a dissociation constant (Kd) of 1.1 (±0.7) nM and 96,000 (±39,000) sites per cell; and a lower affinity site with a Kd of 41 (±13) nM and 480,000 (±90,000) sites per cell. Moreover, CN has been found to inhibit human melanoma M24 met cell adhesion to fibronectin and vitronectin, and to a lesser extent to collagen and laminin. Thus, methods and compositions for preventing metastases in melanoma, carcinoma and sarcoma patients are also contemplated as within the scope of the present invention.

In accordance with the present invention, the unique properties of disintegrins are exploited in methods and compositions for preventing metastasis in carcinoma, sarcoma and melanoma patients. In particular embodiments the positions and methods are provided for preventing metastasis in breast cancer patients.

In further embodiments, we provide the protein contortrostatin from southern copperhead snake venom that possesses potent anti-tumor activity. A sophisticated technique has been developed to purify this protein from the complex mixture of proteins found in southern copperhead venom. As indicated above, originally CN was characterized as an inhibitor of platelet aggregation. We have purified several disintegrins from snake venoms. Contortrostatin (CN) was purified from southern copperhead venom. Disintegrins contain a constrained Arg-Gly-Asp (RGD) sequence at the tip of a flexible peptide loop, of about 13 amino acid residues flanked by Cys residues, protruding from the main protein core. See, e.g. amino acid residues 457 to 469 of SEQ ID NO: 1 or 2. This exposed RGD sequence enables disintegrins to bind to integrins with high affinity.

We have developed a metastatic breast cancer model by implanting human breast cancer cells into the mammary fat pads of mice. The mice we use were genetically manipulated so that their immune system is deficient and they are unable to reject the implanted human cancer cells. We observed that palpable tumor masses developed in the mammary fat pads two weeks after cancer cell implantation, and that tumor cells spread to the lungs in untreated animals within 12 weeks. CN or placebo was injected daily into tumors in several different groups of mice. Following treatment we found that the size of the tumor masses in the CN treated mice were significantly smaller than those in placebo-treated mice. Significantly, the CN-treated group showed >90% inhibition of tumor spread to other sites in the body (metastasis), as compared to the placebo group. Our studies indicate that CN blocks the attachment of breast cancer cells to proteins which are essential components of blood vessel walls. CN also inhibited new blood vessel formation (neovascularization) induced by breast cancer cells following incubation on a chick embryo membranous respiratory organ called the chorioallantoic membrane while placebo treatment did not. Since neovascularization is critical to continued proliferation of a growing tumor the ability to inhibit the growth of new vessels is an important anti-cancer action of CN.

Based on these studies it appears that disintegrins such as the snake venom protein contortrostatin possess anti-metastatic activity. Our findings suggest that CN blocks several critical steps in metastasis and is, therefore, more potent than other agents which only block a single step.

The disintegrin-containing compositions of the present invention are also useful in treatment of osteoporosis. Osteoclasts are multinucleated cells up to 400 $\mu$m in diameter which resorb mineralized tissue in vertebrates. Bone resorption appears to proceed by a combination of processes involving attachment to bone, polarized secretion of acid and proteases, and active motility of osteoclasts along the bone substrate; osteoclasts bind to bone via an RGD-sequence as an obligatory step in bone resorption, and this RGD-binding integrin is at adhesion structures [Sato, M. et al., *J. Cell Biol.* 111:1713 (1990)]. The molecular mechanisms whereby osteoclasts attach to bone are not well understood; however, by analogy to other cells, members of the integrin superfamily of divalent cation-dependent adhesion molecules are believed to mediate this interaction. Disintegrins, such as echistatin [Sato et al. (1990), supra] and presumably CN, inhibit bone resorption by isolated osteoclasts; the mechanism of action is presumably by disrupting adhesion structures. Accordingly, compositions and methods for treatment of osteoporosis employing an amount of CN effective to inhibit bone resorption by osteoclasts are also contemplated as within the scope of the present invention.

Finally, CN has utility in the promotion of wound healing. Events involved in wound healing are known to include alterations in integrin expression or functional activity and suggest that integrin receptor modulation plays a central role in wound repair and inflammation. Fibronectin is also known to play a number of roles in the wound healing process. Although fibronectin function is thought to be critical to effective wound healing, there are reports that at least one of its activities (the binding of bacteria) may be counterproductive [Grinnell, F., *J. Cell. Biochem.* 26:107 (1984); Clark, R. A. F., *Arch. Dermatol.* 124:201 (1988)]; the presence of fibronectin in the wound bed may thus promote bacterial attachment and infection. Fibronectin also appears to be intimately involved in keloid formation. Keloids are a pathological consequence of wound healing that affects a significant proportion of non-Caucasian patients. Keloids are benign tumors of connective tissue that grow beyond the boundary of the original wound and are rich in fibronectin and type I collagen [Sible, J. C. & Oliver, N., *J. Cell. Biochem. Suppl.* 16F:170 (1992)]. By virtue of their inhibition of cell—cell and cell-extracellular matrix interactions (including interaction with fibronectin), disintegrins such as CN would be expected to have a profound effect on processes involved in wound repair, including keloid formation.

A major problem following obstetrical and gynecological surgery is the formation of adhesions. This widespread phenomenon observed in peritoneal wound repair is a leading cause of pain, intestinal obstruction and infertility. Adhesion formation appears to involve an imbalance in the fibrinolytic and fibroproliferative inflammatory responses and may also involve a modulation of the cell—cell or cell-extracellular matrix interactions. There is strong evidence for an important role of fibrin during the initial stages of adhesion formation [diZerega, G. S., *Prog. Clin. Biol. Res.* 381:1 (1993)]. The presence of cellular elements, including platelets, further exacerbates the role of fibrin. In view of the role of platelets and fibrin in adhesion formation, the use of disintegrins such as CN as a potential therapeutic agent is most attractive.

In preliminary studies in a rabbit model of adhesion formation, abrasion and devascularization of the uterine horns of rabbits were employed to induce adhesion formation during wound healing in untreated animals [Rodgers, K. et al., *Int. J. Fertil.* 35:40 (1990)]. Alzet pumps were employed to continuously deliver CN at a rate of 10 $\mu$l/hr (36 $\mu$g/ml). In this model system, decreased adhesion formation was observed in treated animals compared to controls. Therefore, compositions and methods for preventing adhesion formation whereby an amount of CN effective to prevent adhesion formation is administered to a patient in need of such treatment are also contemplated as within the scope of the present invention.

The compositions of the present invention comprise at a minimum an amount of CN effective to achieve the desired effect (i.e., prevent thrombus formation, prevent metastasis in carcinoma patients, prevent adhesion formation, etc.) and a suitable carrier or excipient. Generally, in these compositions, CN is present in an amount sufficient to provide about 0.01 mg/kg to about 50 mg/kg per day, preferably about 0.1 mg/kg to about 5.0 mg/kg per day, and most preferably about 0.1 mg/kg to about 0.5 mg/kg per day.

Such compositions have particular utility in the prevention of thrombus formation.

Alternatively, CN is administered in combination with at least one thrombolytic agent present in an amount effective to achieve thrombolysis. Suitable thrombolytic agents include, but are not limited to, the following: anisoylated plasminogen streptokinase activator complex (APSAC); tissue-type plasminogen activator (tPA); urokinase-type plasminogen activator (uPA); and fibrolase, a snake venom fibrinolytic agent as described in U.S. Pat. No. 4,610,879 to Markland, Jr. et al.

CN may be administered by a variety of heretofore known means suitable for delivery thereof into the blood stream in substantial amounts. Intravenous administration of CN in a suitable liquid vehicle or excipient is presently contemplated as the preferred route of administration. CN is soluble in water, and may therefore be effectively administered in a suitable aqueous solution (e.g., phosphate buffered saline). Alternatively, CN may be administered orally (in the form of tablets or capsules formulated with a suitable binder or excipient material, or in the form of aqueous or oily suspensions, solutions, emulsions, syrups or elixirs) or as a parenteral suspension. As is well known in the art, adjuvants such as local anesthetics, preservatives, buffering agents, lubricants, wetting agents, colorants, flavorings, fillers and diluents may suitably be included in any of these formulations.

EXAMPLES

These additional embodiments may be better understood with reference to the accompanying examples, which are intended for purposes of illustration only and should not in any sense be construed as limiting the scope of the invention as defined in the claims appended hereto.

In conducting the following examples, lyophilized venom from *Agkistrodon contortrix contortrix* was obtained from Biotoxins, Inc., St. Cloud, Fla. All chemicals were of the highest grade available. Pierce protein assay kit using bicinchoninic acid was employed to determine protein concentrations [Smith, P. K. et al., *Anal. Biochem.* 150:76 (1985)].

For hydrophobic interaction (HIC)-HPLC a Perkin Elmer 410 LC pump was employed with a LC-95 UV/VIS detector. For reverse phase HPLC a Spectra Physics LC 8810 pump was employed with an SP 8450 UV/VIS detector. Absorbance for HIC-HPLC was monitored at 280 nm and for RP-HPLC at 215 nm. A polypropyl aspartamide (250×21 mm) column (Poly LC, Columbia, Md.) was used for hydrophobic interaction HPLC. C18 (218TP54 and 218TP510) columns were used for reverse phase (RP) HPLC (Vydac, Hesperia, Calif.). For cation exchange chromatography a CM (carboxymethyl) 300 column (SynChrom, Inc., Lafayette, Ind.) was employed.

Example 1

Purification and Characterization of CN

CN was purified from *Agkistrodon contortrix contortrix* (Southern copperhead) venom using a four step HPLC procedure. For the first step of purification crude venom (1 g) was dissolved in 0.1 M phosphate buffer containing 1 M ammonium sulphate, pH 6.8 (buffer A) and applied to the polypropyl aspartamide HIC-HPLC column. Elution was achieved as follows: 50 minutes isocratically with 100% buffer A; a linear gradient for 90 minutes to 0.1 M phosphate, pH 6.8 (buffer B); 40 minutes isocratic at 100% buffer B. Fractions of 10 ml were collected in a Pharmacia Frac 100 fraction collector at 4° C. using a flow rate of 5 ml/min. Fractions containing platelet aggregation inhibiting activity were pooled and concentrated by ultra-filtration using an Amicon stir cell with a YM3 membrane. Proteins were detected at 280 nm; platelet aggregation inhibiting activity was observed in the flow through.

Further purification was achieved by C18 RP-HPLC. Fractions containing platelet aggregation inhibiting activity were pooled and concentrated for this second step. The C18 column (218TP510) was equilibrated with 95% of 0.1% TFA in water (solvent A) and 5% of 80% acetonitrile in 0.1% TFA in water (solvent B). Elution was achieved as follows: isocratic at 95% solvent A and 5% solvent B for 10 minutes; a linear gradient to 40% solvent B in 65 minutes; linear gradient to 100% solvent B in 20 minutes; isocratic at 100% solvent B for 25 minutes. Fractions were collected manually every minute at a flow rate of 7 ml/minute. CN eluted at 28% acetonitrile (66 minutes).

Fractions containing platelet aggregation inhibiting activity were pooled and rerun on the same C18 RP-HPLC column using a shallower gradient. Elution was achieved as follows: isocratic at 80% solvent A and 20% solvent B for 20 minutes; a linear gradient to 30% solvent B over 90 minutes; and a 25 minute linear gradient to 100% solvent B. CN eluted as a sharp peak at 22% acetonitrile (82 minutes). The minor peak eluting just before CN also contained platelet aggregation inhibiting activity and had a similar molecular weight to that of CN; due to the low yield, this peak was not further characterized.

A final purification step was performed using pooled fractions from the previous step. These pooled fractions were applied to a cation exchange, CM300, HPLC column and elution was achieved by an increasing gradient of sodium chloride. CN elutes at 52.5 minutes (160 mM NaCl). This step achieved a separation of CN from isoforms thereof. Yields of 1–2 mg of the four-step purified CN were obtained per gram of crude venom.

For SDS-polyacrylamide gel electrophoresis (SDS-PAGE) Tris-Tricine 16.5% gel was used according to published protocols under reducing and non-reducing conditions [Schagger, H. & Von Jagow, G., *Anal. Biochem.* 166:368 (1987)]. The gel was run using a BioRad minigel system and stained with silver [Morrisey, J. H., *Anal. Biochem.* 117:307 (1981)] or Coomassie blue R250.

SDS-PAGE analysis of CN revealed that it has a molecular mass of approximately 15,000 Daltons under non-reducing conditions and 5,000–7,000 Daltons under reducing conditions. This strongly suggests that CN is composed of two subunits. Another possibility, albeit unlikely, is that the large difference in migration may be attributed to differential uptake of SDS under non-reducing and reducing conditions.

The molecular weight of CN was confirmed by mass spectrometry using a triple quadrupole instrument with an electrospray ion source. A mass of 13,507 Daltons was determined for intact CN; the analysis also indicated a high degree of purity. Mass spectrometry of the reduced and pyridylethylated protein gave a mass of 7,996 Daltons. This is the expected value for the individual chains of a homodimer of this molecular weight, taking into account the incorporation of 1,248 mass units for the 12 pyridylethyl groups incorporated into the 6 reduced disulfide bounds (based on homology with known disintegrins, there should be 6 disulfide bonds). These findings place CN in a unique position among all the disintegrins reported to date in that it exists as a dimer. Scatchard analysis of CN binding to unactivated human platelets revealed a single class of binding sites with a dissociation constant ($K_d$) of 37 nM and number of binding sites ($B_m$) equal to 100,000. Reduction of the disulfide bonds completely eliminated platelet aggregation inhibitory activity, even at concentrations ten times the $IC_{50}$, suggesting that structural parameters are critical for maintaining activity.

Example 2 cDNA Cloning of Contortrostatin Using Polymerase Chain Reaction

Partial amino acid sequence analysis of contortrostatin using Edman degradation methods suggested that the subunit of contortrostatin is homologous with other disintegrins (FIG. 1A) with the cysteine residues aligned, as well as the RGD sequences [Niewiarowski, S., McLane, M. A., Kloczewiak, M., and Stewart, G. J. Disintegrins and Other Naturally Occurring Antagonists of Platelet Fibrinogen Receptors, *Seminars in Hematology* 31: 289–300 (1994)]. The strategy for cloning contortrostatin cDNA with PCR is based on the structural homology among the disintegrin family. Design of the PCR primers is schematically illustrated in FIG. 1. The underlined sequences in FIG. 1A are highly conserved among disintegrin family. PCR primers were synthesized based on this region. The nucleotide sequence coding this region in the cDNA of trigramin from *Trimeresurus gramineus* was used to synthesize the primers PCR-1 and PCR-2 (FIG. 1B). PCR-1 and PCR-2 are complimentary primers corresponding to the coding sequence of a consensus sequence PCCDAATCKL (e.g., amino acids 424 to 433 of SEQ ID NO:2) among disintegrins. Their nucleotide sequences are:

PCR-1: 5'-GTTTACAGGTTGCAGCATCGC-3' (SEQ ID NO: 3)

PCR-2: 5'-GCGATGCTGCAACCTGTAAAC-3' (SEQ ID NO: 4)

λgt10 forward and reverse primers which flanks the EcoRI site of the vector were used for PCR. Nucleotide sequences of the primers are listed below:

λgt10 forward primer: 5'-AGCAAGTTCAGCCTGGTTAAG-3' (SEQ ID NO:5)

λgt10 reverse primer: 5'-CTTATGAGTATTTCTTCCAGGGTA-3' (SEQ ID NO: 6)

Oligonucleotide primers were synthesized by the Microchemical Core Facility of the University of Southern California Comprehensive Cancer Center. Primers were provided in a deprotected lyophilized form, and were resuspended and diluted to the appropriate concentration with water prior to use.

Example 3

PCR Amplification of Contortrostatin cDNA

We used the cDNA library of *Agkistrodon contortrix contortrix* venom gland constructed in λgt 10 vector at the EcoRI site. The estimated titer of the library was $10^{10}$ plaque-forming units (pfu)/ml and the complexity was 50,000. 500 μl of the cDNA library phage solution was mixed with 500 μl of 20% polyethylene glycol (PEG)/1 M NaCl solution in an Eppendorf tube. The Eppendorf tube was inverted twice and incubated at room temperature for 30 min. The solution was then centrifuged at 14,000 rpm for 10 min. The supernatant was discarded and the pellet was resuspended in 100 μl of sterile water. The suspension was incubated with 10 μl of proteinase K (10 mg/ml) at 50° C. for 1 hr. The phage particle suspension was extracted with phenol/chloroform twice and the DNA was precipitated with 1/10 volume of 3M sodium acetate and 2 volumes of absolute ethanol followed by washing with 80% ethanol. DNA was resuspended in 10 μl of sterile water in preparation for PCR.

The PCR reaction was set up as follows: 5 μl of DNA solution was mixed with 1 μl of 25 mM dNTP's (Pharmacia), 1 μl (100 ng/μl) each of forward and reverse PCR primers, and 5 μl of 10×PCR buffer. The final volume of the reaction was brought up to 50 μl with water. After mixing, one drop of mineral oil was applied on top of the liquid. The Eppendorf tubes were pre-heated to 98° C. for 5 min, then incubated at 70° C. and 60° C. for 1 min respectively before cooled down to room temperature. 2.5 units of Taq DNA polymerase (Pharmacia) was added to each mix. The thermal cycler was programmed as follows: 96° C. for 15 sec, 55° C. for 30 sec, 72° C. for 1 min. PCR amplification was performed for 30 cycles. Following the last cycle, a final 72° C. extension step for 7 min was allowed before the samples were cooled down to 30° C. The PCR product was extracted with chloroform before it was analyzed by agarose gel electrophoresis. The bands resolved by electrophoresis were recovered from the agarose gel using Geneclean kit (Bio 101, Inc.) according to the manufacturer's manual for direct DNA sequencing.

λgt10 forward and PCR-1 primers were used to amplify the up stream region of the adhesion site (FIG. 1B). Similarly, PCR-2 and λgt10 reverse primers were coupled to amplify the down stream part of the cDNA (FIG. 1B). A major band of about 1300 bp (designated CN—N) was obtained with the first pair of primers (FIG. 2, lane 1), and a major band of approximately 700 bp (designated CN—C) resulted from PCR using the later pair of primers (FIG. 2, lane 2). CN—N and CN—C were subjected to nucleotide sequencing analysis prior to the overlapping extension. As expected, CN—N demonstrated high similarity to cDNA of trigramin which encodes its N-terminal signal peptide. CN—C nucleotide deduced amino acid sequence was very similar to the disintegrin COOH— terminal sequence encoding the RGD site.

Since PCR-1 and PCR-2 were complimentary, CN—N and CN—C overlap at this site, and therefore, can be assembled into a full length cDNA. To accomplish this goal, we used an overlapping extension method as shown in FIG. 1C. Briefly, equal molar amount of double-strand PCR products CN—N and CN—C were mixed with λgt10 forward and reverse primers. After denaturation of both double-strands, the subsequent reannealing results in two kinds of molecules. One is annealed CN—N and CN—C at the adhesion site with the recessive ends as 3'-ends. This molecule can be automatically elongated into full length double-strands using PCR. The other molecule is similarly annealed, but with the recessive ends as 5'-ends. Although these molecules are not self-elongated, the recessive parts can be filled in with priming by λgt10 primers at each end. FIG. 2, lane 3 shows the products of overlapping extension as resolved by agarose gel electrophoresis. The size of the major band is estimated to be 2,000 bp which equals the sum of CN—N and CN—C, and is thus designated "full length". The full length band was recovered from the gel and treated with EcoRI. Subsequently, this piece of DNA was subcloned into the plasmid vector pcDNA3.1(+).

Example 4

Subcloning of PCR Product Into Plasmid Vector

Plasmid pcDNA3.1(+) was digested with EcoRI (Pharmacia) followed by dephosphorylation using T4 phosphatase (Boehringer-Mannheim). PCR overlapping extension product was also digested with EcoRI. The PCR product was inserted into the linearized vector by ligation reaction using T4 ligase (Pharmacia) at 16° C. overnight. All the reactions were set up and performed according to standard protocols. Successful ligation was selected by plating transformed *E. coli* (DH5α) on ampicillin containing plates. Plasmids containing the insert were amplified in *E. coli*. Purified plasmid DNA was obtained with Qiagene DNA Miniprep columns.

Example 5 cDNA Sequencing

Automated DNA sequencing was performed by the Microchemical Core Facility. PCR primers were used as sequencing primers for direct sequencing of PCR products. For sequence analysis of the insert in plasmid pcDNA3.1(+), T7 promoter primer and BGH reverse primer, which flanks the multiple cloning sequence (MCS), was utilized to initiate the assay. Typical reactions gave readable sequences of 400 to 600 bp. The sequencing reactions were performed on double-stranded DNA in the case of plasmid DNA. With the synthesis of new sequencing primers, additional sequences were obtained, and these were assembled into overlapping contiguous sequences using DNAsis computer program.

FIG. 3 shows the full length nucleotide sequence inserted between the EcoRI sites. It is composed of 2,029 nucleotides, which is the size of the full length band of the overlapping extension (FIG. 2, lane 3). Following an 86-nucleotides 5'-end non-translated region (5'-NTR), an open reading frame is found between nucleotides number 87 and 1535. Nucleotide 1536 to 1538 is the termination codon. The 3'-NRT possesses an AATAAA site in the 3'-end non-coding region, and ends with poly(A) tail, suggesting that the cDNA we obtained with the overlapping extension was indeed a complete cDNA (FIG. 3). The open reading frame encodes 483 amino acids (SEQ ID NO:2). The structure of cDNA deduced amino acid sequence can be divided into three domains. The first 190 amino acids of SEQ ID NO:2, starts with methionine, are highly similar to the pro-protein of many cloned snake venom proteins (comparison is shown in FIG. 4). From amino acid 191 to 418 of SEQ ID NO:2 is the metalloproteinase domain including a Zinc-binding motif HEMGHNLGISH (aa 334 to 344 of SEQ ID NO:2). The remaining 65 amino acids of SEQ ID NO:2 belong to contortrostatin monomer which is identical to the known partial amino acid sequence of contortrostatin determined by Edman methodology. This sequence is very similar to those of many disintegrins whose sequences have been determined (FIGS. 4 and 1A). The calculated molecular weight of the disintegrin is 6.77 kDa, which is equal to that of CN monomer. The RGD (aa 461 to 463) sequence is in bold face letters. The three-domain structure matches the precursor model of snake venom metalloproteinase and disintegrin proposed by Kini et al. [Structural Domains in Venom Proteins: Evidence that Metalloproteinases and Nonenzymatic Platelet Aggregation Inhibitors (Disintegrins) from Snake Venoms are Derived by Proteolysis from a Common Precursor, *Toxicon* 30:265–296, (1992)]. There is evidence that disintegrins are synthesized in the snake venom gland cells as a multi-domain precursor which undergo post-translational proteolysis and folding to generate a mature disintegrin.

Example 6

Assay of Platelet Aggregation Inhibitory Activity

Column fractions obtained during purification were assayed for activity using fresh human platelet rich plasma (PRP) prepared from blood obtained from human volunteers who had had no medication for at least two weeks. Blood (36 ml) was drawn into 4 ml of 0.1 M citrate and centrifuged at 150×g for 20 minutes. The supernatant, PRP, was removed and the remaining blood was centrifuged at 10,000 RPM to obtain platelet poor plasma (PPP). Platelet counts were adjusted to 250,000 platelets/µl using a Coulter counter. A Helena four channel aggregometer was used to monitor platelet aggregation. Inhibition of ADP-induced platelet aggregation was monitored at 37° C. by adding venom fractions one minute prior to the addition of ADP (10–20 µM final concentration). Fractions exhibiting platelet aggregation inhibiting activity were pooled and further purified. Rabbit and canine PRP was prepared by the same procedure and used in the studies described below.

Figure 6:
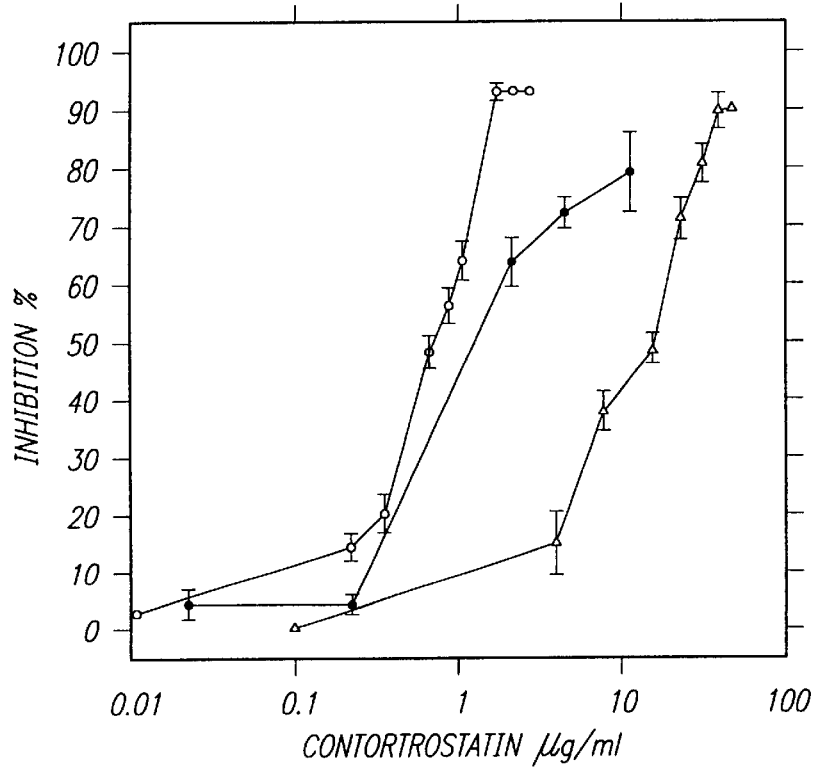
FIG. 6 illustrates the results of determinations of CN inhibition of human, canine and rabbit platelet aggregation.

CN inhibited ADP-induced platelet aggregation in human, canine, and rabbit PRPs (FIG. 6). Empty circles represent human platelet rich plasma, solid circles represent canine PRP, and empty triangles represent rabbit PRP. Varying concentration of CN were preincubated for one minute with PRP prior to the addition of ADP. CN (0.73 µg/ml) inhibited 10 µM ADP-induced human platelet aggregation by 50% ($IC_{50}$). The $IC_{50}$ for 20 µM ADP-induced canine platelet aggregation was 1.8 µg/ml for CN. Interestingly, the $IC_{50}$ for CN mediated inhibition of rabbit platelet aggregation was considerably higher; the $IC_{50}$ for 20 µM ADP-induced rabbit platelet aggregation was 17.3 µg/ml for CN.

Example 7

Measurement of (GP)IIb/IIIa Specific Binding

Measurement of CN binding to platelet (GP)IIb/IIIa receptor was carried out using PRP prepared from blood obtained from human volunteers or male mongrel dogs. PRP was prepared as described above and the platelet count was determined with a H-10 cell counter (Texas International Laboratories, Inc., Houston, Tex.). PRP (180 µl) was incubated with 20 µl of varying concentrations of CN at room temperature. Radiolabelled antibody ($^{125}$I-7E3 IgG, 20 µl, 18 mg/ml, 80,000 cpm), specific for (GP)IIb/IIIa, was then added and the mixture incubated for 30 minutes. To establish equilibrium binding, 50 µl aliquots of the binding assay mixture were layered over 200 µl of 30% sucrose in 0.4 ml microcentrifuge tubes and spun at 10,000 RPM for 4 minutes in a swinging bucket rotor to separate platelet-bound antibody from free antibody. The pellet and the supernatant were separated and counted in a Packard Minaxi 5000 series gamma counter. The number of molecules of $^{125}$I-7E3 bound per platelet in the presence and absence of CN was calculated by using the following formula:

$$\frac{(4) \times 0.9 \text{ µg } 7E3 \times 3.76 \times 10^{12} \text{ molecules } 7E3/\text{µg}}{(5)}$$

wherein (1)=Pellet counts; (2)=Supernatant counts; (3)=Total CPM (1)+(2); (4)=Fraction bound (1)/(3); and (5)=Platelet counts per µl×45 µl.

Figure 7A:
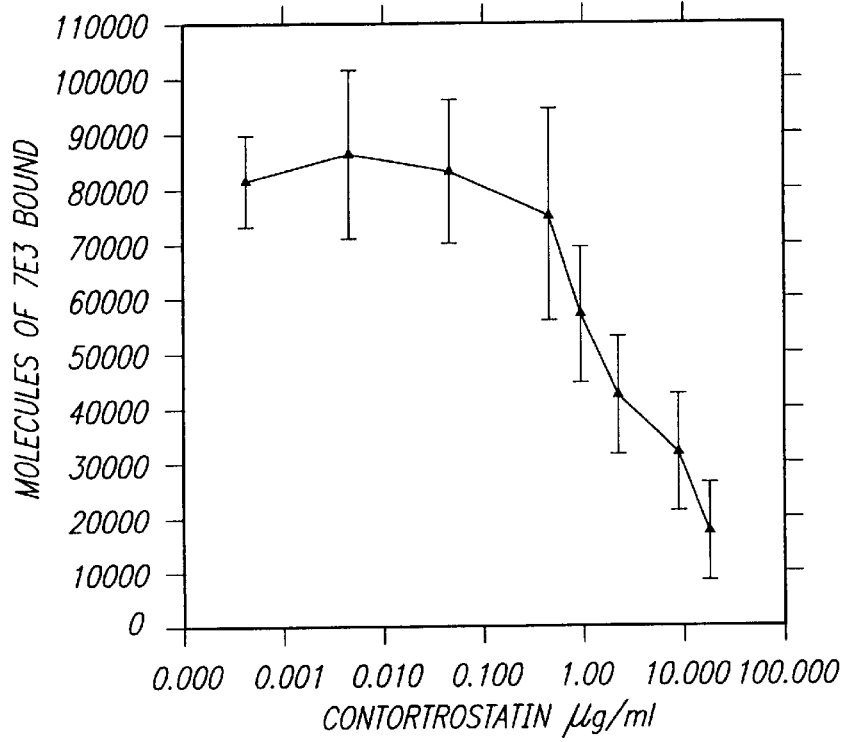
FIGS. 7A and 7B illustrate the results of binding studies of CN to human (FIG. 7A) and canine (FIG. 7B) (GP)IIb/IIIa in the presence of a fixed saturating concentration of murine monoclonal antibody 7E3.
Figure 7B:
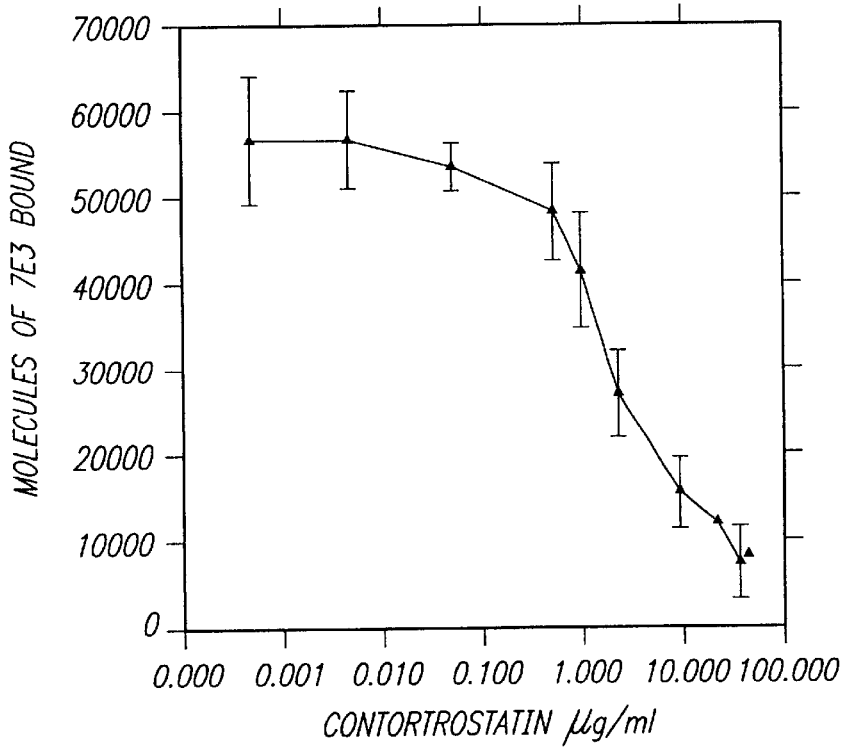

The competitive binding studies using 7E3 demonstrated specific platelet (GP)IIb/IIIa receptor binding for CN with both human (FIG. 7A) and canine (FIG. 7B) platelets. The concentration of CN to inhibit 50% of 7E3 binding to human (GP)IIb/IIIa ($IC_{50}$) is 0.4 µg/ml. The $IC_{50}$ for CN for canine (GP)IIb/IIIa is 0.24 µg/ml. These studies confirm that CN inhibits platelet aggregation by binding to (GP)IIb/IIIa.

Example 8

In Vivo Thrombolytic Efficacy of CN

CN has been studied in a reoccluding canine model of arterial thrombosis. The protein was studied initially by systemic infusion at different dosages to determine its relative potency. This data has permitted an assessment of the systemic dose needed for effective antithrombotic (antiplatelet) activity. The effects upon physiological parameters and circulating coagulation factors have also been monitored.

The model of carotid artery thrombosis in the anesthetized canine described is a modification of one developed for the study of experimentally-induced coronary artery thrombosis [Romson, J. L. et al., Thromb. Res. 17:841 (1980)]. The experimental procedure results in the formation of a platelet rich intravascular thrombus at the site of an electrolytically-induced endothelial lesion in proximity to a distal arterial stenosis. The carotid artery is selected for the experimental model, thereby allowing one vessel to be used as a control and the other to be used after administration of the thrombolytic and antithrombotic therapy. APSAC (anisoylated plasminogen streptokinase activator complex) has been used as the thrombolytic agent successfully in this model. The carotid artery response to the electrolytic injury is similar to that observed in the canine coronary artery but has the advantage of each dog demonstrating the ability to form bilateral occlusive thrombi. The lytic-antithrombotic combination of agents may then be administered to only one of the occluded vessels; this allows for an internal control and eliminates those animals that may not form thrombi due to causes unrelated to the vessel wall injury and subsequent occlusive thrombus formation, i.e., low circulating platelet counts, enhanced spontaneous thrombolysis, presence of heart worms, etc. Parameters which are recorded include repeated measures of: phasic and mean carotid artery blood flow velocity using an ultrasonic flow probe, time to thrombotic occlusion, time to recannulization, ex vivo platelet aggregation, prothrombin time, thrombin time, activated partial thromboplastin time, red cell and white cell counts, hematocrit, EKG profile and body temperature, before and after administration of APSAC or APSAC plus CN to separate groups of animals.

Figure 8:
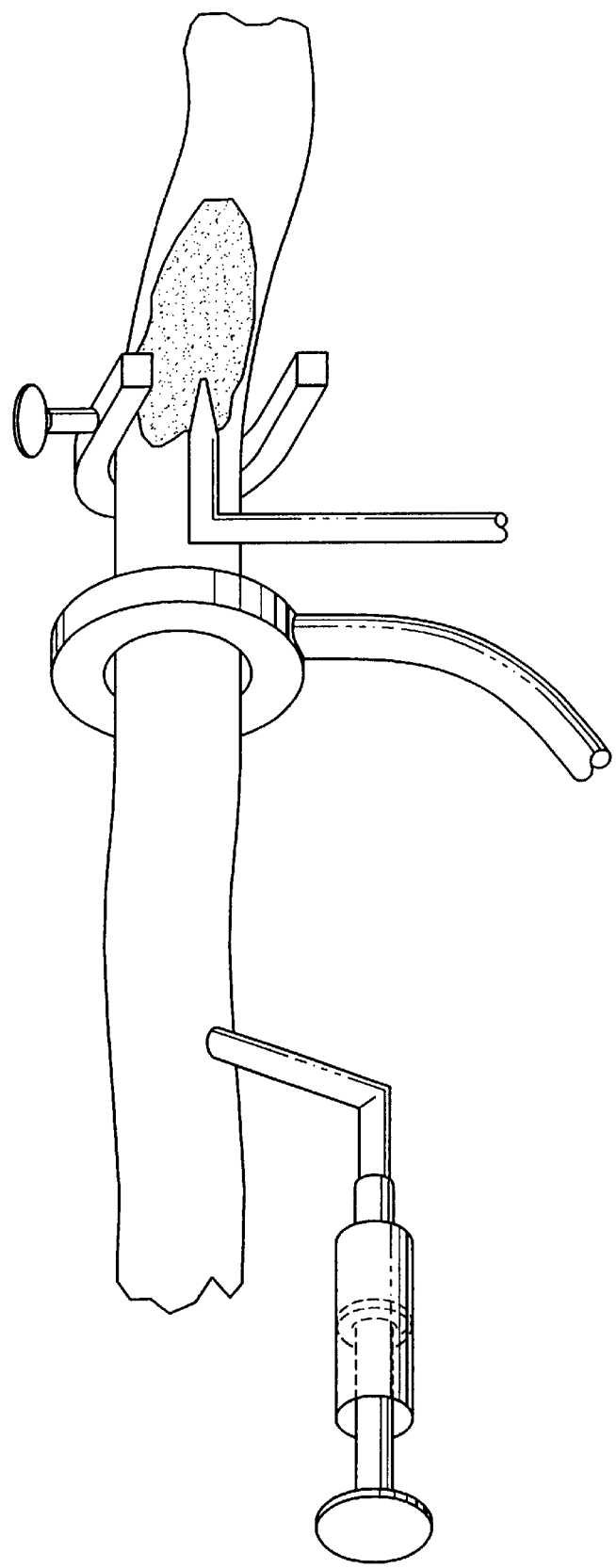
FIG. 8 is a schematic representation of an instrumented canine carotid artery showing placement of an ultrasonic flow probe, mechanical constrictor (stenosis) and intra-carotid anodal electrode for inducing intimal injury to the vessel wall to initiate thrombus formation.

Conditioned male mongrel dogs (8–10 kg) have been used for all in vivo studies. Dogs are anesthetized with sodium pentobarbital, intubated and allowed to breath room air under positive pressure respiration. Arterial blood gasses and pH determinations are made every 45 minutes and appropriate adjustments made to maintain the blood gasses and arterial pH within normal limits. Both common carotid arteries and the right internal jugular vein are exposed. A catheter is inserted into the jugular vein for blood sampling and administration of the test drug. Arterial blood pressure is monitored from the cannulated femoral artery with the use of a blood pressure transducer. A Doppler flow probe is placed on each common carotid artery proximal to both the point of insertion of the intraarterial electrode and the mechanical constrictor. The constrictor is adjusted until the pulsatile flow pattern is reduced by 50% without altering mean blood flow. Blood flow velocity in the carotid vessels is monitored continuously. FIG. 8 is a schematic representation of the instrumentation of the carotid artery.

Electrolytic injury to the intimal surface of each carotid vessel is accomplished with the use of an intravascular electrode. Each intraarterial electrode is connected to the positive pole (anode) of a dual channel stimulator. The cathode is connected to a distant subcutaneous site. The current delivered to each vessel is monitored continuously and maintained at 300 $\mu$A. The anodal electrode is positioned to have the uninsulated portion in intimate contact with the endothelial surface of the vessel. Proper positioning of the electrodes in each of the carotid arteries is confirmed by visual inspection at the end of each experiment. The anodal current is applied for a maximum period of 3 hours or is terminated 30 minutes after blood flow in the involved vessel remains stable at zero flow velocity to verify having achieved formation of a stable occlusive thrombus. The right carotid artery serves as the control vessel, whereas the left carotid artery serves as the test vessel. Vessel wall injury is induced simultaneously in each carotid artery.

APSAC (0.05 U/kg) is infused as a bolus proximal to the thrombus in the left carotid artery only. The dose of APSAC has been determined as one that will consistently lyse the locally injected carotid thrombus without producing a systemic lytic effect. Thus, lysis in the uninjected right carotid should not occur. CN is given intravenously in a 10% bolus immediately following APSAC and the remaining 90% is infused over 1 hour. CN dosages ranged from 0.155 to 0.40 mg/kg; the agent was dissolved at the appropriate dose in a volume of 20 ml of sterile saline for infusion. Reperfusion is defined as the restoration of carotid artery blood flow velocity to 20% of baseline values. Patency is defined as measurable carotid artery flow velocity. Blood pressure, heart rate, and carotid artery flow velocity are monitored for 6 hours or until rethrombosis occurs.

Blood (20 ml) was withdrawn for platelet studies from the jugular cannula into a plastic syringe containing 3.2% sodium citrate as anticoagulant (1/10 citrate/blood, vol/vol). Blood was taken for platelet aggregation and whole blood cell counts at baseline 60, 120, 180, 240 and 300 minutes after the administration of CN. The platelet count was determined with a cell counter. Platelet rich plasma, the supernate present after centrifugation of anticoagulated whole blood at 140×g for 5 minutes, was diluted with platelet poor plasma to achieve a platelet count of 200,000/mm$^3$. Platelet poor plasma was prepared after the platelet rich plasma was removed, by centrifuging the remaining blood at 12,000×g for 10 minutes and discarding the bottom cellular layer. Ex vivo platelet aggregation was measured by established spectrophotometric methods with a four channel aggregometer by recording the increase in light transmission through a stirred suspension of platelet rich plasma maintained at 37° C. Aggregation was induced with arachidonic acid (0.65 mM and 0.325 mM) and ADP (20 $\mu$M and 5 $\mu$M). A subaggregatory dose of adrenaline (550 nM) was used to prime the platelets before stimulation. Values are expressed as percentage of aggregation, representing the percentage of light transmission standardized to platelet rich and platelet poor plasma samples yielding 0% and 100% of light transmission, respectively.

At the conclusion of the study protocol each vessel segment is ligated, proximal and distal to the point of injury, and removed without disturbing the intravascular thrombus. The vessel segment is opened and the intact thrombus is lifted off and weighed.

Figure 9:
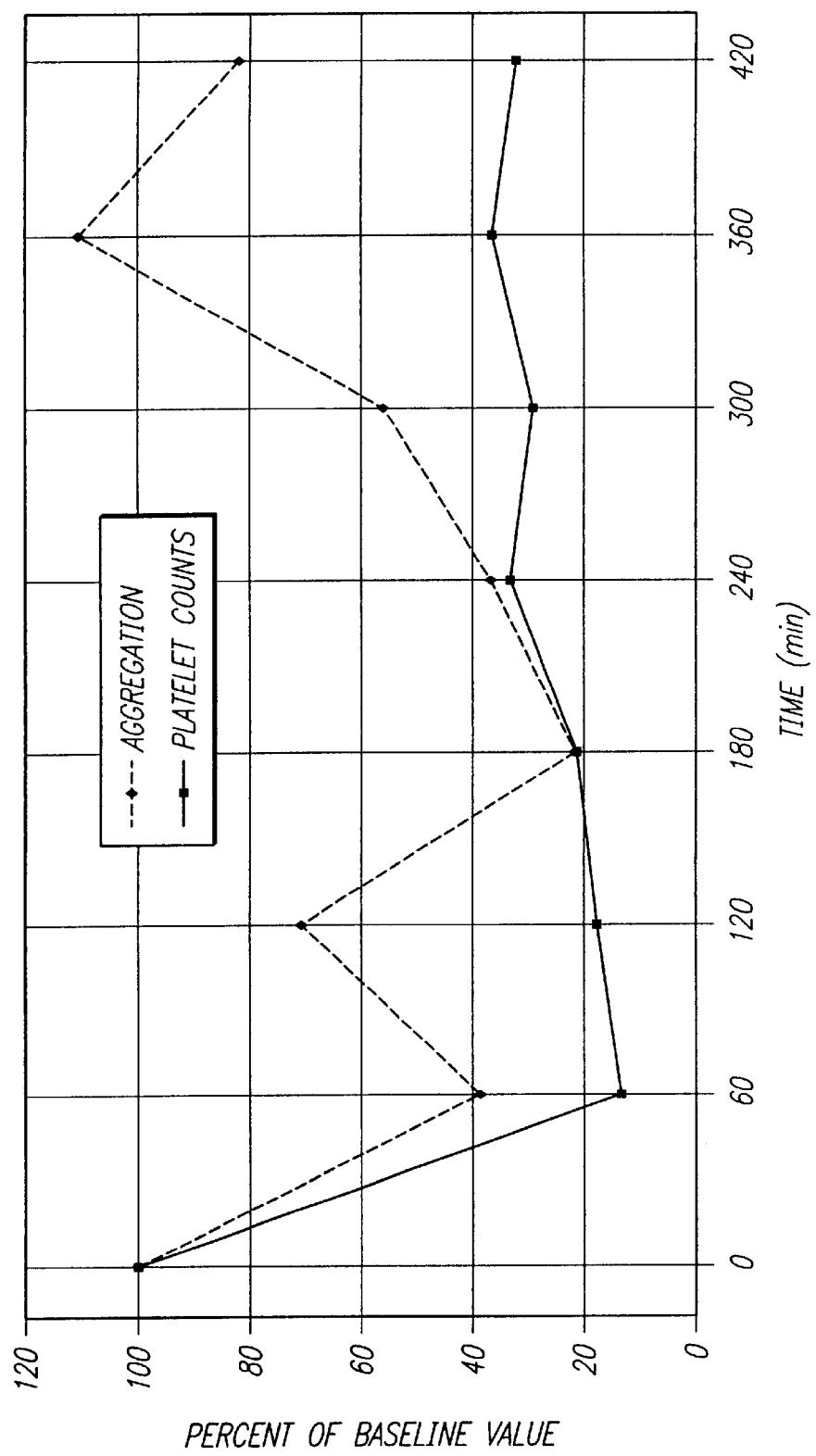
FIG. 9 illustrates platelet counts and platelet aggregability as percent of the value at zero time in a canine treated with anisoylated plasminogen streptokinase activator complex (APSAC) and CN.

Five animals have been studied thus far with CN plus APSAC, six with APSAC alone, and a positive control group of six dogs with APSAC plus 7E3 anti-(GP)IIb/IIIa monoclonal antibody. There were essentially no changes in mean arterial blood pressure or mean heart rate following infusion of CN. Further, the carotid artery flow velocity stayed at a high level following infusion of APSAC plus CN as compared to APSAC infusion alone. In the group of animals infused with APSAC alone, the carotid artery opened for a few minutes following infusion of the lytic agent but then reoccluded and remained closed for the duration of the study. In the positive control group, the animals were infused with APSAC (0.1 U/kg) intraarterially and this was followed by a bolus of 7E3 anti-(GP)IIb/IIIa F(ab')2 (0.8 mg/kg). In these three animals, the carotid artery remained open following infusion of the combination of APSAC and 7E3 and remained open until the conclusion of the experimental protocol. In the group of five animals infused with APSAC plus CN the results were essentially the same as with the combination of 7E3 and APSAC. However, Table 1 reveals that there was a significant advantage to the combination of APSAC plus CN in terms of the residual thrombus weight. In Table 1, CTTX=CN and RCA=right carotid artery. In the group of five animals treated with this combination of agents the residual thrombus weight per kg dog weight was 1.5, versus 2.4 in the six animals in the APSAC plus 7E3 group, and 4.1 in the APSAC alone group (six animals). Finally, in one of the dogs treated with APSAC plus CN (0.155 mg/kg) platelet aggregation and platelet counts were followed (FIG. 9); CN infusion began at time 0 and was continued for 60 minutes thereafter.

TABLE 1

WEIGHT OF RESIDUAL THROMBUS IN CANINE CAROTID ARTERY THROMBOSIS MODEL

| Dog # | APSAC Control Dog Weight (kg) | APSAC Control RCA Thrombus (mg) | APSAC & 7E3 Dog Weight (kg) | APSAC & 7E3 RCA Thrombus (mg) | APSAC & CTTX Dog Weight (kg) | APSAC & CTTX RCA Thrombus (mg) |
|---|---|---|---|---|---|---|
| 1 | 19.2 | 27.3 | 9.4 | 37.3 | 15.2 | 16.8 |
| 2 | 6.5 | 47.6 | 12.2 | 37.5 | 8.2 | 19.2 |
| 3 | 18.2 | 90.5 | 17 | 53.2 | 9.2 | 3.5 |
| 4 | 20.2 | 60.1 | 11.6 | 3.2 | 8.5 | 33.1 |
| 5 | 16.8 | 67.5 | 8.6 | 36.5 | 9 | 15.1 |
| 6 | 10 | 78.5 | 15.9 | 11.8 | | |
| Mean | 15.2 | 61.9 | 12.5 | 29.9 | 10 | 14.6 |
| SEM | 2.1 | 8.4 | 1.4 | 7.6 | 1.4 | 4.9 |
| Thrombus weight per kg | | 4.1 | | 2.4 | | 1.5 |

These results are typical of those in dogs in this group. It can be seen that platelet aggregation was compromised by treatment with the venom protein, but that there appeared to be a return of aggregation at the conclusion of the experiment. Similarly, the platelet count was also depressed during the course of the experiment. It is suspected that the platelets are sequestered in some sanctuary such as the spleen and are then released following a short residence time; platelets returning into the circulation appear to be functional. There is a drop in platelet counts to 10–20% of the baseline value, with recovery to 30–40% by the conclusion of the experimental procedure. Platelet aggregability fluctuates somewhat due to the low platelet count; however, it can be seen that platelet aggregability in the residual platelets appears to be returning to normal at the conclusion of the experimental procedure.

Example 9

CN Effects on Mammary Carcinoma Adhesion & Invasion

Figure 10:
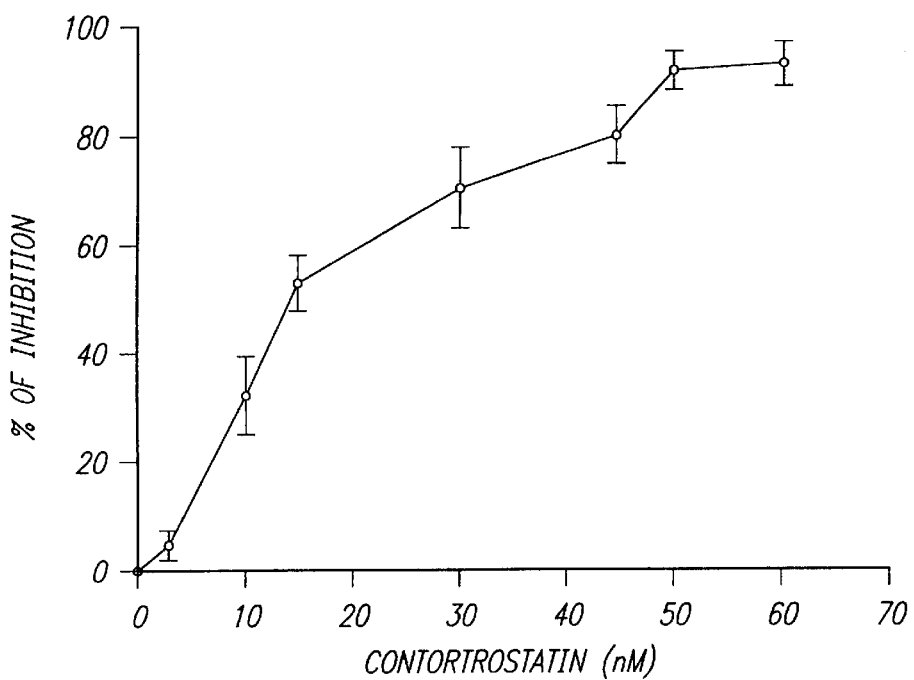
FIG. 10 shows CN inhibited adhesion of MDA-MB-435 to fibronectin.
Figure 11:
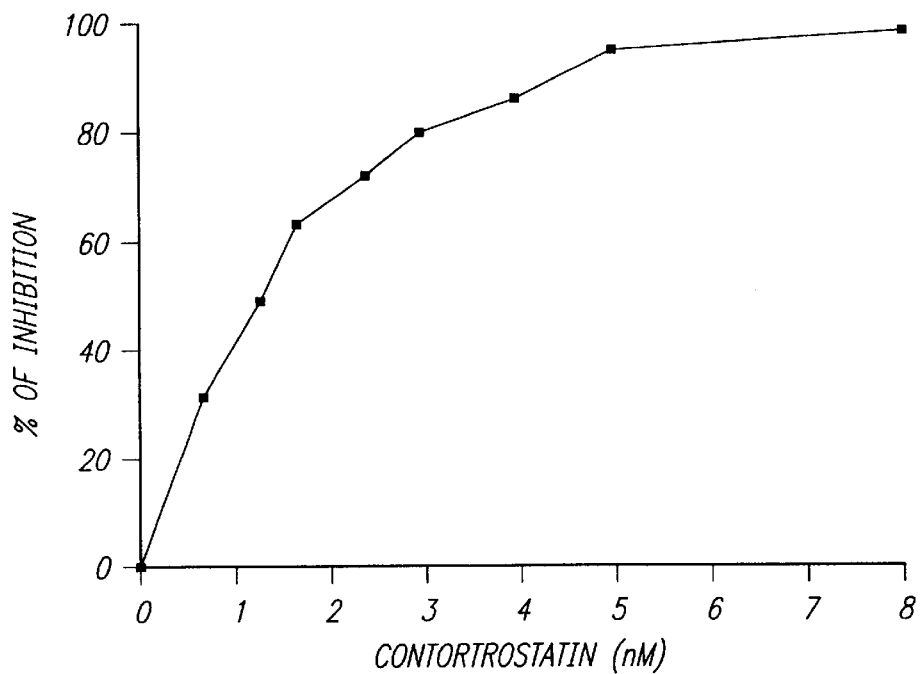
FIG. 11 shows CN inhibited adhesion of MDA-MB-435 to vitronectin.

The effect of CN on binding of highly metastatic human breast cancer cells, MDA-MB-435 cell line, to ECM proteins was examined. Human fibronectin and vitronectin were immobilized in the wells of 96-well microtiter plates. Referring to FIGS. 3 and 4, CN inhibited adhesion of MDA-MB-435 to both ECM proteins in a dose dependent manner. $IC_{50}$ for adhesion to fibronectin is 18 nM (FIG. 10) and for vitronectin the $IC_{50}$ is 1.5 nM (FIG. 11). CN had minimal effect on the weak adhesion seen by MDA-MB-435 cells to human type I collagen, or to rat type I collagen to which the MDA cells have a relatively strong affinity. In a variation of the above experiments, CN was immobilized. It was found that CN can support binding of MDA-MB-435 cells in a dose dependent manner. Binding of MDA-MB-435 cells to immobilized CN is blocked by an RGD peptide, GRGDSP (SEQ ID NO:15) ($IC_{50}$=0.4 mM), and by EDTA ($IC_{50}$=0.8 mM). Since integrin receptors require metal ions for non covalent association of their subunits, our findings indicate that CN binds to integrin receptors on the surface of MDA-MR-435 cells via an RGD-mediated mechanism. The finding that immobilized CN can support adhesion of MDA-MB-435 cells suggests that this binding involves cell surface receptors on the tumor cells. Referring to FIGS. 12 and 13, varying concentrations of GRGDSP (FIG. 12) or EDTA (FIG. 13) were used to inhibit binding of human mammary carcinoma cells to immobilized CN. CN was at 0.1 μg/well. The vertical line at each data point indicates the y-axis error bar. All experiments were conducted as three sets of triplicates for each data point.

Since adhesion of MDA-MB-435 cells to immobilized CN is completely blocked by GRGDSP and by EDTA (FIGS. 12 and 13), CN binds solely to integrin receptors of MDA-MB-435 cells via an RGD-dependent mechanism.

Figure 14:
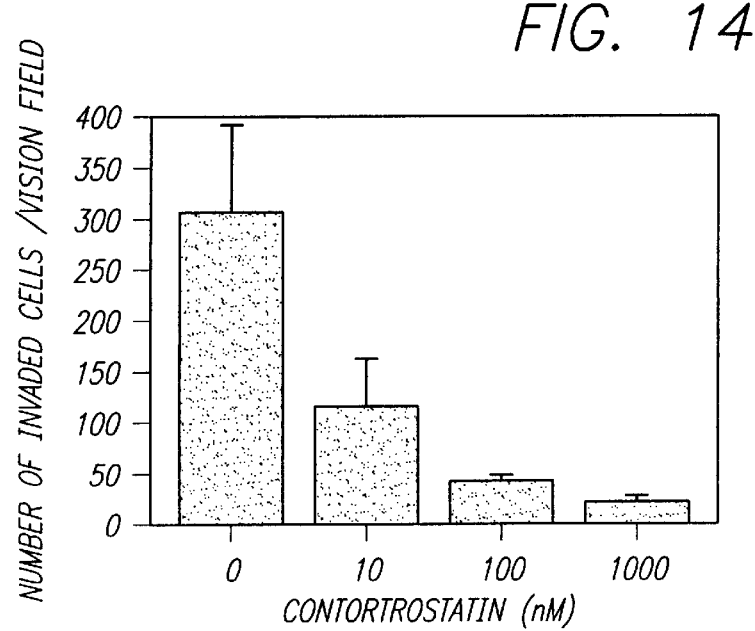
FIG. 14 shows the inhibition of invasion of MDA-MB-435 cells through a Matrigel coated invasion chamber.

Referring to FIG. 14, we have also demonstrated the inhibitory effect of CN on the invasion of a synthetic basement membrane by the MDA-MB-435 cells using a Matrigel-coated invasion chamber. $2.5 \times 10^3$ MDA-MB-435 cells treated with various concentration of CN were allowed to migrate across the Matrigel layer for 48 hrs. Assays at each CN concentration were performed in triplicate. Cells invaded through the Matrigel filter were fixed and stained. Invaded cells were quantitated with microscope by the mean of cell numbers in three randomly selected vision field.

Example 10

Figure 15:
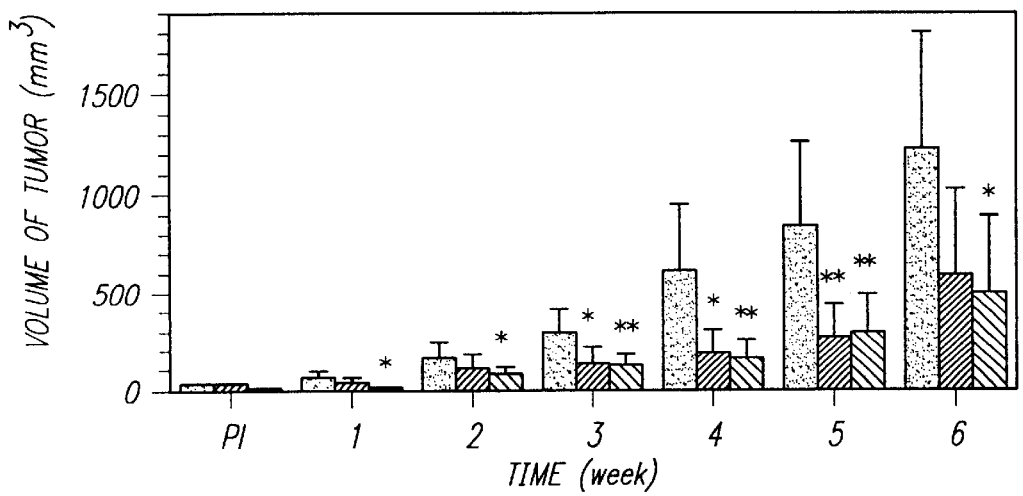
FIG. 15 shows the effect of CN on the growth MDA-MB-435 tumor in experimental nude mice.

CN Inhibits Growth and Metastasis of MDA-MB-435 Breast Cancer in Nude Mouse Experimental Model A spontaneous (orthotopic) metastatic model of nude mice has been established by implantation of MDA-MB-435 cells ($5 \times 10^5$ in 0.1 ml) in the mammary fat pads (mfp). Palpable tumors appeared by the 10th day post-implantation. Daily injections of CN into the tumor masses of each of the groups arc carried out, started at the 14th day post-implantation. By the 8th week post-implantation, tumors were removed. The animals were allowed to survive for 2 more weeks without CN administration. The animals were then sacrificed and lung metastases were carefully examined. Referring to FIG. 15, our findings indicate that local injection of CN substantially inhibited the growth rate of the tumor. The volumes of tumor masses (mean±S.D.) of control (dark bars), low-dosage (0.5 μg/day, gray bars), and high-dosage (5 μ/day, light gray bars) CN-treated group are shown. The seven clusters of bars from left to right represent the data of pre-injection (PI, 14th day post-implantation) and the 1st through 6th week of injection. Student t-tests were employed to test the significance of differences. *and** indicate P<0.05 and p<0.01, respectively. The mean weight of tumors treated by high-dose CN (5 μg/day) is significantly lower than control group (P<0.05). Table I shows the incidence of lung metastasis based on gross examination and counting of surface nodules. Metastatic spread in the control group is much more extensive than the high dose CN group which showed >90% inhibition of metastasis. These data demonstrate the potential therapeutic role of CN in the treatment of human breast cancer.

TABLE 2

Effect of Contortrostatin on the Incidence of Metastatic MDA-MB-435 Breast Cancer in Nude Mouse Experimental Model.

| Groups | Metastasis Incidence | | | |
|---|---|---|---|---|
| | In situ relapse | Mean size of relapse tumor (mm³) | # of nodules in lung (median) | Other Organs[1] |
| Control | 4/5 | 66.7 ± 51.7 | 47.5[2] | 5/5 |
| CN (5 µg/day) | 2/6 | 48.7 ± 10.5 | 4.5 | 2/6 |

[1]Organs include: Chest wall, mediastinum, diaphragm, and pleurae
[2]In 2/5 animals, lungs are directly invaded by cancer cells from pleurae and mediastinum.

Example 11

CN Inhibits Angiogenesis Induced by MDA-MB-435 Tumor in CAM

Figure 16A:
FIG. 16 is a photograph demonstrating tumor induced angiogenesis in a control chick embryo chorioallantoic membrane (CAM) (FIG. 16A), CAM treated with 20 μg of CN (FIG. 16B), and CAM treated with 150 μg of CN (FIG. 16B)
Figure 16B:
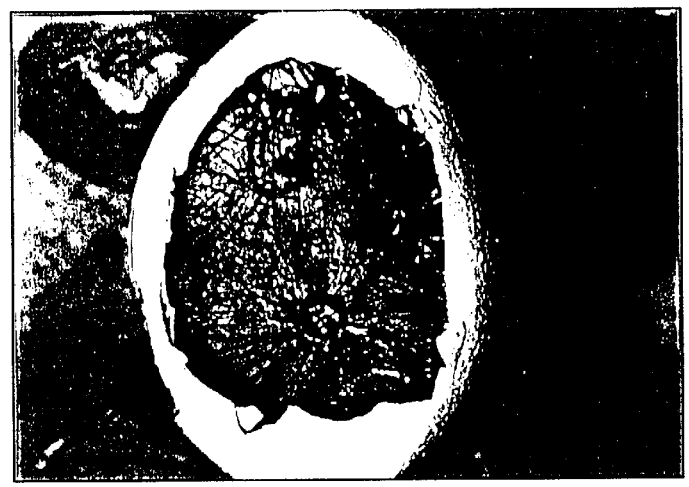
Figure 16C:
Figure 18A:
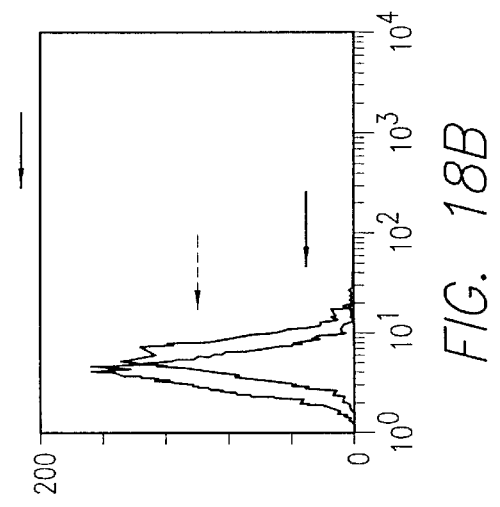
FIG. 18. Expression patterns of integrins αvβ3 and αvβ5 in T24 and T24-β3 neg. cell lines. This figure shows the binding of antibodies, 7E3 (anti-αvβ3) and P1F6 (anti-αvβ5), to the cells. Binding of the antibodies was detected with a secondary antibody conjugated to FITC using flow cytometry. The background peak in each assay is labeled by the dashed arrow. The peaks represents the cells treated with specific antibodies are labeled with the solid arrows. 7E3 (10 μ/ml) binds to T24 cells and causes a right-shift of the peak (A), P1F6 (10 μg/ml) also binds to the cells and causes a slight right-shift (B), suggesting that T24 expresses both αvβ3 (major) and αvβ5 (minor). On T24-β3 neg. cells, no 7E3 binding is found, as shown by the overlapping peaks (C). However, P1F6 binds to the cells (D), indicating that the cells express only αvβ5. Data shown here is representative of three identical experiments.
Figure 18B:
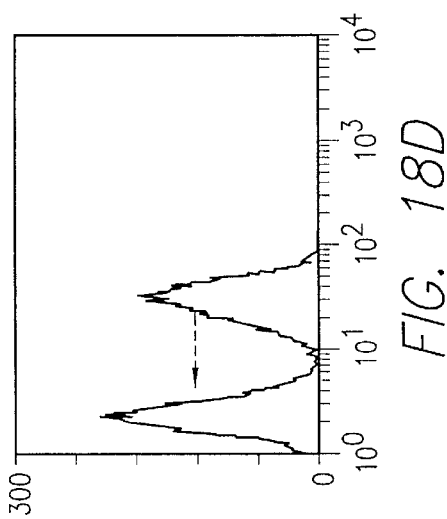
Figure 18C:
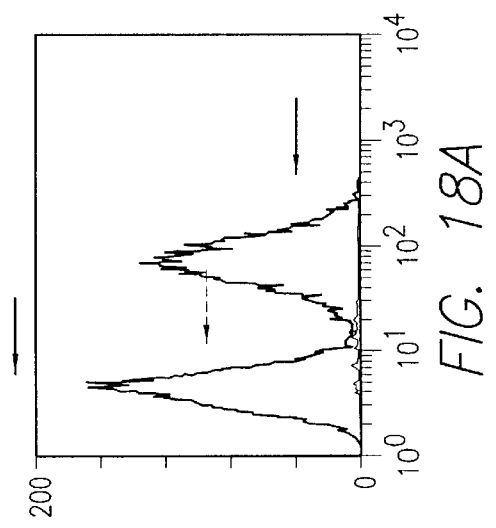
Figure 18D:
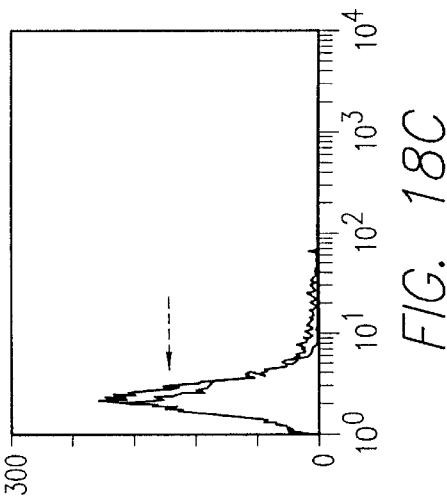

The hypothesis that inhibitory effect on the growth of the tumors probably results at least in part from the blockage of angiogenesis by CN has been preliminarily verified by observing tho effect of CN on tumor induced angiogenesis on chick embryo chorioallantoic membrane (CAM). MDA-MB-435 tumor masses were inoculated on CAM of 10-day chick embryos. CN at various dosages were injected intravenously into CAM on day 2 post-inoculation. Tumor induced angiogenesis and inhibitory effect of CN on angiogenesis can be easily observed in CAM after 3 days of incubation. As shown in FIG. 16, vessels are distributed in a convergent manner with the tumor mass in the center in control embryo. Chick embryo is immunodeficient, and thus allows the growth of implanted MDA-MB-435 tumor. The embryos are incubated at 37° C. with humidity at 60%. CN at various dosages was injected intravenously into CAM on day 2 post-inoculation. Tumor induced angiogenesis on the 3rd day is demonstrated the photos. On the top (FIG. 16A) is the control embryo. The vessels are distributed in a convergent manner with the tumor mass in the center. In the middle (FIG. 16B) is the CAM treated with 20 µg of CN. On the bottom (FIG. 16C) is the CAM treated by 150 µg of CN. The 20 µg CN treated embryo vessels are thinner and less dense than control; tumor mass is smaller than that on control CAM. On CAM treated by 150 µg of CN the vessels are even thinner and the convergent distribution pattern disappears completely; there is a necrotic tumor mass with volume significantly smaller than control and low dose CN, presumably due to the lack of blood supply (FIG. 16).

Example 12

CN has no Effect on Growth of MDA-MB-435 Cells In Vitro

Figure 17:
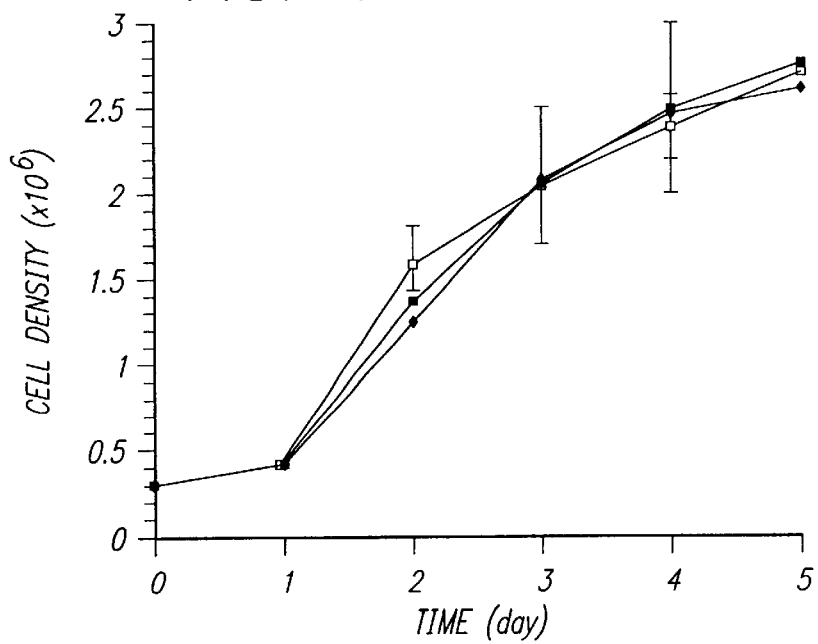
FIG. 17 shows the effect of CN on the proliferation of MDA-MB-435 cells in vitro.

MDA-MB-435 cells (0.3×106/ml) were added to each well of a 6-well cell culture plates coated with 1/100 dilution of Matrigel . Cells were then treated with CN at various concentration. Growth curves of MDA-MB-435 cells in vitro without CN (circles), and with CN at 100 nM (triangles), and 500 nM (diamonds) are illustrated. Six-well cell culture plates coated with Matrigel (1/100 dilute) were seeded with 3 ml of MDA-MB-435 cell suspension (0.3× 10⁶/ml). Cell density was determined every 24 hours. Referring to FIG. 17, cells in the presence of CN proliferate equally well as control cells. The result indicate that CN has no direct cytotoxicity during in vitro culture of MDA-MB-435 cells.

Example 13

CN is Effective and Well Tolerated In Vivo

It can be concluded from the chronic experiment with nude mice mentioned above that CN is not toxic. Despite its platelet aggregation inhibitory activity, no spontaneous hemorrhage is observed during the experiment. Some bleeding at the injection sites in CN treated animals, however, was noticed.

CN is a novel antimetastatic agent. We hypothesize that CN blocks several critical steps (e.g. adhesion, invasion, angiogenesis) in cancer metastasis and progression. Therefore, it is more potent than other agents which block a single step.

Example 14

Contortrostatin Binds to Integrin αvβ5 as a Mechanism of its Antineoplastic Activity Introduction: Disintegrins, the most potent known inhibitors of integrin function, are a class of cysteine-rich peptides isolated from the venom of the Viperidae and Crotalidae families of snakes. They bind with high affinity to integrins on the surface of platelets and other cells. The sequence RGD (Arg-Gly-Asp) is conserved in all of these peptides. This sequence is believed to bind to the platelet surface fibrinogen receptor αIIbβ3, which results in the inhibition of fibrinogen-dependent platelet aggregation. Except for barbourin, a KGD-containing (instead of RGD) disintegrin which is a relatively specific antagonist for αIIbβ3, other disintegrins are rather unspecific and can block function of other β3 integrins, as well as β1 integrins.

Contortrostatin is a disintegrin from *Agkstrodon contortrix contortrix* (southern copperhead) venom. Unlike other disintegrins, contortrostatin is a homodimer with a mass of 13,505 for the intact protein and 6,956 for the reduced and pyridylethylated protein as shown by mass spectrometry. In addition to its platelet aggregation inhibitory activity by binding to αIIbβ3, contortrostatin is also a novel antiangiogenic agent. Our recent studies indicate that αvβ3 on vascular endothelial cells is an important integrin to which contortrostatin binds. We have observed that contortrostatin blocks several critical steps including cell adhesion, invasion, and angiogenesis in cancer metastasis and progression. In previous studies, we found that contortrostatin inhibits VEGF-induced angiogenesis, which is reported to be regulated via an αvβ5-mediated signal transduction pathway. In our recent work, we proved that contortrostatin binds directly to αvβ5 and blocks the function of this integrin.

Significance: The function of αvβ5 has been indicated by many studies. Friedlander and colleagues found that blockade of αvβ3 only affects bFGF induced angiogenesis, whereas blockade of αvβ5 exclusively inhibits VEGF induced angiogenesis, suggesting that the growth factors utilize distinct signal transduction pathways which depend on different integrins. Interestingly, contortrostatin inhibits angiogenesis induced by both bFGF and VEGF in a chick chorioallantoic membrane model. Although αvβ5 participates in the initiation of cell adhesion to vitronectin, unlike αvβ3 which mediates cell migration constitutively, αvβ5 mediates migration only when activated by growth factors, such as insulin-like growth factor-1 (IGF-1), epidermal growth factor (EGF), and transforming growth factor-α (TGF-α).

Cooperation of growth factors and αvβ5-dependent migration and signal transduction have also been revealed. Although focal adhesion kinase (FAK) colocolizes with αvβ5 upon adhesion of the host cells, tyrosine phosphorylation of FAK does not increase until protein kinase C (PKC) is activated, perhaps as a result of upstream tyrosine kinase activation by growth factor receptors. Specific PKC inhibitor blocks VEGF-induced angiogenesis. On the downstream side of signal transduction pathway, Yebra et al reported that αvβ5 mediated cell migration requires a late activation event involving NFκB induced de novo gene transcription and protein synthesis. Recent research by the same group of investigators showed that activation of PKC and the consequent increase of αvβ5-dependent cell migration requires up regulation of urokinase-type plasminogen activator/urokinase-type plasminogen activator receptor (uPA/uPAR) complex and uPA enzymatic activity. The αvβ5-dependent intracellular signal cascade is clearly distinct from that of αvβ3, and it specifically regulates migration on vitronectin, but not other ECM proteins.

These findings support the idea that αvβ5 has an important role in mediating cell motility during angiogenesis and metastasis. Therefore, contortrostatin, as an antagonist of αvβ5, may be of significant utility for anti-angiogenic and anti-metastatic therapy. We discovered a novel mechanism of action for the anti-metastatic and anti-angiogenic activity of contortrostatin. This is the first observation that a disintegrin binds to αvβ5, an important integrin in tumor metastasis and angiogenesis.

Experiment 1. Cell adhesion assay: Human bladder carcinoma T24 cells were purchased from ATCC, and grown in RPMI1640 medium containing 5% fetal bovine serum. T24-β3 neg. cells were isolated by 6 rounds of negative FACS selection with anti-αvβ3 monoclonal antibody (mAb) LM609. FACS analysis was then performed as follows. The cells were resuspended in 1% BSA/PBS at a density of $1\times10^7$/ml. Aliquots of 100 μl were incubated with anti-αvβ3 mAb 7E3 or anti-αvβ5 mAb P1F6 (final concentration 5 μg/ml) at room temperature for 30 minutes. The cells were washed twice and resuspended in 1% BSA/PBS. Goat anti-mouse IgG conjugated with FITC was added to the suspension at a final titer of 1:200. After 30 minutes incubation at room temperature in darkness, unbound FITC-conjugated IgG was washed off, and the fluorescent intensity of the cells was analyzed using flow cytometry (FACScan, Becton Dickinson, Bedford, Mass.). Tests were performed in duplicate and the experiment was repeated three times. The results clearly indicate that T24 cells express both integrins αvβ3 (major) and αvβ5 (minor), but T24-β3 neg. cells only express αvβ5 (FIG. 18)

Individual wells of 96-well plates were coated at 4° C. overnight with 100 μl of vitronectin (1 μg/well). Excess proteins were washed off with three washes of phosphate buffered saline (PBS), followed by blocking with 1% bovine serum albumin (BSA) in PBS. Aliquots (100 μl) of cells ($5\times10^5$ cells/ml) were incubated at room temperature for 20 minutes with antibodies or contortrostatin before being applied to the coated wells. Treated cells were allowed to adhere to the wells for 30 minutes at 37° C. Unbound cells were washed off with serum-free medium. Cell adhesion was quantified either by CellTiter 96™ Aqueous Proliferation Assay kit (Promega, Madison, Wis.). Each inhibitor concentration was tested in triplicate, and assays were performed at least three times yielding identical results.

It was previously demonstrated that contortrostatin inhibits adhesion of human breast cells (MDA-MB-435) on vitronectin coated plate. Integrin αvβ3 was identified as a binding site of the disintegrin in this cell line. Similarly in this study, contortrostatin inhibited adhesion of human bladder carcinoma T24 cells to immobilized vitronectin in a dose-dependent manner, with 100% inhibition at a concentration less than 10 μg/ml (FIG. 18-A). As already shown, FACS analysis indicated that T24 cells express both αvβ3 and αvβ5. While the maximum effect of anti-αvβ3 (7E3) was no higher than 40% at concentrations up to 100 μg/ml (FIG. 19-A), the effect of anti-αvβ5 (P1F6) on adhesion was below 40% at 1:100 dilution (FIG. 19-B). However, the combination of 7E3 (with constant concentration of 10 μg/ml at which maximal inhibition was reached) and increasing concentrations of P1F6 eventually lead to almost 100% inhibition of adhesion. The results suggest that both αvβ3 and αvβ5 mediate the adhesion of T24 cells to vitronectin. Complete elimination of cellular attachment to vitronectin requires combination of antibodies against both integrins. On the other hand, contortrostatin effectively blocks the adhesion of these cell lines to vitronectin. This finding strongly support our hypothesis that contortrostatin binds to αvβ5 as well as αvβ3.

To further distinct the functional blockage by contortrostatin of the two integrins, αvβ3-negative T24 mutant cells (T24-β3 neg.) were employed for the adhesion assay. Although inhibition by 7E3 was negligible, contortrostatin completely inhibited adhesion of the cell line (FIG. 19-C). The adhesion of T24-β3 neg. cells to vitronectin was predominantly mediated by αvβ5, since the inhibitory effect of P1F6 was as high as 80% (FIG. 19-D) in contract with that which is below 40% on T24 cells (FIG. 19-B). The inhibition curve of P1F6 was not altered by addition of 7E3 (FIG. 18-D). The result of this assay indicated that adhesion of the αvβ3 negative cell line T24-P3 is mediated by αvβ5. Blockage of αvβ5 by a monoclonal antibody completely inhibits adhesion. Contortrostatin was shown to be able to prevent adhesion of these cells to vitronectin. Thus, contortrostatin must bind to integrin αvβ5.

Figure 20:
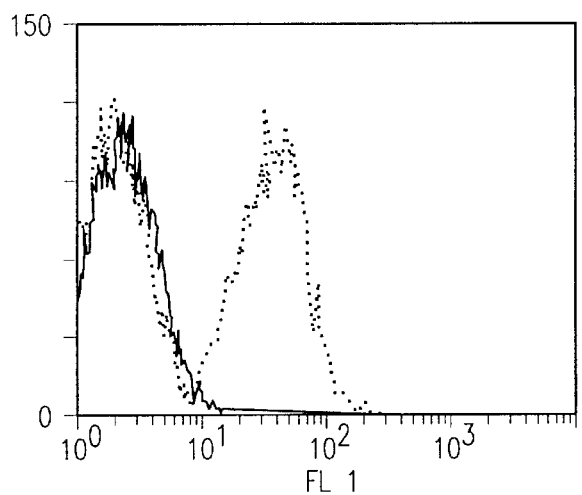
FIG. 20. The expression pattern of integrins in the OVCAR-5 cell line. The expression pattern of integrins in the OVCAR-5 cell line was analyzed by FACS using monoclonal antibodies anti-αvβ3 (7E3) and anti-αvβ5 (P1F6). As shown is FIG. 3, the solid peak is the background, the dotted peak that merges with the background represents bound 7E3, and the dotted peak to the right represents P1F6. This shows conclusively that the OVCAR-5 cells possess integrin αvβ5 but not αvβ3.

Experiment 2. Cell invasion assay: To test whether the binding of contortrostatin to αvβ5 inhibits invasion of cancer cells, invasion assays were performed with highly invasive human ovarian carcinoma cell OVCAR-5, which express αvβ5 but not αvβ3. The expression pattern of integrins in the OVCAR-5 cell line was analyzed by FACS using monoclonal antibodies anti-αvβ3 (7E3) and anti-αvβ5 (P1F6). As shown in FIG. 20, the solid peak is the background, the dotted peak that merges with the background represents bound 7E3, and the dotted peak to the right represents P1F6. This shows conclusively that the OVCAR-5 cells possess integrin αvβ5 but not αvβ3.

Modified Boyden chambers were employed to measure invasion. Filters of 12 mm Boyden chamber with 12 μm pore size (Corning Costar, Cambridge, Mass.) were coated with 1:50 dilution of Matrigel in serum free medium. Cells ($2.5\times10^5$ cells in 200 μl of medium) pre-treated with contortrostatin, antibodies against different integrins, or vehicle (control), were applied to the upper wells. HT1080 conditioned medium was added to the bottom well. The cells were incubated at 37° C. for 8 hr., at which point cells on the top side of the membrane were removed with a wet cotton swab. Cells which invaded through the filter membrane were fixed and stained with Diff-Quik™ staining kit (Dade Diagnostics of P. R. Inc., Aguada, Puerto Rico). The membranes were removed from the holder, and were mounted on slides. Migration was quantitated by determining the number of cells in five randomly selected high power vision field using a microscope. Each inhibitor concentration was tested in duplicate, and the experiments were repeated three times to confirm results.

Figure 21:
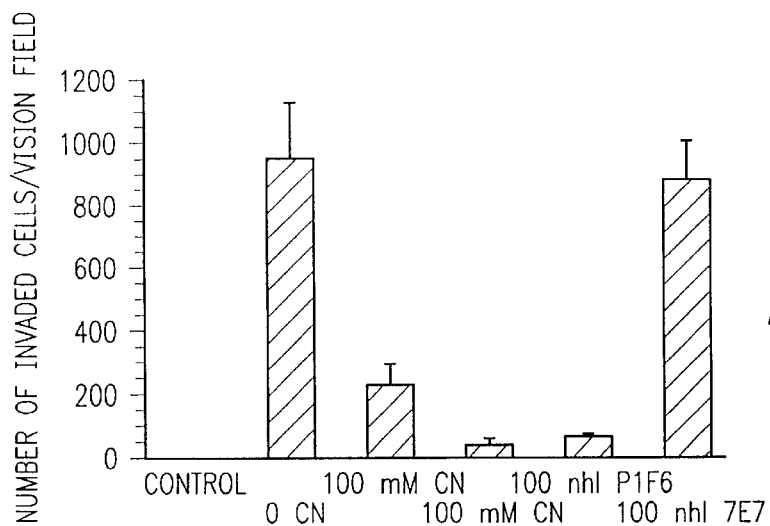
FIG. 21. CN and other antagonists of αvβ5 inhibits adhesion of OVCAR-5 cells to vitronectin. Adhesion of cancer cells to the matrix is one of the critical steps of cancer spreading and metastasis. It is well established that integrin αvβ5 mediates adhesion of cells to vitronectin. In an adhesion assay, we were able to demonstrated that adhesion of OVCAR-5 cells to vitronectin coated plate was inhibited by both CN and mAb against αvβ5 (P1F6). However, anti-αvβ3 (7E3) did not affect cell adhesion. The data suggest that CN, by blocking integrin αvβ5, disrupts adhesion of the cancer cells to vitronectin.

Neither contortrostatin, nor antibodies alone, nor the combination of the antibodies inhibited attachment and spreading of the cells to Matrigel. Therefore, the anti-invasive activities of these vitronectin receptor antagonists were independent of their anti-adhesive effect. FIG. 21 illustrates that contortrostatin (1000 nM) almost completely inhibited invasion of OVCAR-5 cells through Matrigel. Comparable inhibition was achieved with 100 nM of P1F6. However, at the same molar concentration, 7E3 showed no effect on invasion. The results strongly suggested that integrin $\alpha v\beta 5$ mediates invasion of OVCAR-5 cells through Matrigel. Contortrostatin effectively inhibits invasion of these cells due to the blockage of $\alpha v\beta 5$.

Figure 22:
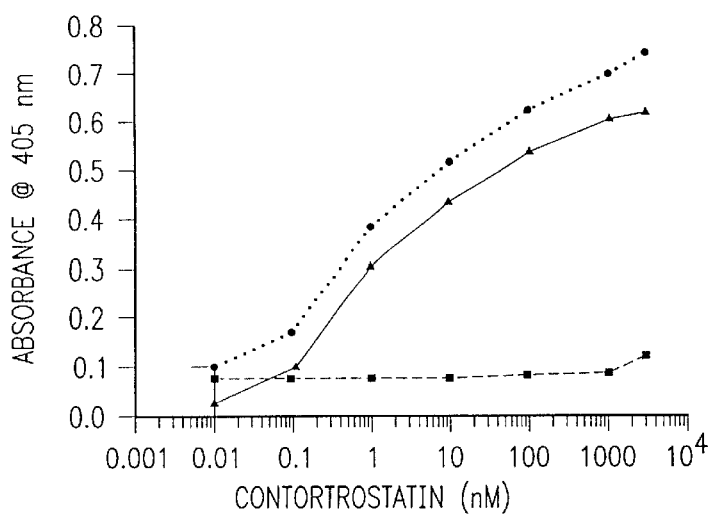
FIG. 22. Direct binding of contortrostatin to purified αvβ5: Purified αvβ5 (100 ng) immobilized in individual wells of microtiter plates. Contortrostatin at various concentration was allowed to bind to the integrin. Bound contortrostatin was quantitated using anti-serum against the disintegrin as the total binding (solid circles). Contortrostatin bound to bovine serum albumin is defined as the non-specific binding (opened squares). The specific binding (triangles) is calculated by subtraction of the non-specific binding from the total binding. Each point represents mean absorbance at 405 nm±SD from triplicate analyses. The experiment was repeated to confirm results.

Experiment 3: Detection of the binding of contortrostatin to $\alpha v\beta 5$: Direct evidence that contortrostatin binds to $\alpha v\beta 5$ was collected by solid-phase binding assay using purified $\alpha v\beta 5$ and a modified ELISA. Soluble $\alpha v\beta 5$ (100 ng) was immobilized on wells of a 96-well plate at 4° C. overnight. Excess protein was washed off, and unbound sites were blocked with 1% BSA/PBS. Contortrostatin at various concentrations was allowed to bind to the coated plate at room temperature for one hour. After three washes with PBS, the bound contortrostatin molecules were detected with 1:1,000 antiserum against contortrostatin. Goat anti-rabbit antibody conjugated with alkaline phosphotase was used as a secondary antibody. The bound antibodies were quantitated by applying substrate disodium p-nitrophenyl phosphate (pNPP) and determining the light absorbance at 405 nm 15 minutes after the initiation of the chromagenic reaction. The background is defined by the binding of antiserum against the disintegrin to immobilized $\alpha v\beta 5$. Specific binding is obtained by substrating the background from the total binding. Analyses of each concentration of ligand were performed in triplicate. FIG. 22 indicates that contortrostatin binds to $\alpha v\beta 5$ in a dose-dependent and saturable manner, suggesting that contortrostatin specifically binds to $\alpha v\beta 5$.

In summary, we identified $\alpha v\beta 5$ as a novel binding site for the disintegrin contortrostatin. Functional blockade of $\alpha v\beta 5$ not only inhibits the adhesion of cancer to vitronectin, but also blocks invasion of cancer cells through Matrigel artificial basement membrane. Binding of contortrostatin to $\alpha v\beta 5$ is most likely part of its anti-adhesion and anti-invasion activity.

Example 15

Contortrostatin Induces $\alpha v\beta 3$-Mediated Tyrosine Phosphorylation of CAS and FAK in Tumor Cells Summary: Contortrostatin is a homodimeric disintegrin that inhibits platelet aggregation and cell adhesion to extracellular matrix proteins by blocking integrins. The effect of contortrostatin on integrin-mediated signaling in tumor cells was investigated by studying tyrosine phosphorylation events and activation of specific signaling molecules. We found that at concentrations as low as 1 nM, soluble contortrostatin activates integrin signals leading to increased tyrosine phosphorylation of FAK and CAS, and that these signals are abolished by inhibiting Src activity. Using transfected 293 cells expressing specific integrins, we determined that contortrostatin-generated signals are mediated exclusively by the $\alpha v\beta 3$ integrin. This observation was extended by showing that cells lacking $\alpha v\beta 3$ but expressing $\alpha v\beta 5$ and $\alpha 5\beta 1$, do not respond in this way to contortrostatin treatment. In cells expressing $\alpha v\beta 3$, blocking contortrostatin binding with antibodies against $\alpha v\beta 3$ completely abrogates contortrostatin signals. Monovalent disintegrins echistatin and flavoridin were incapable of affecting tyrosine phosphorylation alone, but when added simultaneously with contortrostatin, completely inhibited contortrostatin-initiated signals. We propose that the homodimeric nature of contortrostatin imparts the ability to crosslink $\alpha v\beta 3$ integrins, causing Src activation and hyperphosphorylation of FAK and CAS. This activity may represent a novel mechanism by which tumor cell motility can be inhibited.

Introduction: Much of what is known about integrin signaling is the product of studies carried out in platelets (Huang, M. -M., Lipfert, L., Cunningham, M., Brugge, J. S., Ginsberg, M. H., and Shattil, S. J. (1993) *J. Cell Biol.* 122(2), 473–483), fibroblasts and epithelial cell lines (Schlaepfer, D. D., and Hunter, T. (1998) *Trends Cell Biol.* 8, 151–157; and Giancotti, F. G., and Ruoslahti, E. (1999) *Science* 285, 1028–1032). Significant progress has been made in the area of integrin-mediated signaling and the role of integrins in cell motility, but this area remains understudied in tumor cells. Focal adhesion kinase (FAK) is a non-receptor tyrosine kinase that localizes with integrins and is phosphorylated on tyrosine residues upon cellular adhesion to the extracellular matrix (ECM) (Burridge, K., Turner, C. E., and Romer, L. H. (1992) *J. Cell Biol.* 119, 893–903). FAK plays an important role in allowing integrins, which lack catalytic activity, to convert extracellular stimuli into intracellular signals. Cell binding to the ECM causes integrin clustering and association of a number of cytoskeletally associated proteins into complexes known as focal adhesions (Burridge, K., Fath, K., Kelly, T., Nuckolls, G., and Turner, C. (1988) Annu. Rev. Cell Biol. 4, 487–525). FAK associates with the cytoplasmic domains of the $\beta$ integrin subunits and can undergo trans-autophosphorylation at specific tyrosine residues, creating a binding site for the Src family of protein tyrosine kinases (Schaller, M. D., Hildebrand, J. D., Shannon, J. D., Fox, J. X., Vines, R. R., and Parsons, J. T. (1994) *Mol. Cell. Biol.* 14, 1680–1688). Src then can phosphorylate tyrosines in the FAK activation loop, resulting in full catalytic activity. The function of FAK is complex and is not yet fully appreciated, however a role of FAK in cell migration has recently been established. Overexpressing FAK in CHO cells leads to enhanced migration (L., Chang, J., and Guan, J.-L. (1996) J. Cell Sci. 109, 1787–1794), and association of the adapter protein CAS via its SH3 domain with the proline-rich region of FAK mediates this enhancement (Cary, L. A., Han, D. C., Polte, T. R., Hanks, S. K., and Guan, J.-L. (1998) J. Cell Biol. 140(1), 211–221). In addition to its SH3 domain, CAS contains multiple tyrosine residues that undergo phosphorylation in response to cell adhesion to the ECM, and this phosphorylation is dependent on FAK and Src (K., Hirai, H., Aizawa, S., and Rouslahti, E. (1996) *Mol. Cell. Biol.* 16(6)). CAS is bound by SH2-domain containing proteins Crk and Nck. The CAS/Crk complex has been shown to serve as a "molecular switch" in the regulation of motility in carcinoma cells (Klemke, R. L., Leng, J., Molander, R., Brooks, P. C., Vuori, K., and Cheresh, D. A. (1998) *J. Cell Biol.* 140(4), 961–972). Thus, FAK and CAS are important participants in integrin signaling and in the regulation of motility.

The disintegrins are a family of snake venom proteins that were first identified as inhibitors of platelet aggregation by virtue of their ability to block fibrinogen binding to the $\alpha IIb\beta 3$ integrin (Huang, T.-F., Holt, J. C., Lukasiewicz, H., and Niewlarowski, S. (1987) *J. Biol. Chem.* 262, 16157–16163). This interaction was shown to be dependent on the RGD (Arg-Gly-Asp) sequence present in the C-terminal half of the disintegrins. This sequence is also found in fibrinogen and extracellular matrix proteins. The disintegrins are also characterized by the presence of highly conserved cysteine residues that are critical to maintaining the structure and activity of these molecules through disulfide bonds. Disintegrins have subsequently been shown to block cell adhesion to various ECM components by binding to different β1 and β3 integrins on various cell types (Niewiarowski, S., McLane, M. A., Kloczewiak, M., and Stewart, G. (1994) *Seminars in Hematology* 31(4), 289–300). A subfamily is emerging which includes several dimeric disintegrins with varying integrin binding specificities. All previously described disintegrins contain the tripeptide sequence RGD or KGD, but the recently described heterodimeric disintegrin EC3, has VGD in the EC3A subunit and MLD in the EC3B subunit substituted into this position (Marcinkiewicz, C., Calvete, J. J., Marcinkiewicz, M. M., Raida, M., Vijay-Kumar, S., Huang, Z., Lobb, R. R., and Niewiarowski, S. (1999) *J. Biol. Chem.* 274(18), 12468–12473).

We previously described the isolation of a distinct member of the growing family of dimeric disintegrins (Trikha, M., Rote, W., Manley, P., Lucchesi, B. R., and Markland, F. S. (1994) *Thrombosis Research* 73, 39–52). Contortrostatin, purified from the venom of *Agkistrodon contortrix contortrix* has a molecular weight of 13.5 kDa and is unique since it contains two identical 6.75 kDa subunits (Trikha, M., De Clerck, Y. A., and Markland, F. S. (1994) *Cancer Research* 54, 4993–4998). Each subunit contains an RGD motif and 10 cysteines at conserved positions. However, contortrostatin appears to have a truncation at the amino terminus and lacks two cysteines present in other monomeric disintegrins. EC3 similarly lacks these two amino-terminal cysteines (Marcinkiewicz et al., supra), suggesting that the dimeric structure is a result of the absence of these residues which leaves cysteines elsewhere in the protein available for interchain disulfide bond formation. Contortrostatin was shown to inhibit adhesion of melanoma cells to type I collagen, vitronectin and fibronectin (Trikha et al.,(1994) *Cancer Research*, supra), and we are currently studying the antitumor and antiangiogenic properties of this disintegrin. Contortrostatin was found to inhibit human platelet aggregation and to block binding of an anti-αIIbβ3 antibody to platelets. Importantly, in addition to its ability to block aggregation, contortrostatin caused an increase in tyrosine phosphorylation of a subset of platelet proteins (Clark, E. A., Trikha, M., Markland, F. S., and Brugge, J. S. (1994) *J. Biol. Chem.* 269(35), 21940–21943). This activity distinguished contortrostatin from a monomeric disintegrin which blocked platelet aggregation but was unable to induce protein tyrosine phosphorylation. These findings led to further investigations into the functional consequences of contortrostatin structure and prompted a study of the role of contortrostatin in regulating integrin-mediated signaling in tumor cells. Here we report that contortrostatin has the unique ability to act as an integrin agonist by stimulating αvβ3-mediated tyrosine phosphorylation of important signaling molecules in tumor cells, an activity not found in monomeric disintegrins.

Experimental Procedures

Materials—MDA-MB-435 human mammary carcinoma cells were obtained from Janet Price (M. D. Anderson Cancer Center Houston, Tex.). T24 human bladder carcinoma cells[2] were purchased from ATCC (Manassas, Va.). 293 human embryonic kidney cells transfected with cDNA for β3 and β5 integrin subunits and parental 293 cells were provided by Dr. Jeffrey Smith (The Burnham Institute, La Jolla, Calif.)(Lin, E. C. K., Ratnikov, B. I., Tsai, P. M., Carron, C. P., Myers, D. M., Barbas, C. F., and Smith, J. (1997) *J. Biol. Chem.* 272(38), 23912–23920). OVCAR-5 human ovarian carcinoma cells were from Dr. Thomas Hamilton (Fox Chase Cancer Center, Philadelphia, Pa.). Contortrostatin was purified from the venom of the southern copperhead (*Agkistrodon contortrix contortrix*) as described previously (Trikha et al., (1994) *Thrombosis Research*, supra; and Trikha et al., (1994) *Cancer Research*, supra). The monomeric disintegrins echistatin and flavoridin, and the general protease inhibitor cocktail used in lysis buffers were obtained from Sigma (St. Louis, Mo.). Vitronectin was purchased from Becton Dickinson (Bedford, Mass.). PPI Src inhibitor was from Calbiochein (La Jolla, Calif.). Anti-phosphotyrosine monoclonal antibody (mAb) PY99 was obtained from Santa Cruz Biotechnology (Santa Cruz, Calif.). Anti-FAK and anti-CAS mAbs were purchased from Transduction Laboratories (Lexington, Ky.) and 7E3 mAb was provided by Centocor (Malvern, Pa.).

Cell culture, preparation and stimulation—T24 cells were maintained in RPMI 1640 medium containing 5% fetal bovine serum, and MDA-MB-435 and 293 cells were maintained in Dulbecco's modified Eagle's medium with 10% serum at 37° C. in 5% $CO_2$. Cells were washed with phosphate-buffered saline (PBS) and starved in the appropriate serum-free medium for 6 h at 37° C. Cells were detached by brief treatment with 0.05% trypsin/0.02% EDTA in PBS and collected by centrifugation, resuspended in soybean trypsin inhibitor (1 mg/ml in serum-free medium), and washed in 2% bovine serum albumin/serum-free medium. Cells were maintained in suspension for 1 h in 2% bovine serum albumin/serum-free medium at 37° C. with end-over-end agitation. Quiescent cells ($3 \times 10^6$/ml) were treated with disintegrins or other reagents while in suspension, or were allowed to adhere to Matrigel (Becton Dickinson, Bedford, Mass.) diluted 1:100 with serum-free medium during treatment.

Lysate preparation and immunoprecipitation—Suspended and adherent cells were washed twice with cold PBS and lysed in cold lysis buffer (50 mM Tris, pH 8.0, 150 mM NaCl, 1% Nonidet P-40, 0.5% deoxycholate, 0.1% SDS, protease inhibitor cocktail, 1 mM sodium pyrophosphate, 1 mM sodium orthovanadate, 50 mM sodium fluoride). After 10–15 min incubation on ice, insoluble material was removed by centrifugation at 14,000 RPM in a microcentrifuge for 15 min. Supernatants were collected and total protein concentrations standardized by the BCA protein assay (Pierce, Rockford, Ill.). Immunoprecipitation was carried out by incubating whole cell lysates (200 μg total protein) with 1.25 μg anti-FAK or anti-CAS mAb 4–6 h at 4° C. followed by 20 μl protein G-agarose overnight at 4° C. Immunoprecipitates were washed 4 times in lysis buffer without inhibitors and dissociated by adding SDS-PAGE sample buffer and boiling 5 min. Whole cell lysates (30 μg total protein) or immunoprecipitates were resolved by 7.5% SDS-polyacrylamide gel electrophoresis and transferred to nitrocellulose membranes.

Immunoblotting—Membranes were blocked with 5% nonfat milk/Tris-buffered saline/0.1% Tween 20 (blocking buffer) 1 h at room temperature or overnight at 4° C. Primary antibody incubations were performed in blocking buffer for 1 h at room temperature. After washing in Tris-buffered saline/0.1% Tween 20, membranes were incubated with horseradish peroxidase-conjugated secondary antibody in blocking buffer 1 h at room temperature. Membranes were washed extensively. Inimunoblots were developed using Super Signar West Pico Chemiluminescent Substrate from Pierce. Densitometry was performed using UN-SCAN-IT™, software (Silk Scientific, Orem, Utah))

Figure 23:
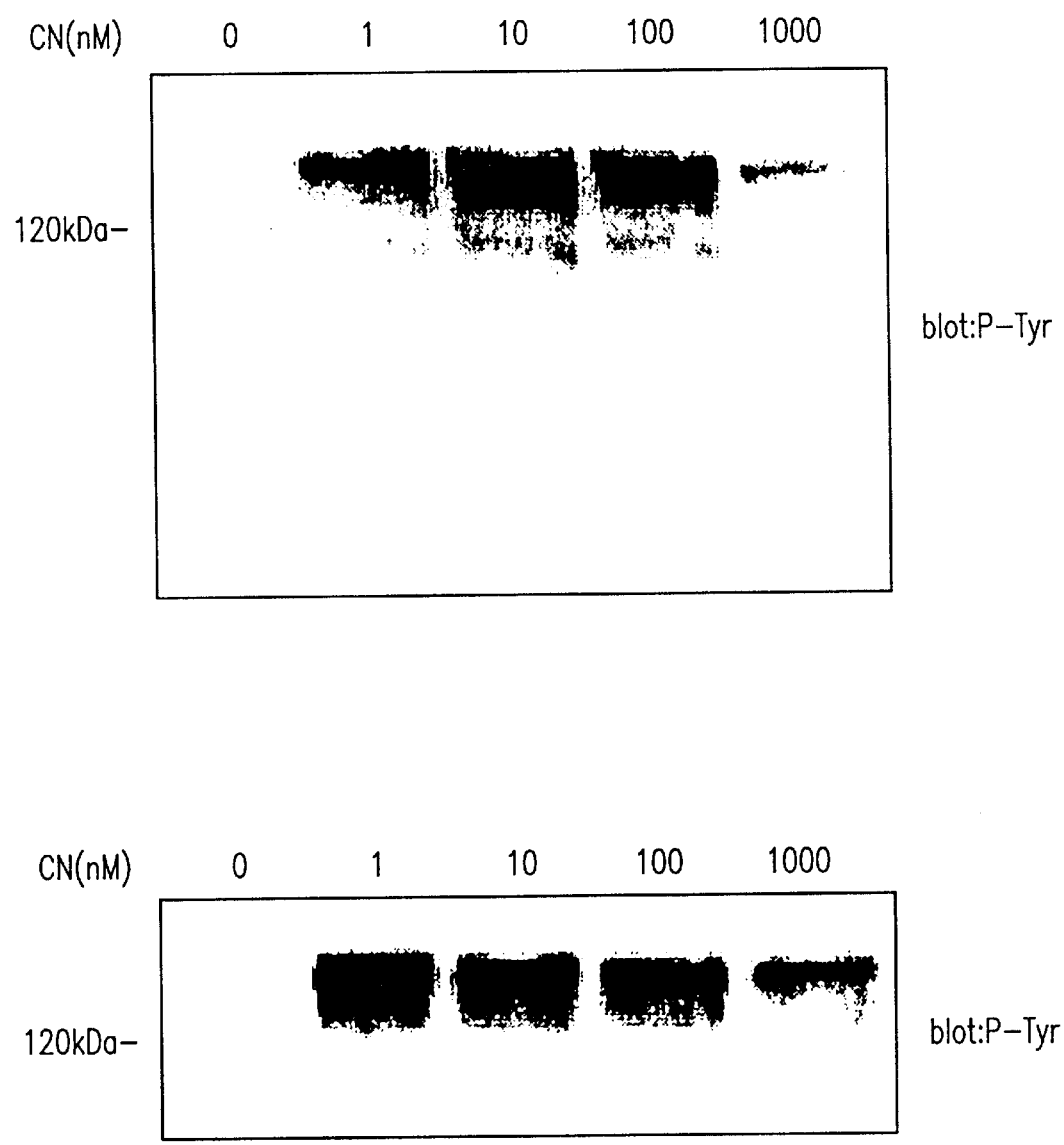
FIG. 23. Phosphotyrosine levels in tumor cells after contortrostatin treatment. MDA-MB-435 cells (upper panel) or T24 cells (lower panel) were treated in suspension with the indicated concentrations of contortrostatin (CN) for 10 min. Whole cell lysates (30~tg total protein) were subjected to SDS-PAGE and immunoblotting with antibody against phosphotyrosine (PY99) as described in Experimental Procedures.

Results:

Contortrostatin treatment induces protein tyrosine phosphorylation in tumor cells—To investigate the role of contortrostatin in regulating overall tyrosine phosphorylation in tumor cells, MDA-MB-435 human breast carcinoma cells were treated for 10 min with various concentrations of soluble contortrostatin while in suspension. The cells showed a dramatic increase in tyrosine phosphorylation of proteins with molecular weights from 120–140 kDa following contortrostatin treatment (FIG. 23). Maximal levels of tyrosine phosphorylation were observed at 10 nM contortrostatin. Tyrosine phosphorylation of proteins in this size range was also observed in T24 human bladder carcinoma cells (FIG. 23) and KSY-1 Kaposi's sarcoma cells (data not shown) following contortrostatin treatment using the same methods, indicating that this phenomenon is not cell-type specific.

Monomeric disintegrins, echistatin and flavoridin, do not induce tyrosine phosphorvlation in tumor cells—In an effort to determine whether the ability to stimulate tyrosine phosphorylation in tumor cells was related to the homodimeric structure of contortrostatin, we tested two well-characterized monomeric disintegrins, echistatin (Gan, Z. R., Gould, R. J., Jacobs, J. W., Friedman, P. A., and Polokoff, M. A. (1988) *J. Biol. Chem.* 263, 19827–19832) and flavoridin (Niewiarowski et al., supra), for their ability to affect integrin signaling in suspended MDA-MB-435 cells. In sharp contrast to the observed effects of contortrostatin, the monomeric disintegrins alone had no effect on tyrosine phosphorylation at concentrations up to 1 $\mu$M. However, when echistatin or flavoridin (1 $\mu$M) were added simultaneously with contortrostatin (10 nM), contortrostatin-induced tyrosine phosphorylation was completely abrogated (FIG. 24). These findings indicate that the monomeric disintegrins competitively inhibit contortrostatin binding to specific signal-generating integrins.

Contortrostatin- induced signaling events are mediated by the $\alpha v\beta 3$ integrin—The integrinbinding specificities of echistatin and flavoridin have been determined previously (Niewiarowski et al., supra; and Pfaff, M., McLane, M. A., Beviglia, L., Niewiarowski, S., and Timpl, R. (1994) *Cell Adhesion and Communication* 2, 491–501). Both monomeric disintegrins interact $\alpha IIb\beta 3$, $\alpha v\beta 3$ and $\alpha 5\beta 1$. We have shown that contortrostatin binds these same integrins (Trikha et al., (1994) *Thrombosis Research*, supra; Trikha et al.,(1994) *Cancer Research*, supra; and Markland, F. S., and Zhou, Q. (1999) in *Natural and Synthetic Toxins: Biological Implications* (Tu, A. T., and Gaffield, W., eds), pp. Chapter 18, American Chemical Society, Washington D.C.; incorporated herein in its entirety by reference), as well as $\alpha v\beta 5$. With the knowledge that $\alpha IIb\beta 3$ is not expressed on MDA-MB-435 cells, as shown by a lack of staining with 10E5, a specific anti-$\alpha IIb\beta 3$ mAb (data not shown), this implicated $\alpha v\beta 3$, $\alpha 5\beta 1$ or both, in contortrostatin-induced signaling events, based on the monomeric disintegrin versus contortrostatin observations presented above. In order to determine which receptor(s) was involved, we employed transfected 293 cell lines with specific integrin profiles (Lin et al., supra). The parental 293 cells express the $\alpha v$ subunit but have no detectable $\alpha v\beta 3$ and only trace levels of $\alpha v\beta 5$ expression. Cells transfected with cDNAs encoding the $\beta 3$ or $\beta 5$ integrin subunits show significant levels of the $\alpha v\beta 3$ or $\alpha v\beta 5$ heterodimers, respectively (Lin et al., supra). Integrin expression was confirmed in our laboratory by flow cytometry. When these cell lines are treated with contortrostatin using established methods, only the $\alpha v\beta 3$-expressing cells show the robust induction of tyrosine phosphorylation observed in other cell types (FIG. 25A). Importantly, the proteins undergoing tyrosine phosphorylation in the $\beta 3$ transfected cells are in the 120–140 kDa range, the same molecular weights as those observed in other cell lines tested. These findings demonstrate the involvement of $\alpha v\beta 3$ in contortrostatin signaling but do not directly address the potential contribution of $\alpha 5\beta 1$, since echistatin and flavoridin are known to bind $\alpha 5\beta 1$. This possibility was ruled out by studies using 7E3, a mAb generated against $\alpha IIb\beta 3$ that has equal affinity for $\alpha v\beta 3$ (Tain, S. H., Sassoli, P. M., Jordan, R. E., and Nakada, M. T. (1998) *Circulation* 98(11), 1085–1091). Contortrostatin-induced tyrosine phosphorylation was completely blocked when MDA-MB-435 cells, which express $\alpha v\beta 3$, $\alpha v\beta 5$ and $\alpha 5\beta 1$ (Wong, N. C., Mueller, B. M., Barbas, C. F., Ruminski, P., Quaranta, V., Lin, E. C., and Smith, J. W. (1998) *Clinical Exp. Metastasis* 16(1), 50–61; and Chandrasekaran, S., Guo, N.-h., Rodrigues, R. G., Kaiser, J., and Roberts, D. D. (1999) *J. Biol. Chem.* 274(16), 11408–11416), are treated simultaneously with 1 $\mu$M 7E3 and 10 nM contortrostatin for 10 min (FIG. 25B, lower panel). This result was duplicated in T24 cells (FIG. 25B, upper panel), providing convincing evidence that $\alpha v\beta 3$ is solely responsible for mediating contortrostatin-induced tyrosine phosphorylation. Further proof of this finding is found in OVCAR-5, a human ovarian carcinoma cell line that is negative for $\alpha v\beta 3$ expression but expresses $\alpha v\beta 5$ and $\alpha 5\beta 1$. These cells do not show significant enhancement of tyrosine phosphorylation when treated with contortrostatin (data not shown). Thus, despite the ability to interact with other integrins, contortrostatin induces protein tyrosine phosphorylation in tumor cells exclusively via the $\alpha v\beta 3$ integrin.

Contortrostatin binding to $\alpha v\beta 3$ results in tyrosine phosphorylation of CAS and FAK—In order to identify the specific proteins that are tyrosine phosphorylated in response to contortrostatin treatment, lysates prepared from contortrostatin-treated cells were subjected to immunoprecipitation with CAS or FAK monoclonal antibodies followed by anti-phosphotyrosine immunoblotting. CAS and FAK were selected as likely candidates based on the similarity of their molecular weights (130 and 125 kDa, respectively) with those observed on the anti-phosphotyrosine immunoblots with whole cell lysates. We found that CAS and FAK are both tyrosine phosphorylated in response to contortrostatin treatment (FIG. 26), and immunoprecipitated CAS and FAK co-migrate with the major bands observed after anti-phosphotyrosine immunoblot with whole cell lysates, indicating that these are the major proteins phosphorylated by contortrostatin treatment.

Figure 27:
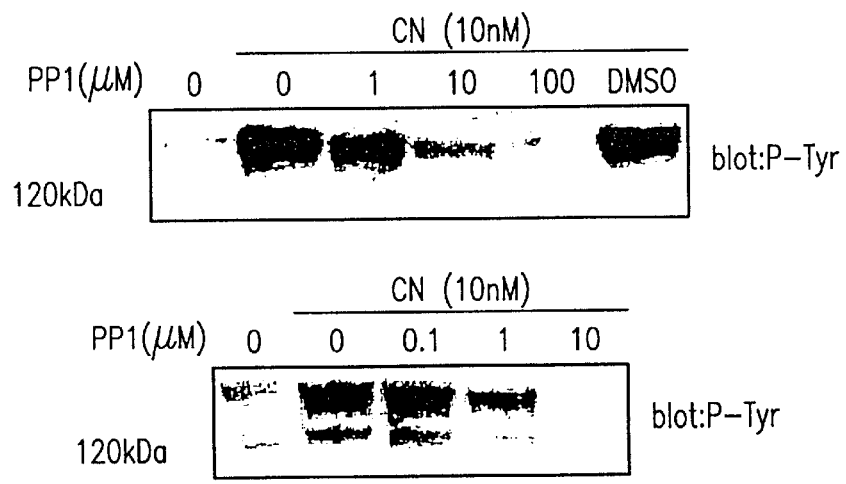
FIG. 27. Involvement of Src in contortrostatin-induced tyrosine phosphorylation. T24 cells (upper panel) or MDA-MB-435 cells (lower panel) were pretreated with the indicated concentrations of the Src inhibitor PPI for 30 min prior to stimulation with 10 nM contortrostatin (CN). Lysates were prepared and analyzed by anti-phosphotyrosine immunoblot. Stock solutions of PPI are prepared in DMSO, but DMSO alone had no effect on contortrostatin-induced tyrosine phosphorylation (upper panel).

Src activity is necessary for contortrostatin-induced tyrosine phosphorylation events—The Src tyrosine kinase is known to play a central role in integrin signaling, In order to determine if Src participates in transmitting contortrostatin-induced signals from $\alpha v\beta 3$, T24 cells were pretreated in suspension for 30 min with the Src family inhibitor, PP1 (Hanke, J. H., Gardner, J. P., Dow, R. L., Changelian, P. S., Brisette, W. H., Weringer, E. J., Pollok, B. A., and Connelly, P. A. (1996) *J. Biol. Chem.* 271(2), 695–701), prior to stimulation with 10 nM contortrostatin. As shown in FIG. 27 (upper panel), PP1 demonstrates a dose-dependent inhibition of tyrosine phosphorylation with complete elimination of contortrostatin-induced signals at a concentration of 100 $\mu$M. Similar results were obtained following PP1 treatment of MDA-MB-435 cells, although complete inhibition was achieved at 10 μM PP1 (FIG. 27, lower panel). These findings confirm the involvement of Src in integrin signaling stimulated by contortrostatin.

Figure 28:
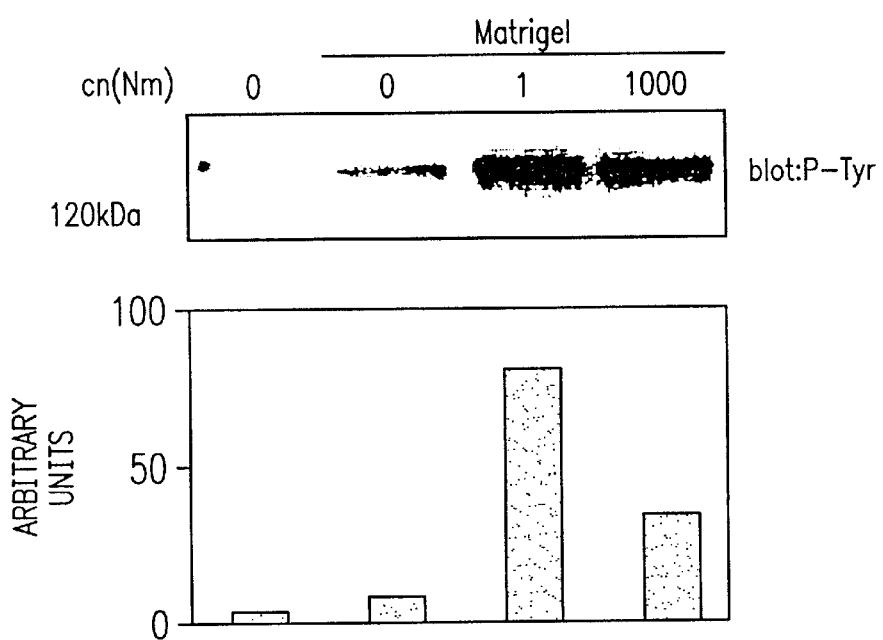
FIG. 28. Contortrostatin-induced tyrosine phosphorylation is independent of cellular adhesion. T24 cells were pretreated with the indicated concentrations of contortrostatin (CN) for 5 min prior to addition to Matrigel-coated plates. Control cells were maintained in suspension. Lysates were prepared after incubating cells on Matrigel for 20 min and analyzed by anti-phosphotyrosine immunoblot (upper panel). The lower panel shows the relative intensity of the corresponding bands as detennined by densitometry.

Contortrostatin-induced tyrosine phosphorylation is independent of cellular adhesion—In order to determine if contortrostatin is able affect tyrosine phosphorylation in adherent cells where integrin ligation and cytoskeletal structure exist, T24 cells were pretreated with contortrostatin before allowing them to adhere to Matrigel-coated plates. It should be noted that contortrostatin does not significantly inhibit cellular binding to laminin. Therefore, contortrostatin does not inhibit cellular binding to Matrigel, which is rich in laminin. Phosphotyrosine immunoblotting revealed that T24 cells showed modest increases in tyrosine phosphorylation after adhesion to Matrigel, but contortrostatin treatment of adherent cells causes a significant additional increase in these signals, including the 120–140 kDa bands shown to contain CAS and FAK (FIG. 28). It was again observed that high concentrations of contortrostatin (1000 nM) generated reduced levels of tyrosine phosphorylation. In similar experiments, T24 cells were allowed to adhere to Matrigel for 30 min prior to treatment with contortrostatin. Following an additional 30 min incubation on Matrigel in the presence of contortrostatin, cells showed similar increased tyrosine phosphorylation of the 120–140 kDa bands. Thus, contortrostatin induction of tyrosine phosphorylation can occur in adherent cells, in the presence of stimuli from ECM proteins, as well as in non-adherent cells.

Discussion: Since their discovery, disintegrins have been have been studied almost exclusively for their ability to block the function of various integrins. Disintegrins have been used extensively to investigate the function of αIIbβ3 on platelets, and more recent work has been conducted with endothelial cells in the study of the role of αvβ3 in angiogenesis (Kang, I.-C., Lee, Y.-D., and Kim, D.-S. (1999) *Cancer Research* 59, 3754–3760; Shen, J.-R., Yen, M.-H., Kan, Y.-C., Hung, W.-C., Chang, P.-T., and Luk, H.-N. (1997) *Biochim. Biophys. Acta* 1336, 445–454; and Yeh, C. H., Peng, H.-C., and Huang, T.-F. (1998) *Blood* 92(9), 3268–3276). In these reports, the antiangiogenic effects of the disintegrins are described to be a function of their ability to block αvβ3 an integrin which has been shown to be involved in induction of endothelial cell apoptosis (Brooks, P. C., Montgomery, A. M. P., Rosenfeld, M., Reisfeld, R. A., Hu, T., Klier, G., and Cheresh, D. A. (1994) *Cell* 79, 1157–1164). However, the direct effects of disintegrins on integrin-mediated signaling remains largely unstudied. In one report, echistatin was shown to cause a decrease in FAK phosphorylation and disassembly of focal adhesions prior to melanoma cell detachment from fibronectin (Staiano, N., Garbi, C., Squillacioti, C., Esposito, S., Di Martino, E., Belisario, M. A., Nitsch, L., and Di Natale, P. (1997) *Eur. J. Cell Biol.* 73, 289–305). In contrast to these descriptions of disintegrins as passive integrin-blocking agents, the present work shows that the disintegrin, contortrostatin, has a structure that enables it to function as an integrin agonist, initiating signals that are usually observed only after cellular binding to natural ECM ligands or artificial crosslinking with anti-integnin antibodies. Our results suggests that contortrostatin actively regulates the function αvβ3 in tumor cells. The effects of contortrostatin on integrin signaling have been studied previously in platelets where it was found that the contortrostatin dimer and the monomeric disintegrin, multisquamatin, both inhibited αIIbβ3-mediated platelet aggregation and aggregation-dependent tyrosine phosphorylation of numerous proteins including FAK (Clark et al., supra). A distinct set of platelet proteins have been shown to become tyrosine phosphorylated upon αIIbβ3 crosslinking with fibrinogen or αIIbβ3 antibodies (1). Contortrostatin was shown to activate tyrosine phosphorylation of these same proteins, presumably by virtue of its dimeric structure. However, there are notable differences between the present study and the work performed in platelets, particularly the tyrosine phosphorylation status of FAK following contortrostatin treatment. This discrepancy is likely the result of differences in the regulatory mechanisms of FAK tyrosine phosphorylation in platelets and tumor cells. In platelets, FAK phosphorylation is dependent on platelet aggregation, and does not occur after fibrinogen binding to αIIbβ3 alone, indicating that events occurring during platelet—platelet aggregation, and not integrin crosslinking, are critical in regulating FAK phosphorylation (Lipfert, L., Haimovich, B., Schaller, M. D., Cobb, B. S., Parsons, J. T., and Brugge, J. S. (1992) *J. Cell Biol.* 119 (4), 905–912). In contrast, studies in fibroblasts show that FAK undergoes tyrosine phosphorylation after integrin aggregation with non-inhibitory mAbs in the absence of integrin ligation (Miyarnota, S., Akiyama, S. K., and Yamada, K. M. (1995) *Science* 267, 883–885). Thus, simple dimerization of integrins is sufficient to cause FAK phosphorylation in fibroblasts, and this mechanism is expected to function through αvβ3 crosslinking during contortrostatin-induced signaling in tumor cells.

From the observations presented in this report, we propose that each subunit of contortrostatin binds to a separate αvβ3 integrin, bringing the integrins into close proximity allowing trans-autophosphorylation of integrin-associated FAK, creating a binding site for Src (Schaller et al., supra). Binding of Src leads to further tyrosine phosphorylation of FAK (Schlaepfer, D. D., and and Hunter, T. (1996) *Mol. Cell. Biol.* 16, 5623–5633) and to Src-mediated phosphorylation of CAS (Hirai et al., supra). We observed in this study that at higher concentrations of contortrostatin (1 μM), the levels of tyrosine phosphorylation decreased. This apparent paradox might be explained when taking into account two possible binding orientations of the contortrostatin dimer. At low concentrations, each of the two subunits is bound to a different integrin on a single cell, bringing them into close proximity and allowing for the initiation of signaling cascades. At high concentrations, only one of the two subunits is bound to αvβ3 on a cell, and integrin clustering will not occur. Under these conditions, contortrostatin acts as a monovalent ligand, and will not initiate tyrosine phosphorylation. Therefore, when contortrostatin concentrations are above saturating levels, the "monomeric" binding orientation will dominate and a reduction in tyrosine phosphorylation will be observed. In another study, soluble monomeric and multimeric vitronectin were studied for their ability to differentially regulate tyrosine phosphorylation in bovine pulmonary artery endothelial cells (Bhattacharya, S., Fu, C., Bhattacharya, J., and Greenberg, S. (1995) *J. Biol. Chem.* 270(28), 16781–16787). Multimeric vitronectin was shown to mediate enhanced tyrosine phosphorylation of several proteins, including FAK, yet monomeric vitronectin did not produce this effect. This finding was confirmed in our studies with MDA-MB-435 cells in which monomeric vitronectin failed to stimulate tyrosine phosphorylation at 10 μg/ml (data not shown). These studies support our findings that contortrostatin possesses the ability to initiate αvβ3-mediated signaling by crosslinking integrins at the surface of tumor cells, resulting in dramatic stimulation of tyrosine phosphorylation of the important signaling molecules FAK and CAS. Attention has been directed to these two molecules recently with respect to their roles in cell motility, and their physiological importance has been highlighted in a report investigating the role of a protein tyrosine phosphatase, PTP-PEST (Angers-Loustau, A., Cote, J.-F., Charest, A., Dowbenko, D., Spencer, S., Lasky, L. A., and Tremblay, M. L. (1999) *J. Cell Biol.* 144(5), 1019–1031). Fibroblasts lacking expression of PTP-PEST show severe defects in motility. Biochemical and immunocytochernical analysis revealed that this defect was due in part to a constitutive increase in tyrosine phosphorylation of CAS, FAK, and paxillin and to an increase in the number of focal adhesions present. CAS is a known PTP-PEST substrate and paxillin has been shown to associate with PTP-PEST in vitro. It is not clear why FAK is hyperphosphorylated in these cells, but the effects of FAK on cell migration are known to be dependent on CAS (Cary et al., supra). Although PTP-PEST and contortrostatin produce their effects through entirely different mechanisms, the end result of CAS and FAK hyperphosphorylation is very similar. These similarities suggest a functional consequence of tumor cell treatment with contortrostatin where a disruption, through αvβ3-mediated hyperphosphorylation of CAS and FAK, occurs in the delicate and highly regulated machinery that drives cell motility. Since cell motility depends on both the assembly and disassembly of focal adhesions, this disruption can result in decreased breakdown of focal adhesions and inhibited motility. The involvement of αvβ3 and FAK in tumor cell motility is emphasized in a recent report showing that the presence of αvβ3 on human prostatic carcinoma cells generated a migratory phenotype that is modulated by pathways involving FAK (Zheng, D.-Q., Woodard, A. S., Fornaro, M., Tallini, G., and Languino, L. R. (1999) *Cancer Research* 59, 1655–1664). In addition to its involvement in motility, αvβ3 has been shown to be critical to other events in tumor progression, including localization of MMP-2 and degradation of the surrounding matrix (Brooks, P. C., Stromblad, S., Sanders, L. C., von Schalscha, T. L., Aimes, R. T., Stetler-Stevenson, W. G., Quigley, J. P., and Cheresh, D. A. (1996) *Cell* 185, 683–693), and in tumor-induced angiogenesis (Brooks et al., (1994) *Cell*, supra; and Brooks, P. C., Clark, R. A., and Cheresh, D. A. (1994) *Science* 264, 569–571). The notion of inappropriate tyrosine phosphorylation and activation of signaling molecules resulting in inhibition of cell migration has been suggested previously (Claesson-Welsh, L., Welsh, M., Ito, N., Anand-Apte, B., Soker, S., Zetter, B., O'Reilly, M., and Folkman, J. (1998) *Proc. Nad. Acad. Sci. USA* 95, 5579–5583). Although these effects were reported to be RGD-independent, the finding that FAK phosphorylation and overall increase in cellular tyrosine phosphorylation is correlated with inhibition of motility supports the hypothesis that we offer here. Conclusive proof that the homodimeric structure of contortrostatin is what imparts this activity, and not some other unidentified properties, can be provided through use of a monomeric form of contortrostatin. At present, this form of contortrostatin is not available, however efforts are underway to generate monomeric contortrostatin.

In conclusion, this work identifies activity novel to the disintegrin family through which integrin signaling can be modulated in tumor cells. This activity appears to be unique to contortrostatin, as three other disintegrins have been found to lack the ability to stimulate tyrosine phosphorylation (Clark et al., supra). Recently, a number of new dimeric disintegrins have been purified from various snake venom (Marcinkiewicz et al., supra). It is unlikely that these molecules would demonstrate activity similar to contortrostatin because they are heterodimers lacking the RGD sequence, and they do not appear to interact with αvβ3. Our report identifies contortrostatin as a useful reagent for the further study of αvβ3 function, and identifies a novel integrin-mediated mechanism that may negatively effect tumor cell motility. We propose that the combined effects of blocking the binding of αvβ5, α5α1 and αvβ3 to the ECM and the initiation of inappropriate signals leading to hyperphosphorylation of critical signaling molecules can lead to immobilization of otherwise motile and invasive tumor cells. This proposal is consistent with our findings that contortrostatin effectively inhibits tumor cell invasiveness in vitro. Further work will examine the subcellular localization of CAS and FAK and the sti-ucture of the actin cytoskeleton in contortrostatin-treated cells, which we expect will reveal perturbations consistent with a reduced migratory capacity.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. An isolated protein comprising a contortrostatin monomer, a contortrostatin dimer, a contortrostatin precursor or biologically active variants thereof, said protein containing an amino acid sequence selected from the group consisting of:

(a) amino acid numbers 419 to 483 of SEQ ID NO: 2;
(b) amino acid numbers 191 to 410 of SEQ ID NO: 2;
(c) amino acid numbers 1 to 190 of SEQ ID NO: 2;
(d) SEQ ID NO: 2;
(e) an amino acid sequence at least 90% identical to (a), (b) or (d) as determined by FASTA or BLAST using default opening and gap penalties and a default scoring matrix; and
(f) an amino acid sequence at least 95% identical to (c) as determined by FASTA or BLAST using default opening and gap penalties and a default scoring matrix.

2. A recombinant protein according to claim 1.

3. A protein according to claim 1, said protein comprising a contortrostatin amino acid sequence which is at least 90% percent identical to amino acid numbers 419 to 483 of SEQ ID NO: 2, wherein said contortrostatin amino acid sequence (i) binds to integrin αvβ5 and (ii) induces αvβ3-mediated tyrosine phosphorylation of CAS and FAK in tumor cells.

4. A protein consisting essentially of an amino acid sequence selected from:

(a) amino acid numbers 419 to 483 of SEQ ID NO: 2;
(b) amino acid numbers 191 to 410 and 419 to 483 of SEQ ID NO: 2;
(c) SEQ ID NO: 2; or
(d) an amino acid sequence at least 90% identical to (a), (b) or (c) as determined by FASTA or BLAST using default opening and gap penalties and a default scoring matrix.

5. A purified protein according to claim 1, wherein said contortrostatin comprises a monomer having a molecular mass of about 5 to about 7 kDa.

6. A purified protein according to claim 5, wherein the contortrostatin monomer forms a homodimer with another contortrostatin monomer.

7. A purified contortrostatin protein according to claim 1 comprising a constrained Arg-Gly-Asp (RGD) sequence of a peptide loop of about 13 amino acid residues flanked by two Cys residues, wherein the peptide loop is an integrin antagonist which has an amino acid sequence comprising amino acid numbers 457 to 469 of SEQ ID NO: 2.

8. A protein according to claim 1 wherein said biologically active variants contain an amino acid sequence that is at least 95% identical to:

a) amino acid numbers 419 to 483 of SEQ ID NO: 2;
b) amino acid numbers 191 to 410 of SEQ ID NO: 2;
c) amino acid numbers 1 to 190 of SEQ ID NO: 2; or
d) SEQ ID NO: 2.

9. A preparation of contortrostatin precursor protein according to claim 1 encoded by the nucleotide sequence of SEQ ID NO: 1.

10. A preparation of contortrostatin precursor protein according the claim 9, wherein said contortrostatin is made by the process of transcribing and translating a cDNA molecule having the nucleotide sequence of SEQ ID NO:1.

11. The preparation of claim 10, wherein said transcribing and translating are performed in a recombinant-DNA containing host cell.

12. A preparation of contortrostatin, wherein said contortrostatin is made by a process of synthesizing a polypeptide having an amino acid sequence at least 95% identical to amino acid numbers 419 to 483 of SEQ ID NO:2 as determined by FASTA or BLAST using default opening and gap penalties and a default scoring matrix.

13. A recombinant protein according to claim 2 produced by a process comprising the steps of:
   a) culturing a host cell, said host cell being selected from the group consisting of mammalian cells, plant cells, insect cells, yeast and other fungi and bacteria, said host cell being transformed with a vector, said vector comprising a DNA sequence coding on expression for contortrostatin monomer, a contortrostatin dimer, a contortrostatin precursor or biologically active variants thereof; and
   b) recovering the contortrostatin monomer, contortrostatin dimer, contortrostatin precursor or biologically active variants thereof expressed by the host cell.

14. A pharmaceutically acceptable composition comprising a pharmaceutically acceptable carrier and a purified protein according to claim 1.

15. The recombinant protein of claim 13, wherein said DNA sequence is selected from the group consisting of:
   a) nucleotide numbers 1341 to 1535 of SEQ ID NO:1;
   b) nucleotide numbers 657 to 1316 of SEQ ID NO:1;
   c) nucleotide numbers 87 to 656 of SEQ ID NO: 1;
   d) nucleotide numbers 87 to 1535 of SEQ ID NO: 1; and
   e) SEQ ID NO:1.

* * * * *

SEQUENCE LISTING

```
<160> NUMBER OF SEQ ID NOS: 15

<210> SEQ ID NO 1
<211> LENGTH: 2029
<212> TYPE: DNA
<213> ORGANISM: Agkistrodon contortrix

<400> SEQUENCE: 1
gaattcgggg tcaatagagg aagagctcaa gttggcttga aagcaggaag agattgcctg      60
tcttccagcc aaatccagcc gccaaaatga tccaggttct cttggtgact ctatgcttag     120 cagctttttcc ttatcaaggg agctctataa tcctggaatc tgggaatgtt aatgattatg     180
aagtactgta tccacaaaaa gtcactgcat tgcccaaagg agcagttcag ccaaagtatg     240
```

-continued

```
aagacaccat gcaatatgaa tttaaagtga atggagagcc agtggtcctt cacctggaaa    300
aaaataaagg actttttca aaagattaca gcgagactca ttattcctct gatggcagaa    360
aaattacaac aaaccctccg gttgaggatc actgctatta tcatggacgc atccagaatg    420
atgctgactc aactgcaagc atcagtgcat gcaacggttt gaaaggacat ttcaagcttc    480
aaggggagac gtaccttatt gaacccttga agctttccga cagtgaagcc catgcagtct    540
acaaatatga aaacgtagaa aaagaagatg aggcccccaa aatgtgtggg gtaacccaga    600
ctaattggga atcagatgag cccatcaaaa aggcctctca gttaaatctt actcctgaac    660
aacaaggatt cccccaaaga tacattgagc ttgttgtagt tgcagatcac agaatgttca    720
cgaaatacaa cggcaattta aatactatta gaatatgggt acatgaactt gtcaacacta    780
tgaatgtgtt ttacagacct ttgaatattc gtgtctcact gactgaccta gaagtttggt    840
cagaccaaga tttgatcaac gtgcagccag cagcggctga tactttggaa gcatttggag    900
actggagaga gacagtcttg ctgaatcgca taagtcatga taatgctcag ttactcacgg    960
ccattgagct tgatggagaa actataggat tggctaacag gggcaccatg tgcgacccga   1020
agctttctac aggaattgtt caggatcata gtgcaataaa tctttgggtt gcagttacaa   1080
tgccccatga gatgggtcat aatctgggta ttagtcacga tggaaatcag tgtcattgcg   1140
atgctaactc atgcattatg agtgaagaac taagagaaca actttccttt gagttcagcg   1200
attgtagtca gaatcaatat cagacatatc ttactgatca taacccacaa tgcatgctca   1260
atgaaccctt gagaacagat attgtttcaa ctccagtttc tggaaatgaa cttttggaga   1320
cgggagaaga aagtgacttt gacgctcctg caaatccgtg ctgcgatgct gcaacatgta   1380
aactgacaac agggtcacag tgtgcagatg gactgtgttg tgaccagtgc aaatttatga   1440
aagaaggaac agtatgccgg agagcaaggg gtgatgacct ggatgattac tgcaatggca   1500
tatctgctgg ctgtcccaga aatcccttcc atgcctaacc aacaatggag atggaatggt   1560
ctgcagcaac aggcagtgtg ttgatctgaa tacagcctaa taatcaacct ctggcttctc   1620
tcagatttga tcatggagat ccttcttcca gaaggtttca cttccctcaa atccaaagag   1680
acccatctgc ctgcatccta ctagtaaatc acccttagct tccagatggt atccaaattc   1740
tgtaatattt cttctccata tttaatctat ttaccttttg ctgtaacaaa acctttttcc   1800
tgtcacaaag ctccatgggc atgtacagct tatctgctgt caagaaaaaa aatggccatt   1860
ttaccgtttg ccagttacaa agcacattta atgcaacaag ttcttccttt tgagctgatg   1920
tattcaaagt caatgcttcc tctcccaaaa tttcatgctg gcttcccaag atgtagctgc   1980
ttccgtcaat aaacaaacta ttctcattca aaaaaaaaaa cccgaattc               2029
```

```

<210> SEQ ID NO 2
<211> LENGTH: 483
<212> TYPE: PRT
<213> ORGANISM: Agkistrodon contortrix

<400> SEQUENCE: 2

Met Ile Gln Val Leu Leu Val Thr Leu Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Leu Tyr Pro Gln Lys Val Thr Ala Leu Pro Lys Gly Ala Val Gln
        35                  40                  45

Pro Lys Tyr Glu Asp Thr Met Gln Tyr Glu Phe Lys Val Asn Gly Glu
    50                  55                  60
```

-continued

```
Pro Val Val Leu His Leu Glu Lys Asn Lys Gly Leu Phe Ser Lys Asp
65                  70                  75                  80

Tyr Ser Glu Thr His Tyr Ser Ser Asp Gly Arg Lys Ile Thr Thr Asn
                85                  90                  95

Pro Pro Val Glu Asp His Cys Tyr Tyr His Gly Arg Ile Gln Asn Asp
            100                 105                 110

Ala Asp Ser Thr Ala Ser Ile Ser Ala Cys Asn Gly Leu Lys Gly His
            115                 120                 125

Phe Lys Leu Gln Gly Glu Thr Tyr Leu Ile Glu Pro Leu Lys Leu Ser
130                 135                 140

Asp Ser Glu Ala His Ala Val Tyr Lys Tyr Glu Asn Val Glu Lys Glu
145                 150                 155                 160

Asp Glu Ala Pro Lys Met Cys Gly Val Thr Gln Thr Asn Trp Glu Ser
                165                 170                 175

Asp Glu Pro Ile Lys Lys Ala Ser Gln Leu Asn Leu Thr Pro Glu Gln
            180                 185                 190

Gln Gly Phe Pro Gln Arg Tyr Ile Glu Leu Val Val Val Ala Asp His
            195                 200                 205

Arg Met Phe Thr Lys Tyr Asn Gly Asn Leu Asn Thr Ile Arg Ile Trp
210                 215                 220

Val His Glu Leu Val Asn Thr Met Asn Val Phe Tyr Arg Pro Leu Asn
225                 230                 235                 240

Ile Arg Val Ser Leu Thr Asp Leu Glu Val Trp Ser Asp Gln Asp Leu
                245                 250                 255

Ile Asn Val Gln Pro Ala Ala Ala Asp Thr Leu Glu Ala Phe Gly Asp
            260                 265                 270

Trp Arg Glu Thr Val Leu Leu Asn Arg Ile Ser His Asp Asn Ala Gln
            275                 280                 285

Leu Leu Thr Ala Ile Glu Leu Asp Gly Glu Thr Ile Gly Leu Ala Asn
290                 295                 300

Arg Gly Thr Met Cys Asp Pro Lys Leu Ser Thr Gly Ile Val Gln Asp
305                 310                 315                 320

His Ser Ala Ile Asn Leu Trp Val Ala Val Thr Met Ala His Glu Met
                325                 330                 335

Gly His Asn Leu Gly Ile Ser His Asp Gly Asn Gln Cys His Cys Asp
            340                 345                 350

Ala Asn Ser Cys Ile Met Ser Glu Glu Leu Arg Glu Gln Leu Ser Phe
            355                 360                 365

Glu Phe Ser Asp Cys Ser Gln Asn Gln Tyr Gln Thr Tyr Leu Thr Asp
370                 375                 380

His Asn Pro Gln Cys Met Leu Asn Glu Pro Leu Arg Thr Asp Ile Val
385                 390                 395                 400

Ser Thr Pro Val Ser Gly Asn Glu Leu Leu Glu Thr Gly Glu Glu Ser
                405                 410                 415

Asp Phe Asp Ala Pro Ala Asn Pro Cys Cys Asp Ala Ala Thr Cys Lys
            420                 425                 430

Leu Thr Thr Gly Ser Gln Cys Ala Asp Gly Leu Cys Cys Asp Gln Cys
            435                 440                 445

Lys Phe Met Lys Glu Gly Thr Val Cys Arg Arg Ala Arg Gly Asp Asp
450                 455                 460

Leu Asp Asp Tyr Cys Asn Gly Ile Ser Ala Gly Cys Pro Arg Asn Pro
465                 470                 475                 480
```

-continued

Phe His Ala

<210> SEQ ID NO 3
<211> LENGTH: 21
<212> TYPE: DNA
<213> ORGANISM: Trimeresurus gramineus

<400> SEQUENCE: 3
gtttacaggt tgcagcatcg c                                              21

<210> SEQ ID NO 4
<211> LENGTH: 21
<212> TYPE: DNA
<213> ORGANISM: Trimeresurus gramineus

<400> SEQUENCE: 4
gcgatgctgc aacctgtaaa c                                              21

<210> SEQ ID NO 5
<211> LENGTH: 21
<212> TYPE: DNA
<213> ORGANISM: Bacteriophage lambda

<400> SEQUENCE: 5
gcgatgctgc aacctgtaaa c                                              21

<210> SEQ ID NO 6
<211> LENGTH: 24
<212> TYPE: DNA
<213> ORGANISM: Bacteriophaeg Lambda gt10

<400> SEQUENCE: 6
cttatgagta tttcttccag ggta                                           24

<210> SEQ ID NO 7
<211> LENGTH: 71
<212> TYPE: PRT
<213> ORGANISM: Agkistrodon piscivorus

<400> SEQUENCE: 7

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Glu Gly
            20                  25                  30

Leu Cys Cys Asp Gln Cys Lys Phe Met Lys Glu Gly Thr Val Cys Arg
        35                  40                  45

Ala Arg Gly Asp Asp Val Asn Asp Tyr Cys Asn Gly Ile Ser Ala Gly
    50                  55                  60

Cys Pro Arg Asn Pro Phe His
65                  70

<210> SEQ ID NO 8
<211> LENGTH: 552
<212> TYPE: PRT
<213> ORGANISM: Trimeresurus gramineus

<400> SEQUENCE: 8

Glu Ala Gly Glu Asp Cys Asp Cys Gly Ser Pro Ala Asn Pro Cys Cys
1               5                   10                  15

Asp Ala Ala Thr Cys Lys Leu Ile Pro Gly Ala Gln Cys Gly Glu Gly
            20                  25                  30

-continued

```
Leu Cys Cys Asp Gln Cys Ser Phe Ile Glu Glu Gly Thr Val Cys Arg
         35                  40                  45

Ile Ala Arg Gly Asp Asp Leu Asp Asp Tyr Cys Asn Gly Arg Ser Ala
     50                  55                  60

Gly Cys Pro Arg Asn Pro Phe His Met Ile Gln Val Leu Leu Ile Thr
65                   70                  75                  80

Ile Cys Leu Ala Val Phe Pro Tyr Gln Gly Ser Ser Ile Ile Leu Glu
                 85                  90                  95

Ser Gly Asn Leu Asn Asp Tyr Glu Val Val Tyr Pro Glu Lys Val Thr
             100                 105                 110

Ala Leu Pro Lys Gly Ala Val Gln Gln Lys Tyr Glu Asp Ala Met Gln
         115                 120                 125

Tyr Glu Phe Lys Val Asn Gly Glu Pro Val Val Leu His Leu Glu Lys
     130                 135                 140

Asn Lys Gly Leu Phe Ser Glu Asp Tyr Ser Glu Ile His Tyr Ser Pro
145                 150                 155                 160

Asp Gly Arg Glu Ile Thr Ala Tyr Pro Ser Val Glu Asp His Cys Tyr
                 165                 170                 175

Tyr His Gly Arg Ile Glu Asn Asp Ala Asp Ser Thr Ala Ser Ile Ser
             180                 185                 190

Ala Cys Asp Gly Leu Lys Gly His Phe Lys Leu Gln Gly Glu Met Tyr
         195                 200                 205

Leu Ile Glu Pro Leu Glu Leu Ser Asp Ser Glu Ala His Ala Val Phe
     210                 215                 220

Lys Tyr Glu Asn Val Glu Lys Glu Asp Glu Pro Pro Lys Met Cys Gly
225                 230                 235                 240

Val Thr Gln Asn Trp Glu Ser Tyr Glu Ser Thr Lys Lys Ala Ser Gln
                 245                 250                 255

Leu Asn Val Thr Pro Glu Gln Gln Arg Phe Pro Gln Arg Tyr Ile Lys
             260                 265                 270

Leu Gly Ile Phe Val Asp His Gly Met Tyr Thr Lys Tyr Ser Gly Asn
         275                 280                 285

Ser Glu Arg Ile Thr Lys Arg Val His Gln Met Ile Asn Asn Ile Asn
     290                 295                 300

Met Met Cys Arg Ala Leu Asn Ile Val Thr Thr Leu Ser Val Leu Glu
305                 310                 315                 320

Ile Trp Ser Glu Lys Asp Leu Ile Thr Val Gln Ala Ser Ala Pro Thr
                 325                 330                 335

Thr Leu Thr Leu Phe Gly Ala Trp Arg Glu Thr Val Leu Leu Asn Arg
             340                 345                 350

Thr Ser His Asp His Ala Gln Leu Leu Thr Ala Thr Ile Phe Asn Gly
         355                 360                 365

Asn Val Ile Gly Arg Ala Pro Val Gly Gly Met Cys Asp Pro Lys Arg
     370                 375                 380

Ser Val Ala Ile Val Arg Asp His Asn Ala Ile Val Phe Val Val Ala
385                 390                 395                 400

Val Thr Met Thr His Glu Met Gly His Asn Leu Gly Met His Asp
                 405                 410                 415

Glu Asp Lys Cys Asn Cys Asn Thr Cys Ile Met Ser Lys Val Leu Ser
             420                 425                 430

Arg Gln Pro Ser Lys Tyr Phe Ser Glu Cys Ser Lys Asp Tyr Tyr Gln
         435                 440                 445

Thr Phe Leu Thr Asn His Asn Pro Gln Cys Ile Leu Asn Ala Pro Leu
```

```
                   450             455             460
Arg Thr Asp Thr Val Ser Thr Pro Val Ser Gly Asn Glu Leu Leu Glu
465                 470             475                 480

Ala Gly Glu Asp Cys Asp Cys Gly Ser Pro Ala Asn Pro Cys Cys Asp
                485             490             495

Ala Ala Thr Cys Lys Leu Ile Pro Gly Ala Gln Cys Gly Glu Gly Leu
            500             505             510

Cys Cys Asp Gln Cys Ser Phe Ile Glu Glu Gly Thr Val Cys Arg Ile
            515             520             525

Ala Arg Gly Asp Asp Leu Asp Asp Tyr Cys Asn Gly Arg Ser Ala Gly
        530             535             540

Cys Pro Arg Asn Pro Phe His Ala
545             550

<210> SEQ ID NO 9
<211> LENGTH: 73
<212> TYPE: PRT
<213> ORGANISM: Trimeresurus albolabris

<400> SEQUENCE: 9

Glu Ala Gly Glu Asp Cys Asp Cys Gly Ser Pro Ala Asn Pro Cys Cys
1               5                   10                  15

Asp Ala Ala Thr Cys Lys Leu Leu Pro Gly Ala Gln Cys Gly Glu Gly
                20                  25                  30

Leu Cys Cys Asp Gln Cys Ser Phe Met Lys Lys Gly Thr Ile Cys Arg
            35                  40                  45

Arg Ala Arg Gly Asp Asp Leu Asp Asp Tyr Cys Asn Gly Ile Ser Ala
        50                  55                  60

Gly Cys Pro Arg Asn Pro Leu His Ala
65                  70

<210> SEQ ID NO 10
<211> LENGTH: 73
<212> TYPE: PRT
<213> ORGANISM: Trimeresurus elegans

<400> SEQUENCE: 10

Glu Ala Gly Glu Glu Cys Asp Cys Gly Ser Pro Glu Asn Pro Cys Cys
1               5                   10                  15

Asp Ala Ala Thr Cys Lys Leu Arg Pro Gly Ala Gln Cys Ala Asp Gly
                20                  25                  30

Leu Cys Cys Asp Gln Cys Arg Phe Lys Lys Lys Arg Thr Ile Cys Arg
            35                  40                  45

Arg Ala Arg Gly Asp Asn Pro Asp Asp Arg Cys Thr Gly Gln Ser Ala
        50                  55                  60

Asp Cys Pro Arg Asn Gly Leu Tyr Ser
65                  70

<210> SEQ ID NO 11
<211> LENGTH: 68
<212> TYPE: PRT
<213> ORGANISM: Calloselasma rhodostoma

<400> SEQUENCE: 11

Gly Lys Glu Cys Asp Cys Ser Ser Pro Glu Asn Pro Cys Cys Asp Ala
1               5                   10                  15

Ala Thr Cys Lys Leu Arg Pro Gly Ala Gln Cys Gly Glu Gly Leu Cys
                20                  25                  30
```

```
Cys Glu Gln Cys Lys Phe Asp Arg Ala Gly Lys Ile Cys Arg Ile Pro
         35                  40                  45

Arg Gly Asp Met Pro Asp Arg Cys Thr Gly Gln Ser Ala Asp Cys
 50                  55                  60

Pro Arg Tyr His
 65
```

<210> SEQ ID NO 12
<211> LENGTH: 606
<212> TYPE: PRT
<213> ORGANISM: Crotalus atrox

<400> SEQUENCE: 12

```
Met Ile Gln Val Leu Leu Val Thr Ile Cys Leu Ala Ala Phe Pro Tyr
 1               5                   10                  15

Gln Gly Ser Ser Ile Ile Leu Glu Ser Gly Asn Val Asn Asp Tyr Glu
         20                  25                  30

Val Ile Tyr Pro Arg Lys Val Thr Ala Leu Pro Lys Gly Ala Val Gln
         35                  40                  45

Pro Lys Tyr Glu Asp Ala Met Gln Tyr Glu Leu Lys Val Asn Gly Glu
 50                  55                  60

Pro Val Val Leu His Leu Gly Lys Asn Lys Gly Leu Phe Ser Lys Asp
 65                  70                  75                  80

Tyr Ser Glu Thr His Tyr Ser Pro Asp Gly Arg Glu Ile Thr Thr Tyr
                 85                  90                  95

Pro Leu Val Glu Asp His Cys Tyr Tyr His Gly Ile Glu Asn Asp Ala
                 100                 105                 110

Asp Ser Thr Ala Ser Ile Ser Ala Cys Asn Gly Leu Lys Gly His Phe
             115                 120                 125

Lys Leu Gln Gly Glu Met Tyr Leu Ile Glu Pro Leu Lys Leu Pro Asp
 130                 135                 140

Ser Glu Ala His Ala Val Tyr Lys Tyr Glu Asn Val Glu Lys Glu Asp
 145                 150                 155                 160

Glu Ala Leu Lys Met Cys Gly Val Thr Gln Asn Trp Glu Ser Tyr Glu
                 165                 170                 175

Pro Ile Lys Lys Ala Ser Gln Leu Val Val Thr Ala Glu His Gln Lys
                 180                 185                 190

Tyr Asn Pro Phe Arg Phe Val Glu Leu Phe Leu Val Val Asp Lys Ala
             195                 200                 205

Met Val Thr Lys Asn Asn Gly Asp Leu Asp Lys Ile Lys Thr Arg Met
 210                 215                 220

Tyr Glu Ile Val Asn Thr Val Asn Glu Ile Tyr Arg Tyr Met Tyr Ile
 225                 230                 235                 240

His Val Ala Leu Val Gly Leu Glu Ile Trp Ser Asn Glu Asp Lys Ile
                 245                 250                 255

Thr Val Lys Pro Glu Ala Gly Tyr Thr Leu Asn Ala Phe Gly Glu Trp
                 260                 265                 270

Arg Lys Thr Asp Leu Leu Thr Arg Lys Lys His Asp Asn Ala Gln Leu
             275                 280                 285

Leu Thr Ala Ile Asp Leu Asp Arg Val Ile Gly Leu Ala Tyr Val Gly
 290                 295                 300

Ser Met Cys His Pro Lys Arg Ser Thr Gly Ile Ile Gln Asp Tyr Ser
 305                 310                 315                 320

Glu Ile Asn Leu Val Val Ala Val Ile Met Ala His Glu Met Gly His
```

```
                    325                 330                 335
Asn Leu Gly Ile Asn His Asp Ser Gly Tyr Cys Ser Cys Gly Asp Tyr
            340                 345                 350

Ala Cys Ile Met Arg Pro Glu Ile Ser Pro Glu Pro Ser Thr Phe Phe
            355                 360                 365

Ser Asn Cys Ser Tyr Phe Glu Cys Trp Asp Phe Ile Met Asn His Asn
        370                 375                 380

Pro Glu Cys Ile Leu Asn Glu Pro Leu Gly Thr Asp Ile Ile Ser Pro
385                 390                 395                 400

Pro Val Cys Gly Asn Glu Leu Leu Glu Val Gly Glu Cys Asp Cys
                405                 410                 415

Gly Thr Pro Glu Asn Cys Gln Asn Glu Cys Cys Asp Ala Ala Thr Cys
                420                 425                 430

Lys Leu Lys Ser Gly Ser Gln Cys Gly His Gly Asp Cys Cys Glu Gln
            435                 440                 445

Cys Lys Phe Ser Lys Ser Gly Thr Glu Cys Arg Ala Ser Met Glu Cys
        450                 455                 460

Asp Pro Ala Glu His Cys Thr Gly Gln Ser Ser Glu Cys Pro Ala Asp
465                 470                 475                 480

Val Phe His Lys Asn Gly Gln Pro Cys Leu Asp Asn Tyr Gly Tyr Cys
                485                 490                 495

Tyr Asn Gly Asn Cys Pro Ile Met Tyr His Gln Cys Tyr Asp Leu Phe
            500                 505                 510

Gly Ala Asp Val Tyr Glu Ala Glu Asp Ser Cys Phe Glu Arg Asn Gln
            515                 520                 525

Lys Gly Asn Tyr Gly Tyr Cys Arg Lys Glu Asn Gly Asn Lys Ile
            530                 535                 540

Pro Cys Ala Pro Glu Asp Val Lys Cys Gly Arg Leu Tyr Cys Lys Asp
545                 550                 555                 560

Asn Ser Pro Gly Asn Asn Pro Cys Lys Met Glu Tyr Ser Asn Glu Asp
                565                 570                 575

Glu His Lys Gly Met Val Leu Pro Gly Thr Lys Cys Ala Asp Gly Lys
            580                 585                 590

Val Cys Ser Asn Gly His Cys Val Asp Val Ala Thr Ala Tyr
        595                 600                 605

<210> SEQ ID NO 13
<211> LENGTH: 571
<212> TYPE: PRT
<213> ORGANISM: Bothrops jararaca

<400> SEQUENCE: 13

Ala Thr Arg Pro Lys Gly Ala Val Gln Pro Lys Tyr Glu Asp Ala Met
1               5                   10                  15

Gln Tyr Glu Phe Lys Val Asn Gly Glu Pro Val Val Leu His Leu Glu
            20                  25                  30

Lys Asn Lys Gly Leu Phe Ser Asp Tyr Ser Glu Ile His Tyr Ser
            35                  40                  45

Pro Asp Gly Arg Glu Ile Thr Thr Tyr Pro Pro Val Glu Asp His Cys
    50                  55                  60

Tyr Tyr His Gly Arg Ile Glu Asn Asp Ala Asp Ser Thr Ala Ser Ile
65                  70                  75                  80

Ser Ala Cys Asn Gly Leu Lys Gly Tyr Phe Lys Leu Gln Arg Glu Thr
                85                  90                  95
```

-continued

```
Tyr Phe Ile Glu Pro Leu Lys Leu Pro Asp Ser Glu Ala His Ala Val
            100                 105                 110

Phe Lys Tyr Glu Asn Val Glu Lys Glu Asp Ala Pro Lys Met Cys
        115                 120                 125

Gly Val Thr Gln Asn Trp Lys Ser Tyr Glu Pro Ile Lys Lys Ala Ser
        130                 135                 140

Gln Leu Ala Phe Thr Ala Glu Gln Gln Arg Tyr Asp Pro Tyr Lys Tyr
145                 150                 155                 160

Ile Glu Phe Phe Val Val Asp Gln Gly Thr Val Thr Lys Asn Asn
                165                 170                 175

Gly Asp Leu Asp Lys Ile Lys Ala Arg Met Tyr Glu Leu Ala Asn Ile
                180                 185                 190

Val Asn Glu Ile Phe Arg Tyr Leu Tyr Met His Val Ala Leu Val Gly
        195                 200                 205

Leu Glu Ile Trp Ser Asn Gly Asp Lys Ile Thr Val Lys Pro Asp Val
        210                 215                 220

Asp Tyr Thr Leu Asn Ser Phe Ala Glu Trp Arg Lys Thr Asp Leu Leu
225                 230                 235                 240

Thr Arg Lys Lys His Asp Asn Ala Gln Leu Leu Thr Ala Ile Asp Phe
                245                 250                 255

Asn Gly Pro Thr Ile Phe Tyr Ala Tyr Ile Gly Ser Met Cys His Pro
                260                 265                 270

Lys Arg Ser Val Gly Ile Val Gln Asp Tyr Ser Pro Ile Asn Leu Val
            275                 280                 285

Val Ala Val Ile Met Ala His Glu Met Gly His Asn Leu Gly Ile His
        290                 295                 300

His Asp Thr Gly Ser Cys Ser Cys Gly Asp Tyr Pro Cys Ile Met Gly
305                 310                 315                 320

Pro Thr Ile Ser Asn Glu Pro Ser Lys Phe Phe Ser Asn Cys Ser Tyr
                325                 330                 335

Ile Gln Cys Trp Asp Phe Ile Met Asn His Asn Pro Glu Cys Ile Ile
                340                 345                 350

Asn Glu Pro Leu Gly Thr Asp Ile Ile Ser Pro Pro Val Cys Gly Asn
            355                 360                 365

Glu Leu Leu Glu Val Gly Glu Glu Cys Asp Cys Gly Thr Pro Glu Asn
        370                 375                 380

Cys Gln Asn Glu Cys Cys Asp Ala Ala Thr Cys Lys Leu Lys Ser Gly
385                 390                 395                 400

Ser Gln Cys Gly His Gly Asp Cys Cys Glu Gln Cys Lys Phe Ser Lys
                405                 410                 415

Ser Gly Thr Glu Cys Arg Ala Ser Met Ser Glu Cys Asp Pro Ala Glu
            420                 425                 430

His Cys Thr Gly Gln Ser Ser Glu Cys Pro Ala Asp Val Phe His Lys
        435                 440                 445

Asn Gly Gln Pro Cys Leu Asp Asn Tyr Gly Tyr Cys Tyr Asn Gly Asn
450                 455                 460

Cys Pro Ile Met Tyr His Gln Cys Tyr Ala Leu Phe Gly Ala Asp Val
465                 470                 475                 480

Tyr Glu Ala Glu Asp Ser Cys Phe Lys Asp Asn Gln Lys Gly Asn Tyr
                485                 490                 495

Tyr Gly Tyr Cys Arg Lys Glu Asn Gly Lys Lys Ile Pro Cys Ala Pro
            500                 505                 510

Glu Asp Val Lys Cys Gly Arg Leu Tyr Cys Lys Asp Asn Ser Pro Gly
```

```
              515                 520                 525
Gln Asn Asn Pro Cys Lys Met Phe Tyr Ser Asn Asp Asp Glu His Lys
            530                 535                 540

Gly Met Val Leu Pro Gly Thr Lys Cys Ala Asp Gly Lys Val Cys Ser
545                 550                 555                 560

Asn Gly His Cys Val Asp Val Ala Thr Ala Tyr
                565                 570

<210> SEQ ID NO 14
<211> LENGTH: 478
<212> TYPE: PRT
<213> ORGANISM: Crotalus atrox

<400> SEQUENCE: 14

Met Ile Gln Val Leu Leu Val Thr Ile Cys Leu Ala Ala Phe Pro Tyr
1               5                   10                  15

Gln Gly Ser Ser Ile Ile Leu Glu Ser Gly Asn Val Asn Asp Tyr Glu
            20                  25                  30

Val Ile Tyr Pro Arg Lys Val Thr Ala Leu Pro Lys Gly Ala Val Gln
        35                  40                  45

Pro Lys Tyr Glu Asp Thr Met Gln Tyr Glu Leu Lys Val Asn Gly Glu
    50                  55                  60

Pro Val Val Leu His Leu Glu Lys Asn Lys Gly Leu Phe Ser Lys Asp
65                  70                  75                  80

Tyr Ser Glu Thr His Tyr Ser Phe Asp Gly Arg Lys Ile Thr Thr Asn
                85                  90                  95

Pro Ser Val Glu Asp His Cys Tyr Tyr His Gly Arg Ile Glu Asn Asp
            100                 105                 110

Ala Asp Ser Thr Ala Ser Ile Ser Ala Cys Asn Gly Leu Lys Gly His
        115                 120                 125

Phe Lys Leu Gln Gly Glu Met Tyr Leu Ile Glu Pro Leu Lys Leu Ser
    130                 135                 140

Asp Ser Glu Ala His Ala Val Phe Lys Leu Lys Asn Val Glu Lys Glu
145                 150                 155                 160

Asp Glu Ala Pro Lys Met Cys Gly Val Thr Gln Asn Trp Glu Ser Tyr
                165                 170                 175

Glu Pro Ile Lys Lys Ala Ser Asp Leu Asn Leu Asn Pro Glu His Gln
            180                 185                 190

Arg Tyr Val Glu Leu Phe Ile Val Val Asp His Gly Met Tyr Thr Lys
        195                 200                 205

Tyr Asn Gly Asp Ser Asp Lys Ile Arg Gln Arg Val His Gln Met Val
    210                 215                 220

Asn Ile Met Lys Glu Ser Tyr Thr Tyr Met Tyr Ile Asp Ile Leu Leu
225                 230                 235                 240

Ala Gly Ile Glu Ile Trp Ser Asn Gly Asp Leu Ile Asn Val Gln Pro
                245                 250                 255

Ala Ser Pro Asn Thr Leu Asn Ser Phe Gly Glu Trp Arg Glu Thr Asp
            260                 265                 270

Leu Leu Lys Arg Lys Ser His Asp Asn Ala Gln Leu Leu Thr Ser Ile
        275                 280                 285

Ala Phe Asp Glu Gln Ile Ile Gly Arg Ala Tyr Ile Gly Gly Ile Cys
    290                 295                 300

Asp Pro Lys Arg Ser Thr Gly Val Val Gln Asp His Ser Glu Ile Asn
305                 310                 315                 320
```

-continued

```
Leu Arg Val Ala Val Thr Met Thr His Glu Leu Gly His Asn Leu Gly
                325                 330                 335

Ile His His Asp Thr Asp Ser Cys Ser Cys Gly Gly Tyr Ser Cys Ile
                340                 345                 350

Met Ser Pro Val Ile Ser Asp Glu Pro Ser Lys Tyr Phe Ser Asp Cys
            355                 360                 365

Ser Tyr Ile Gln Cys Trp Glu Phe Ile Met Asn Gln Lys Pro Gln Cys
        370                 375                 380

Ile Leu Lys Lys Pro Leu Arg Thr Asp Thr Val Ser Thr Pro Val Ser
385                 390                 395                 400

Gly Asn Glu Leu Leu Glu Ala Gly Ile Glu Cys Asp Gly Gly Ser Leu
                405                 410                 415

Glu Asn Pro Cys Cys Tyr Ala Thr Thr Cys Lys Met Arg Pro Gly Ser
            420                 425                 430

Gln Cys Ala Glu Gly Leu Cys Cys Asp Gln Cys Arg Phe Met Lys Lys
        435                 440                 445

Gly Thr Val Cys Arg Val Ser Met Val Asp Arg Asn Asp Asp Thr Cys
    450                 455                 460

Thr Gly Gln Ser Ala Asp Cys Pro Arg Asn Gly Leu Tyr Gly
465                 470                 475
```

<210> SEQ ID NO 15
<211> LENGTH: 6
<212> TYPE: PRT
<213> ORGANISM: Artificial Sequence
<220> FEATURE:
<223> OTHER INFORMATION: RGD PEPTIDE

<400> SEQUENCE: 15

```
Gly Arg Gly Asp Ser Pro
1               5
```